(12) United States Patent
Miller et al.

(10) Patent No.: US 10,245,010 B2
(45) Date of Patent: Apr. 2, 2019

(54) ASSEMBLY FOR COUPLING POWERED DRIVER WITH INTRAOSSEOUS DEVICE

(71) Applicant: TELEFLEX MEDICAL DEVICES S.À R.L., Luxembourg (LU)

(72) Inventors: Larry J. Miller, Spring Branch, TX (US); David S. Bolleter, San Antonio, TX (US); Robert W. Titkemeyer, San Antonio, TX (US); Christopher Brian Kilcoin, South Lake Tahoe, CA (US); Matthew T. Harmon, Santa Cruz, CA (US); Bradford Hughes Craig, Royal Oaks, CA (US)

(73) Assignee: TELEFLEX MEDICAL DEVICES S.A.R.L, Luxembourg (LU)

( * ) Notice: Subject to any disclaimer, the term of this patent is extended or adjusted under 35 U.S.C. 154(b) by 0 days.

(21) Appl. No.: 14/184,194

(22) Filed: Feb. 19, 2014

(65) Prior Publication Data

US 2014/0343454 A1    Nov. 20, 2014

Related U.S. Application Data

(60) Division of application No. 11/853,678, filed on Sep. 11, 2007, now Pat. No. 8,668,698, which is a
(Continued)

(51) Int. Cl.
*A61B 10/02* (2006.01)
*A61B 17/00* (2006.01)
(Continued)

(52) U.S. Cl.
CPC ............ *A61B 10/025* (2013.01); *A61B 46/00* (2016.02); *A61B 46/10* (2016.02); *A61B 50/30* (2016.02);
(Continued)

(58) Field of Classification Search
CPC ... A61B 17/16; A61B 17/162; A61B 17/1622; A61B 17/1624; A61B 17/1631
See application file for complete search history.

(56) References Cited

U.S. PATENT DOCUMENTS

| 1,539,637 A | 5/1925 | Bronner ......................... 433/81 |
| 2,817,648 A | 4/1943 | Siqveland ....................... 32/26 |

(Continued)

FOREIGN PATENT DOCUMENTS

| CA | 2 138 842 | 6/1996 |
| CA | 2 454 600 | 1/2004 |

(Continued)

OTHER PUBLICATIONS

"Proven reliability for quality bone marrow samples", Special Procedures, Cardinal Health, 6 pages 2003.
(Continued)

*Primary Examiner* — Sean P Dougherty
*Assistant Examiner* — Patrick Fernandes
(74) *Attorney, Agent, or Firm* — Baker & Hostetler LLP

(57) ABSTRACT

Apparatus and methods are provided to remove biopsy specimens from a bone and/or associated bone marrow using a powered drive and an intraosseous (IO) needle set. The powered driver may rotate the IO needle set at an optimum speed to obtain a biopsy sample of bone and/or bone marrow. Apparatus and methods may also be provided for aspiration of bone marrow and/or stem cell transplant procedures. The apparatus may include a powered driver, a coupler assembly, a containment bag or sterile sleeve and various IO needles and IO needle sets with associated hubs and/or hub assemblies. Each IO needle set may include a cannula or catheter and an associated trocar stylet with respective tips operable to penetrate a bone and/or bone marrow with minimum trauma to a patient. Each hub (Continued)

assembly may be used to releasably dispose a respective stylet within an associated generally hollow cannula. Some coupler assemblies and/or hub assemblies may also be used with manual drivers.

20 Claims, 20 Drawing Sheets

Related U.S. Application Data continuation-in-part of application No. 10/449,503, filed on May 30, 2003, now Pat. No. 7,670,328.

(60) Provisional application No. 60/384,756, filed on May 31, 2002, provisional application No. 60/825,325, filed on Sep. 12, 2006, provisional application No. 60/910,122, filed on Apr. 4, 2007.

(51) Int. Cl.
| | |
|---|---|
| *A61B 46/00* | (2016.01) |
| *A61B 46/10* | (2016.01) |
| *A61B 46/23* | (2016.01) |
| *A61B 50/30* | (2016.01) |
| *A61B 50/33* | (2016.01) |
| *A61B 90/00* | (2016.01) |

(52) U.S. Cl.
CPC .......... *A61B 50/33* (2016.02); *A61B 10/0283* (2013.01); *A61B 46/23* (2016.02); *A61B 2010/0208* (2013.01); *A61B 2010/0258* (2013.01); *A61B 2017/00734* (2013.01); *A61B 2090/062* (2016.02); *Y10T 408/94* (2015.01)

(56) References Cited

U.S. PATENT DOCUMENTS

| | | | |
|---|---|---|---|
| 2,419,045 A | 4/1947 | Whittaker | 128/305 |
| 2,773,501 A | 12/1956 | Young | 128/221 |
| 2,860,635 A | 11/1958 | Wilburn | 604/190 |
| 3,104,448 A | 9/1963 | Morrow et al. | 27/24.1 |
| 2,130,845 A | 2/1964 | Horner | 128/210 |
| 3,173,417 A | 3/1965 | Horner | 128/205 |
| 3,175,554 A | 3/1965 | Stewart | 128/2 |
| 3,507,276 A | 4/1970 | Burgess et al. | 128/173 |
| 3,529,580 A | 9/1970 | Stevens | 122/406.5 |
| 3,543,966 A | 12/1970 | Ryan et al. | 222/94 |
| 3,697,223 A | 10/1972 | Kovalcik et al. | |
| 3,750,667 A | 8/1973 | Pshenichny | 604/117 |
| 3,802,555 A | 4/1974 | Grasty et al. | |
| 3,815,605 A | 6/1974 | Schmidt et al. | 128/305 |
| 3,835,860 A | 9/1974 | Garreston et al. | 128/310 |
| 3,893,445 A | 7/1975 | Hofsess | 128/2 |
| 3,991,765 A | 11/1976 | Cohen | 128/305 |
| 4,021,920 A | 5/1977 | Kirschner et al. | 32/28 |
| 4,099,518 A | 7/1978 | Baylis et al. | 600/567 |
| 4,142,517 A | 3/1979 | Stavropoulos et al. | 128/2 B |
| 4,154,026 A | 5/1979 | Palthe | 128/303 R |
| 4,170,993 A | 10/1979 | Alvarez | 128/214 R |
| 4,185,619 A | 1/1980 | Reiss | 128/1.1 |
| 4,194,505 A | 3/1980 | Schmitz | 128/218 |
| 4,258,722 A | 3/1981 | Sessions | 128/753 |
| 4,262,676 A | 4/1981 | Jamshidi | 128/753 |
| 4,306,570 A | 12/1981 | Matthews | 128/754 |
| 4,333,459 A | 6/1982 | Becker | 128/218 |
| 4,359,052 A | 11/1982 | Staub | 606/30 |
| 4,381,777 A | 5/1983 | Garnier | 604/188 |
| 4,399,723 A | 8/1983 | Marleau | 81/437 |
| 4,413,760 A | 11/1983 | Paton | |
| 4,420,085 A | 12/1983 | Wilson et al. | |
| 4,441,563 A | 4/1984 | Walton | 173/163 |
| 4,469,109 A | 9/1984 | Mehl | 128/753 |
| 4,484,577 A | 11/1984 | Sackner et al. | 128/203.28 |
| 4,543,966 A | 10/1985 | Islan et al. | 128/754 |
| 4,553,539 A | 11/1985 | Morris | 128/132 D |
| 4,578,064 A | 3/1986 | Sarnoff et al. | 604/191 |
| 4,605,011 A | 8/1986 | Naslund | 128/752 |
| 4,620,539 A | 11/1986 | Andrews | 128/303 |
| 4,630,616 A | 12/1986 | Tretinyak | |
| 4,646,731 A | 3/1987 | Brower | 128/156 |
| 4,654,492 A | 3/1987 | Koerner et al. | 200/153 |
| 4,655,226 A | 4/1987 | Lee | 128/754 |
| 4,659,329 A | 4/1987 | Annis | 604/180 |
| 4,692,073 A | 9/1987 | Martindell | 408/239 A |
| 4,711,636 A | 12/1987 | Bierman | 604/180 |
| 4,713,061 A | 12/1987 | Tarello et al. | 604/200 |
| 4,716,901 A | 1/1988 | Jackson et al. | 128/343 |
| 4,723,945 A | 2/1988 | Theiling | 604/232 |
| 4,736,850 A | 4/1988 | Bowman et al. | |
| 4,758,225 A | 7/1988 | Cox et al. | 604/126 |
| 4,762,118 A | 8/1988 | Lia | 127/4 |
| 4,772,261 A | 9/1988 | Von Hoff et al. | 604/51 |
| 4,787,893 A | 11/1988 | Villette | 604/188 |
| 4,793,363 A | 12/1988 | Ausherman et al. | 128/754 |
| 4,844,259 A | 7/1989 | Glowczewskie et al. | 206/370 |
| 4,867,158 A | 9/1989 | Sugg | 128/305 |
| 4,919,146 A | 4/1990 | Rhinehart et al. | 128/565 |
| 4,921,013 A | 5/1990 | Spalink et al. | 137/614.05 |
| 4,935,010 A | 6/1990 | Cox et al. | 604/122 |
| 4,940,459 A | 7/1990 | Noce | 604/98 |
| 4,944,677 A | 7/1990 | Alexandre | 433/165 |
| 4,969,870 A | 11/1990 | Kramer | 604/51 |
| 4,986,279 A | 1/1991 | O'Neill | 128/754 |
| 5,002,546 A | 3/1991 | Romano | 606/80 |
| 5,025,797 A | 6/1991 | Baran | 128/754 |
| 5,036,860 A | 8/1991 | Leigh et al. | 128/754 |
| 5,057,085 A | 10/1991 | Kopans | 604/173 |
| 5,074,311 A | 12/1991 | Hasson | 128/754 |
| 5,116,324 A | 5/1992 | Brierley et al. | 604/180 |
| 5,120,312 A | 6/1992 | Wigness et al. | 604/175 |
| 5,122,114 A | 6/1992 | Miller | 604/49 |
| 5,133,359 A | 7/1992 | Kedem | 128/754 |
| 5,137,518 A | 8/1992 | Mersch | 604/168 |
| 5,139,500 A | 8/1992 | Schwartz | 606/96 |
| RE24,056 E | 9/1992 | Lindgren et al. | 128/754 |
| 5,172,701 A | 12/1992 | Leigh | 128/753 |
| 5,172,702 A | 12/1992 | Leigh et al. | 128/754 |
| 5,176,643 A | 1/1993 | Kramer | 604/135 |
| 5,195,985 A | 3/1993 | Hall | 604/195 |
| 5,203,056 A | 4/1993 | Funk et al. | 24/543 |
| 5,207,697 A | 5/1993 | Carusillo | 606/167 |
| 5,210,376 A | 5/1993 | Caviar | 604/264 |
| 5,249,583 A | 10/1993 | Mallaby | 128/754 |
| 5,257,632 A | 11/1993 | Turkel | 128/754 |
| 5,261,877 A | 11/1993 | Fine et al. | 604/540 |
| 5,269,785 A | 12/1993 | Bonutti | 606/80 |
| 5,279,306 A | 1/1994 | Mehl | 128/753 |
| 5,312,351 A | 5/1994 | Gerrone | 604/117 |
| 5,312,364 A | 5/1994 | Jacobs | 604/180 |
| 5,312,408 A | 5/1994 | Brown | 606/80 |
| 5,315,737 A | 5/1994 | Ouimet | 600/566 |
| 5,324,300 A | 6/1994 | Elias et al. | 606/180 |
| 5,330,480 A | 7/1994 | Meloul et al. | |
| 5,332,398 A | 7/1994 | Miller | 604/175 |
| 5,333,790 A | 8/1994 | Christopher | 239/391 |
| 5,341,823 A | 8/1994 | Manosalva et al. | 128/898 |
| 5,348,022 A | 9/1994 | Leigh et al. | 128/753 |
| 5,356,006 A | 10/1994 | Alpern et al. | 206/363 |
| 5,357,974 A | 10/1994 | Baldridge | 128/754 |
| 5,368,046 A | 11/1994 | Scarfone et al. | 128/754 |
| 5,372,583 A | 12/1994 | Roberts et al. | 604/51 |
| 5,383,859 A | 1/1995 | Sewell et al. | 604/164 |
| 5,385,553 A | 1/1995 | Hart et al. | 604/167 |
| 5,400,798 A | 3/1995 | Baran | 128/754 |
| 5,405,348 A | 4/1995 | Anspach et al. | 606/80 |
| 5,405,362 A | 4/1995 | Kramer et al. | 607/5 |
| 5,423,824 A | 6/1995 | Akerfeldt et al. | 606/80 |
| 5,431,655 A | 7/1995 | Melker | 606/79 |
| 5,451,210 A | 9/1995 | Kramer et al. | 604/137 |
| 5,484,442 A | 1/1996 | Melker et al. | 606/79 |
| 5,505,737 A * | 4/1996 | Gosselin | A61B 17/32002 279/75 |

(56) References Cited

U.S. PATENT DOCUMENTS

| | | | |
|---|---|---|---|
| 5,514,097 A | 5/1996 | Knauer | 604/136 |
| 5,526,821 A | 6/1996 | Jamshidi | 128/753 |
| 5,529,580 A | 6/1996 | Kusunoki et al. | 606/170 |
| 5,549,565 A | 8/1996 | Ryan et al. | 604/167.03 |
| 5,554,154 A | 9/1996 | Rosenberg | 606/80 |
| 5,556,399 A | 9/1996 | Huebner et al. | 606/80 |
| 5,558,737 A | 9/1996 | Brown et al. | 156/172 |
| D369,858 S | 12/1996 | Baker et al. | D24/112 |
| 5,586,847 A | 12/1996 | Matter, Jr. et al. | |
| 5,591,188 A | 1/1997 | Waisman | 606/182 |
| 5,595,186 A | 1/1997 | Rubinstein et al. | 128/754 |
| 5,601,559 A | 2/1997 | Melker et al. | 606/79 |
| 5,624,214 A | 4/1997 | Carroll | |
| 5,632,747 A | 5/1997 | Scarborough et al. | 606/79 |
| 5,672,155 A | 9/1997 | Riley et al. | 604/154 |
| 5,724,873 A | 3/1998 | Hillinger | 81/451 |
| 5,733,262 A | 3/1998 | Paul | 604/116 |
| 5,713,368 A | 5/1998 | Leigh | 128/753 |
| 5,752,923 A | 5/1998 | Terwilliger | 600/562 |
| 5,762,639 A | 6/1998 | Gibbs | 604/272 |
| 5,769,086 A | 6/1998 | Ritchart | 128/753 |
| 5,779,708 A | 7/1998 | Wu | 606/80 |
| 5,800,389 A | 9/1998 | Burney et al. | 604/93 |
| 5,807,277 A | 9/1998 | Swaim | 600/567 |
| 5,810,826 A | 9/1998 | Akerfeldt | 606/80 |
| 5,817,052 A | 10/1998 | Johnson | 604/51 |
| 5,823,970 A | 10/1998 | Terwilliger | 600/564 |
| D403,405 S | 12/1998 | Terwilliger | D24/130 |
| 5,858,005 A | 1/1999 | Kriesel | 604/180 |
| 5,865,711 A | 2/1999 | Kramer et al. | 604/136 |
| 5,868,750 A | 2/1999 | Schultz | 606/104 |
| 5,873,510 A | 2/1999 | Hirai et al. | 227/130 |
| 5,885,226 A | 3/1999 | Rubinstein et al. | 600/564 |
| 5,891,085 A | 4/1999 | Lilley et al. | 604/68 |
| 5,911,701 A | 6/1999 | Miller et al. | 604/22 |
| 5,911,708 A | 6/1999 | Teirstein | 604/183 |
| 5,916,229 A | 6/1999 | Evans | 606/171 |
| 5,919,172 A | 7/1999 | Golba, Jr. | 604/272 |
| 5,924,864 A | 7/1999 | Loge et al. | 433/118 |
| 5,927,976 A | 7/1999 | Wu | 433/82 |
| 5,928,238 A | 7/1999 | Scarborough | 606/79 |
| 5,941,706 A | 8/1999 | Ura | 433/165 |
| 5,941,851 A | 8/1999 | Coffey et al. | 604/131 |
| 5,951,026 A | 9/1999 | Harman et al. | 279/143 |
| 5,960,797 A | 10/1999 | Kramer et al. | 128/899 |
| 5,980,545 A | 11/1999 | Pacala | 606/170 |
| 5,989,257 A * | 11/1999 | Tidwell | A61B 17/162 279/30 |
| 5,993,417 A | 11/1999 | Yerfino et al. | 604/110 |
| 5,993,454 A | 11/1999 | Longo | 512/110 |
| 6,007,496 A | 12/1999 | Brannon | 600/565 |
| 6,017,348 A | 1/2000 | Hart et al. | 606/79 |
| 6,018,094 A | 1/2000 | Fox | 623/11 |
| 6,022,324 A | 2/2000 | Skinner | 600/566 |
| 6,027,458 A | 2/2000 | Janssens | 600/567 |
| 6,033,369 A | 3/2000 | Goldenberg | 600/567 |
| 6,033,411 A | 3/2000 | Preissman | 606/99 |
| 6,063,037 A | 5/2000 | Mittermeier | 600/567 |
| 6,080,115 A | 6/2000 | Rubinstein | 600/564 |
| 6,083,176 A | 7/2000 | Terwilliger | 600/562 |
| 6,086,544 A | 7/2000 | Hibner et al. | 600/568 |
| 6,096,042 A | 8/2000 | Herbert | 606/80 |
| 6,102,915 A | 8/2000 | Bresler et al. | 606/80 |
| 6,106,484 A | 8/2000 | Terwilliger | 600/568 |
| 6,110,128 A | 8/2000 | Abdekubm et al. | 600/566 |
| 6,110,129 A | 8/2000 | Terwilliger | 600/567 |
| 6,110,174 A | 8/2000 | Nichter | 606/72 |
| 6,120,462 A | 9/2000 | Hibner et al. | 600/566 |
| 6,135,769 A | 10/2000 | Kwan | 433/80 |
| 6,159,163 A | 12/2000 | Strauss et al. | 600/566 |
| 6,162,203 A | 12/2000 | Haaga | 604/272 |
| 6,183,442 B1 | 2/2001 | Athanasiou et al. | 604/154 |
| 6,210,376 B1 | 4/2001 | Grayson | 604/264 |
| 6,217,561 B1 | 4/2001 | Gibbs | 604/264 |
| 6,221,029 B1 | 4/2001 | Mathis | 600/564 |
| 6,228,049 B1 | 5/2001 | Schroeder et al. | 604/93.01 |
| 6,228,088 B1 | 5/2001 | Miller | 606/80 |
| 6,238,355 B1 | 5/2001 | Daum | 600/567 |
| 6,247,110 B1 | 6/2001 | Reiley et al. | 606/93 |
| 6,247,928 B1 | 6/2001 | Meller | 433/80 |
| 6,257,351 B1 | 7/2001 | Ark | 173/178 |
| 6,267,763 B1 | 7/2001 | Castro | 606/86 A |
| 6,270,087 B1 * | 8/2001 | Mickel | A61B 17/162 279/75 |
| 6,273,715 B1 | 8/2001 | Meller | 433/80 |
| 6,273,862 B1 | 8/2001 | Privitera et al. | 600/568 |
| 6,283,925 B1 | 9/2001 | Terwilliger | 600/568 |
| 6,283,970 B1 | 9/2001 | Lubinus | 606/80 |
| 6,287,114 B1 | 9/2001 | Meller | 433/80 |
| 6,302,852 B1 | 10/2001 | Fleming | 600/567 |
| 6,309,358 B1 | 10/2001 | Okubo | 600/466 |
| 6,312,394 B1 | 11/2001 | Fleming | 600/567 |
| 6,315,737 B1 | 11/2001 | Skinner | 600/566 |
| 6,325,806 B1 | 12/2001 | Fox | 606/80 |
| 6,328,701 B1 | 12/2001 | Terwilliger | 600/567 |
| 6,328,744 B1 | 12/2001 | Harari et al. | 606/80 |
| 6,358,252 B1 | 3/2002 | Shapira | 606/80 |
| 6,382,212 B1 | 5/2002 | Borchard | 128/849 |
| 6,402,701 B1 | 6/2002 | Kaplan et al. | 600/567 |
| 6,419,490 B1 | 7/2002 | Kitchings Weathers, Jr. | 433/165 |
| 6,425,888 B1 | 7/2002 | Embleton et al. | 604/290 |
| 6,428,487 B1 | 8/2002 | Burdoff et al. | 600/568 |
| 6,443,910 B1 | 9/2002 | Krueeger | 600/567 |
| 6,458,117 B1 | 10/2002 | Pollins | 604/523 |
| 6,468,248 B1 | 10/2002 | Gibbs | 604/164.01 |
| 6,478,751 B1 | 11/2002 | Krueger | 600/566 |
| 6,488,636 B2 | 12/2002 | Bryan | 600/565 |
| 6,523,698 B1 | 2/2003 | Dennehey | 210/435 |
| 6,527,736 B1 | 3/2003 | Attinger et al. | 604/43 |
| 6,527,778 B2 | 3/2003 | Athanasiou | 606/80 |
| 6,540,697 B2 | 4/2003 | Van Bladel et al. | 600/564 |
| 6,547,451 B1 | 4/2003 | Meller | 433/80 |
| 6,547,511 B1 | 4/2003 | Adams | 414/46.4 |
| 6,550,786 B2 * | 4/2003 | Gifford | B23Q 3/12 279/143 |
| 6,554,779 B2 | 4/2003 | Viola et al. | 600/568 |
| 6,555,212 B2 | 4/2003 | Boiocchi et al. | 428/295.4 |
| 6,572,563 B2 | 6/2003 | Ouchi | 600/564 |
| 6,575,919 B1 | 6/2003 | Reiley et al. | 600/567 |
| 6,582,399 B1 | 6/2003 | Smith et al. | 604/152 |
| 6,585,622 B1 | 7/2003 | Shum et al. | 482/8 |
| 6,595,911 B2 | 7/2003 | LoVuolo | 600/30 |
| 6,595,979 B1 | 7/2003 | Epstein et al. | 604/506 |
| 6,613,054 B2 | 9/2003 | Scribner et al. | 606/93 |
| 6,616,632 B2 | 9/2003 | Sharp et al. | 604/117 |
| 6,620,111 B2 | 9/2003 | Stephens et al. | 600/567 |
| 6,626,848 B2 | 9/2003 | Nueenfeldt | 600/564 |
| 6,626,887 B1 | 9/2003 | Wu | 604/512 |
| 6,638,235 B2 | 10/2003 | Miller et al. | 600/566 |
| 6,656,133 B2 | 12/2003 | Voegele et al. | 600/568 |
| 6,689,072 B2 | 2/2004 | Kaplan et al. | 600/567 |
| 6,702,760 B2 | 3/2004 | Krause et al. | 600/564 |
| 6,702,761 B1 | 3/2004 | Damadian et al. | 600/576 |
| 6,706,016 B2 | 3/2004 | Cory et al. | 604/117 |
| 6,716,192 B1 | 4/2004 | Orosz, Jr. | 604/117 |
| 6,716,215 B1 | 4/2004 | David et al. | 606/80 |
| 6,716,216 B1 | 4/2004 | Boucher et al. | 606/86 |
| 6,730,043 B2 | 5/2004 | Krueger et al. | 600/567 |
| 6,730,044 B2 | 5/2004 | Stephens et al. | 600/568 |
| 6,749,576 B2 | 6/2004 | Bauer | 600/567 |
| 6,752,768 B2 | 6/2004 | Burdoff et al. | 600/568 |
| 6,752,816 B2 | 6/2004 | Culp et al. | 606/170 |
| 6,758,824 B1 | 7/2004 | Miller et al. | 600/568 |
| 6,761,726 B1 | 7/2004 | Findlay | 606/182 |
| 6,796,957 B2 | 9/2004 | Carpenter et al. | 604/93.01 |
| 6,846,314 B2 | 1/2005 | Shapira | 606/80 |
| 6,849,051 B2 | 2/2005 | Sramek et al. | 600/565 |
| 6,855,148 B2 | 2/2005 | Foley et al. | 606/86 |
| 6,860,860 B2 | 3/2005 | Viola | 600/564 |
| 6,875,183 B2 | 4/2005 | Cervi | 600/567 |
| 6,875,219 B2 | 4/2005 | Arramon et al. | 606/92 |
| 6,884,245 B2 | 4/2005 | Spranza | 606/79 |
| 6,887,209 B2 | 5/2005 | Kadziauskas et al. | 600/565 |

(56) References Cited

U.S. PATENT DOCUMENTS

| | | | |
|---|---|---|---|
| 6,890,308 B2 | 5/2005 | Islam | 600/564 |
| 6,905,486 B2 | 6/2005 | Gibbs | 604/510 |
| 6,930,461 B2 | 8/2005 | Ruthowski | 318/567 |
| 6,942,669 B2 | 9/2005 | Kurc | 606/80 |
| 6,969,373 B2 | 11/2005 | Schwartz | 604/170.03 |
| 7,008,381 B2 | 3/2006 | Janssens | 600/564 |
| 7,008,383 B1 | 3/2006 | Damadian et al. | 600/567 |
| 7,008,394 B2 | 3/2006 | Geise et al. | 615/6.15 |
| 7,025,732 B2 | 4/2006 | Thompson et al. | 600/654 |
| 7,063,672 B2 | 6/2006 | Schramm | 600/564 |
| 7,137,985 B2 | 11/2006 | Jahng | 606/61 |
| 7,186,257 B2 | 3/2007 | Kim | 606/96 |
| 7,207,949 B2 | 4/2007 | Miles et al. | 600/554 |
| 7,226,450 B2 | 6/2007 | Athanasiou et al. | 606/80 |
| 7,229,401 B2 | 6/2007 | Kindlein | 600/7 |
| 7,670,328 B2 | 3/2010 | Miller | 604/506 |
| 7,699,850 B2 | 4/2010 | Miller | 606/80 |
| 7,811,260 B2 | 10/2010 | Miller et al. | 604/188 |
| 7,815,642 B2 | 10/2010 | Miller | 606/79 |
| 7,850,620 B2 | 12/2010 | Miller et al. | 600/568 |
| 7,951,089 B2 | 5/2011 | Miller | 600/566 |
| 8,038,664 B2 | 10/2011 | Miller et al. | 604/506 |
| 8,142,365 B2 | 3/2012 | Miller | 600/566 |
| 8,308,693 B2 | 11/2012 | Miller et al. | 604/188 |
| 8,419,683 B2 | 4/2013 | Miller et al. | 604/117 |
| 8,480,632 B2 | 7/2013 | Miller et al. | 604/188 |
| 8,506,568 B2 | 8/2013 | Miller | 606/80 |
| 8,641,715 B2 | 2/2014 | Miller | 606/80 |
| 8,656,929 B2 | 2/2014 | Miller | 128/898 |
| 8,668,698 B2 | 3/2014 | Miller | 606/80 |
| 8,684,978 B2 | 4/2014 | Miller | 604/235 |
| 8,690,791 B2 | 4/2014 | Miller | 600/562 |
| 8,715,287 B2 | 5/2014 | Miller | 606/80 |
| 2001/0014439 A1 | 8/2001 | Meller et al. | 433/50 |
| 2001/0026051 A1 | 10/2001 | Gifford | |
| 2001/0047183 A1 | 11/2001 | Privitera et al. | 606/170 |
| 2001/0053888 A1 | 12/2001 | Athanasiou et al. | 604/154 |
| 2002/0042581 A1 | 4/2002 | Cervi | 600/567 |
| 2002/0055713 A1 | 5/2002 | Gibbs | 604/164.01 |
| 2002/0120212 A1 | 8/2002 | Ritchart et al. | 600/567 |
| 2002/0138021 A1 | 9/2002 | Pflueger | 600/565 |
| 2002/0151902 A1* | 10/2002 | Riedel | A61B 17/32002 606/80 |
| 2003/0028146 A1 | 2/2003 | Aves | 604/164.06 |
| 2003/0032939 A1 | 2/2003 | Gibbs | 604/510 |
| 2003/0036747 A1 | 2/2003 | Ie et al. | 606/1 |
| 2003/0050574 A1 | 3/2003 | Krueger | 600/567 |
| 2003/0114858 A1 | 6/2003 | Athanasiou et al. | 606/80 |
| 2003/0125639 A1 | 7/2003 | Fisher et al. | 600/564 |
| 2003/0153842 A1 | 8/2003 | Lamoureux | 600/564 |
| 2003/0191414 A1 | 10/2003 | Reiley | 600/567 |
| 2003/0195436 A1 | 10/2003 | Van Bladel et al. | 600/584 |
| 2003/0199787 A1 | 10/2003 | Schwindt | 600/568 |
| 2003/0216667 A1 | 11/2003 | Viola | 600/564 |
| 2003/0225344 A1 | 12/2003 | Miller | 600/566 |
| 2003/0225364 A1 | 12/2003 | Kraft et al. | 604/35 |
| 2004/0019297 A1 | 1/2004 | Angel | 600/564 |
| 2004/0019299 A1 | 1/2004 | Richart et al. | 600/567 |
| 2004/0034280 A1 | 2/2004 | Privitera et al. | 600/170 |
| 2004/0049128 A1 | 3/2004 | Miller et al. | 600/566 |
| 2004/0064136 A1 | 4/2004 | Papineau et al. | 606/41 |
| 2004/0092946 A1 | 5/2004 | Bagga et al. | 606/93 |
| 2004/0153003 A1 | 8/2004 | Cicenas et al. | 600/564 |
| 2004/0158172 A1 | 8/2004 | Hancock | 600/564 |
| 2004/0158173 A1 | 8/2004 | Voegele et al. | 600/568 |
| 2004/0162505 A1 | 8/2004 | Kaplan et al. | 600/567 |
| 2004/0191897 A1 | 9/2004 | Muschler | 435/325 |
| 2004/0210161 A1 | 10/2004 | Burdorff et al. | 600/566 |
| 2004/0215102 A1 | 10/2004 | Ikehara et al. | 600/562 |
| 2004/0220497 A1 | 11/2004 | Findlay et al. | 600/562 |
| 2004/0249389 A1 | 12/2004 | Kim | |
| 2005/0027210 A1 | 2/2005 | Miller | 600/567 |
| 2005/0040060 A1 | 2/2005 | Andersen et al. | 206/363 |
| 2005/0075581 A1 | 4/2005 | Schwindt | 600/568 |
| 2005/0085838 A1 | 4/2005 | Thompson et al. | 606/170 |
| 2005/0101880 A1 | 5/2005 | Cicenas et al. | 600/567 |
| 2005/0113716 A1 | 5/2005 | Mueller, Jr. et al. | 600/568 |
| 2005/0124915 A1 | 6/2005 | Eggers et al. | 600/568 |
| 2005/0148940 A1 | 7/2005 | Miller | 604/187 |
| 2005/0165328 A1 | 7/2005 | Heske et al. | 600/566 |
| 2005/0182394 A1 | 9/2005 | Spero et al. | 606/21 |
| 2005/0200087 A1 | 9/2005 | Vasudeva et al. | 279/143 |
| 2005/0203439 A1 | 9/2005 | Heske et al. | 600/566 |
| 2005/0209530 A1 | 9/2005 | Pflueger | 600/567 |
| 2005/0215921 A1 | 9/2005 | Hibner et al. | 600/566 |
| 2005/0228309 A1 | 10/2005 | Fisher et al. | 600/562 |
| 2006/0011506 A1 | 1/2006 | Riley | 206/570 |
| 2006/0015066 A1 | 1/2006 | Turieo et al. | 604/136 |
| 2006/0052790 A1 | 3/2006 | Miller | 606/80 |
| 2006/0074345 A1 | 4/2006 | Hibner | 600/566 |
| 2006/0079774 A1 | 4/2006 | Anderson | 600/442 |
| 2006/0089565 A1 | 4/2006 | Schramm | 600/568 |
| 2006/0122535 A1 | 6/2006 | Daum | 600/565 |
| 2006/0129082 A1 | 6/2006 | Rozga | 604/6.04 |
| 2006/0144548 A1 | 7/2006 | Beckman et al. | 163/1 |
| 2006/0149163 A1 | 7/2006 | Hibner et al. | 600/566 |
| 2006/0167377 A1 | 7/2006 | Ritchart et al. | 600/566 |
| 2006/0167378 A1 | 7/2006 | Miller | 600/566 |
| 2006/0167379 A1 | 7/2006 | Miller | 600/566 |
| 2006/0184063 A1 | 8/2006 | Miller | 600/568 |
| 2006/0189940 A1 | 8/2006 | Kirsch | 604/164.1 |
| 2007/0149920 A1 | 6/2007 | Michels et al. | 604/93.01 |
| 2007/0213735 A1 | 9/2007 | Sandat et al. | 606/79 |
| 2007/0270775 A1 | 11/2007 | Miller et al. | 604/506 |
| 2008/0015467 A1 | 1/2008 | Miller | 600/568 |
| 2008/0015468 A1 | 1/2008 | Miller | 600/568 |
| 2008/0045857 A1 | 2/2008 | Miller | 600/566 |
| 2008/0140014 A1 | 6/2008 | Miller et al. | 604/180 |
| 2008/0215056 A1 | 9/2008 | Miller et al. | 606/80 |
| 2008/0221580 A1 | 9/2008 | Miller et al. | 606/80 |
| 2011/0186456 A1 | 8/2011 | Bertazzoni et al. | |

FOREIGN PATENT DOCUMENTS

| | | |
|---|---|---|
| CN | 2664675 | 12/2004 |
| DE | 10057931 | 8/2002 |
| EP | 0517000 | 12/1992 |
| EP | 0807412 | 11/1997 |
| EP | 1099450 | 5/2001 |
| EP | 1314452 | 5/2003 |
| FR | 0853349 | 3/1940 |
| FR | 2457105 | 5/1979 |
| FR | 2516386 | 11/1981 |
| GB | 629 824 A | 9/1949 |
| GB | 2130890 | 6/1994 |
| JP | 59-119808 | 8/1984 |
| JP | 61-32663 | 9/1986 |
| JP | 2001-505076 | 4/2001 |
| WO | WO 1992/008410 | 5/1992 |
| WO | WO 1992/08410 | 5/1992 |
| WO | WO 1993/007819 | 4/1993 |
| WO | WO 1996/031164 | 10/1996 |
| WO | WO 1998/006337 | 2/1998 |
| WO | WO 1998/052638 | 11/1998 |
| WO | WO 1998/52638 | 11/1998 |
| WO | WO 1999/018866 | 4/1999 |
| WO | WO 1999/052444 | 10/1999 |
| WO | WO 2000/009024 | 2/2000 |
| WO | WO 2000/09024 | 2/2000 |
| WO | WO 2000/056220 | 9/2000 |
| WO | WO 2002/041792 | 5/2002 |
| WO | WO 2002/096497 | 12/2002 |
| WO | WO 2005/072625 | 8/2005 |
| WO | WO 2005/110259 | 11/2005 |
| WO | WO 2005/112800 | 12/2005 |
| WO | WO 2008/081438 | 7/2008 |

OTHER PUBLICATIONS

Astrom, Acta Radiologica. 36:237-42, 1995.

Astrom, K. Gunnar O., "CT-guided Transsternal Core Biopsy of Anterior Mediastinal Masses," Radiology 1996; 199:564-567. May 1996.

(56) References Cited

OTHER PUBLICATIONS

Astrom, K.G., "Automatic Biopsy Instruments Used Through a Coaxial Bone Biopsy System with an Eccentric Drill Tip," Acta Radiologica, 1995; 36:237-242. May 1995.
Bioaccess.com, Single Use Small Bone Power Tool—How it Works, 1 pg. Printed Jun. 9, 2008.
Buckley et al., CT-guided bone biopsy: Initial experience with commercially available hand held Black and Decker drill, European Journal of Radiology 61, pp. 176-180, 2007.
Communication Pursuant to Article 94(3) EPC in European Application No. 05 712 091.7 dated Apr. 8, 2008.
Communication relating to the results of the partial International Search Report for Mailed PCT/US2005/002484, 6 pages dated May 19, 2005.
Cummings, et al., "ACLS—Principles and Practice" ACLS—The Reference Textbook, American Heart Association, pp. 214-218, 2003.
European Extended Search Report, Application No. EP08021732.6, 7 pages dated Nov. 13, 2009.
European Office Action and Search Report, Application No. 09150973.7, (8 pgs} dated Oct. 23, 2009.
European Office Action Communication, Application No. 08158699.2-1265/1967142, 10 dated Nov. 4, 2008.
European Office Action; Application No. 09 155 111.9-231 0; pp. 3 dated Nov. 25, 2009.
European Search Report 08158699.2-1265, 4 pages dated Aug. 2008.
Extended European Search Report for European application 07842284.7, dated Mar. 16, 2011.
Extended European Search Report for European application 07842285.4, dated Mar. 17, 2011.
Extended European Search Report for European application 07842286.2, dated Mar. 18, 2011.
Extended European Search Report for European application 07842288.8, dated Mar. 16, 2011.
Extended European Search Report in Application No. EP 08021732.6 dated Nov. 13, 2009.
Extended European Search Report in Application No. EP 10153350.3 dated Mar. 11, 2010.
Extended European Search Report in European Application No. 08158699.2 dated Aug. 2008.
F.A.S.T. 1 Intraosseous Infusion System with Depth-Control Mechanism Brochure, 2000.
Gunal, et al., J of Pediatric Surgery. 31(11): 1491-93, 1996.
Hakan et al., CT-guided Bone BiopsyPerformed by Means of Coaxial Bopsy System with an Eccentric Drill, Radiology, pp. 549-552 Aug. 1993.
Hakan, et al., Radiology. 549-52, 1993.
International Preliminary Report on Patent ability in International Application No. PCT/US2005/002484 dated Aug. 3, 2006.
International Preliminary Report on Patentability in International Application No. PCT/US2007/078203, dated Mar. 26, 2009.
International Preliminary Report on Patentability in International Application No. PCT/US2007/072217 dated Feb. 12, 2009.
International Preliminary Report on Patentability in International Application No. PCT/US2007/072202 dated Jan. 15, 2009.
International Preliminary Report on Patentability in International Application No. PCT/US2008/052943 dated Oct. 15, 2009.
International Preliminary Report on Patentability in International Application No. PCT/US/2007/078207, dated Mar. 26, 2009.
International Preliminary Report on Patentability in International Application No. PCT/US/2007/078205, dated Mar. 26, 2009.
International Preliminary Report on Patentability in International Application No. PCT/US/2007/078204, dated Apr. 2, 2009.
International Preliminary Report on Patentability in International Application No. PCT/US/2007/072209, dated May 14, 2009.
International Preliminary Report on Patentability in International Application No. PCT/US/2008/050346, dated Jul. 23, 2009.
Liakat A. Parapia, "Trepanning or trephines: a history of bone marrow biopsy." British J of Haematology. 14-19, 2007.

Michael Trotty, "Technology (A Special Report)—The Wall Street Journal 2008 Technology Innovation Awards—This years winners include: an IV alternative, a better way to make solar panels, a cheap, fuel efficient car and a better way to see in the dark," The Wall Street Journal, Factiva 2008.
Notice of Allowance dated Mar. 29, 2013 in U.S. Appl. No. 11/253,467.
Office Action for Chinese application 200780001188.X with English translation, dated Nov. 9, 2010.
Office Action for Chinese application 200780001198.3, dated Apr. 27, 2010.
Office Action for European application 07842284.7, dated May 3, 2012.
Office Action for European application 07842285.4, dated May 3, 2012.
Office Action for European application 07842286.2, dated Apr. 30, 2012.
Office Action for European application 07842288.8, dated May 3, 2012.
Office Action for U.S. Appl. No. 11/853,685, dated Jun. 24, 2009.
Office Action in Australian Patent Application No. 2003240970 dated Oct. 15, 2007.
Office Action in European Application No. 03756317.8 dated Dec. 28, 2006.
Office Action in European Application No. 08158699.2 dated Nov. 4, 2008.
Office Action in European Application No. EP 03731475.4 dated Oct. 11, 2007.
Office Action in U.S. Appl. No. 11/427,501 dated Aug. 7, 2008.
Office Action in U.S. Appl. No. 10/449,476 dated Oct. 29, 2008.
Office Action issued in Chinese Application No. 200780000590.6 dated Austin 21, 2009.
Office Action issued in Chinese Application No. 200780001198.3 dated Apr. 27, 2010.
Office Action issued in Chinese Application No. 200880000182.5 dated Sep. 10, 2010.
Office Action issued in Chinese Application No. 200910006631.3 dated Mar. 11, 2010.
Office Action issued in Chinese Application No. 200910006631.3, dated Mar. 22, 2011.
Office Action issued in European Application No. 09 155 111.9 dated Nov. 25, 2009.
Office Action issued in European Application No. 09150973.7 dated Oct. 23, 2009.
Office Action w/english translation; Chinese Application No. 200680021872.X; pp. 8 dated Nov. 6, 2009.
Office Action with English translation; Chinese Application No. 200780001190.7; 12 pgs. dated Jun. 2, 2010.
Office Action with English translation; Chinese Application No. 200780001196; 12 pgs. dated Jul. 12, 2010.
Office Action with English translation; Chinese Application No. 200880000182.5; 12 pages, dated Sep. 10, 2010.
Office Action with English translation; Chinese Application No. 200910006631.3; pp. 12 dated Mar. 11, 2010.
Office Action with English translation; Chinese Application No. 200780001198.3; pp. 13 dated Apr. 27, 2010.
Office Action, Chinese Application No. 2005800003261, (with English translation), (9 pgs), dated Jan. 16, 2009.
Office Action, Chinese Application No. 200780000590.6, (with English translation), (13 pgs), dated Aug. 21, 2009.
Office Action, Japanese Application No. 2004-508,669, {with English summary), (9 pgs), dated Aug. 3, 2009.
Office Action, Japanese Application No. 2004-508,670, (with English summary), (13 pgs), dated Apr. 21, 2009.
Office Action, Taiwanese Application No. 94102179 _(with English translation_112 pages, dated May 13, 2010.
Office Action, U.S. Appl. No. 10/449,476, 8 pages dated Oct. 29, 2008.
Official Action for European Application No. 03756317.8 (4 pages) dated Dec. 28, 2006.
PCT Invitation to Pay Additional Fees in International Application No. PCT/US2007/072209 dated Dec. 3, 2007.

(56) References Cited

OTHER PUBLICATIONS

Pediatric Emergency, Intraosseous Infusion for Administration of Fluids and Drugs, www.cookgroup.com/ 2000.
Pediatric Emergency, Intraosseous Infusion for Administration of Fluids and Drugs, www.cookgroup.com, 1 pg 2000.
Pediatrics "2005 American Heart Association Guidelines for Cardiopulmonary Resuscitation and Emergency Cardiovascular Care of Pediatric and Neonatal Patients: Pediatric Advanced Life Support," www.pediatrics.org, Official J of the American Academy of Pediatrics, Feb. 21, 2007.
Pediatrics, 2005 American Heart Association Guidelines for Cardiopulmonary Resuscitation and Emergency Cardiovascular Care of Pediatric and Neonatal Patients: Pediatric Advanced Life Support, Downloaded from www.pediatrics.org Feb. 21, 2007.
Response to Office Action for European application 07842284.7. Filed Nov. 9, 2012.
Response to Office Action for European application 07842285.4. Filed Nov. 13, 2012.
Response to Office Action for European application 07842286.2. Filed Nov. 8, 2012.
Response to Office Action for European application 07842288.8. Filed Nov. 9, 2012.
Response to Official Letter for European application 07842284.7. Filed Oct. 14, 2011.
Response to Official Letter for European application 07842285.4. Filed Oct. 14, 2011.
Response to Official Letter for European application 07842286.2. Filed Oct. 14, 2011.
Response to Official Letter for European application 07842288.8. Filed Oct. 14, 2011.
Richard 0. Cummins et al., "ACLS—Principles and Practice", ACLS—The Reference Textbook, American Heart Association, pp. 214-218, 2003.
Riley et al., "A Pathologist's Perspective on Bone Marrow Aspiration Biopsy: I. Performing a Bone Marrow Examination," Journal of Clinical Laboratory Analysis 18, pp. 70-90, 2004.
Riley, et al., "A Pathologists Perspective on Bone Marrow Aspiration Biopsy: Performing a Bone Marrow Examination" J Clin Lab Analysis. 18:70-90, 2004.
Search Report and Written Opinion in International Application No. PCT/US2007/072202 dated Mar. 25, 2008.
Search Report and Written Opinion in International Application No. PCT/US2007/078207 dated Apr. 7, 2008.
Search Report and Written Opinion in International Application No. PCT/US2007/078205 dated Sep. 11, 2007.
Search Report and Written Opinion in International Application No. PCT/US2007/072217 dated Mar. 31, 2008.
Search Report and Written Opinion in International Application No. PCT/US2007/072209 dated Apr. 25, 2008.
Search Report and Written Opinion in International Application No. PCT/US2006/025201 dated Feb. 7, 2008.
Search Report and Written Opinion in International Application No. PCT/US2008/500346 dated May 22, 2008.
Search Report and Written Opinion in International Application No. PCT/US2007/072209 dated Mar. 12, 2007.
Search Report and Written Opinion in International Application No. PCT/US2007/072217 dated Mar. 12, 2007.
Search Report and Written Opinion in International Application No. PCT/US2006/025201 dated Jan. 29, 2007.
Search Report and Written Opinion in International Application No. PCT/US2003/17167 dated Sep. 16, 2003.
Search Report and Written Opinion in International Application No. PCT/US2003/17203 dated Sep. 16, 2003.
Search Report and Written Opinion in International Application No. PCT/US2004/037753 dated Apr. 19, 2005.
Search Report and Written Opinion in International Application No. PCT/US2004/037743 dated Jul. 8, 2005.
Search Report and Written Opinion in International Application No. PCT/US2005/002484 dated Jul. 22, 2005.
Search Report and Written Opinion in International Application No. PCT/US2007/078203 dated May 13, 2008.
Search Report and Written Opinion in International Application No. PCT/US2007/078204 dated May 15, 2008.
Search Report and Written Opinion in International Application No. PCT/US2008/052943 dated Sep. 26, 2008.
Vidacare Corporation Comments to Intraosseous Vascular Access Position Paper, Infusion Nurses Society, 6 pages. May 4, 2009.
Notice of Allowance dated Mar. 4, 2014 in U.S. Appl. No. 11/253,467.
European Search Report issued in European Patent Application No. 17198059.2 dated Jan. 29, 2018.

* cited by examiner

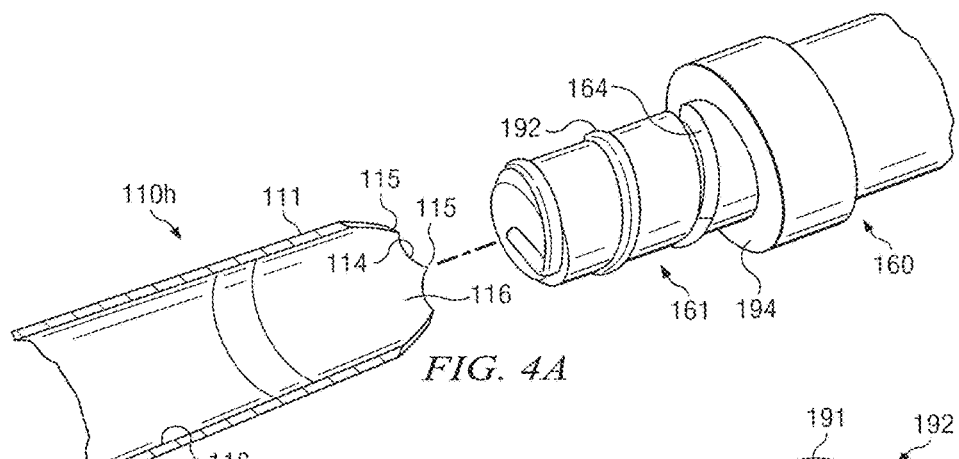
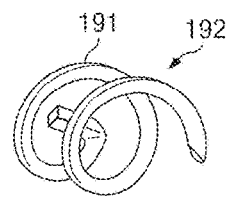
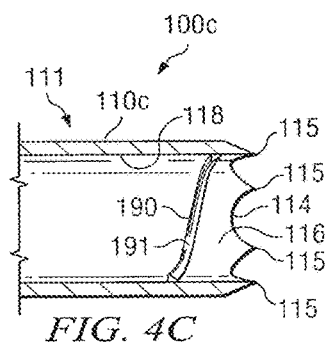
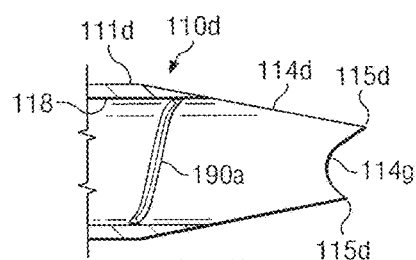
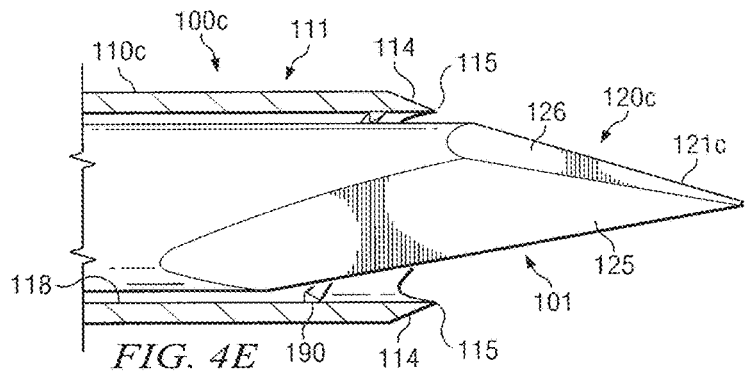

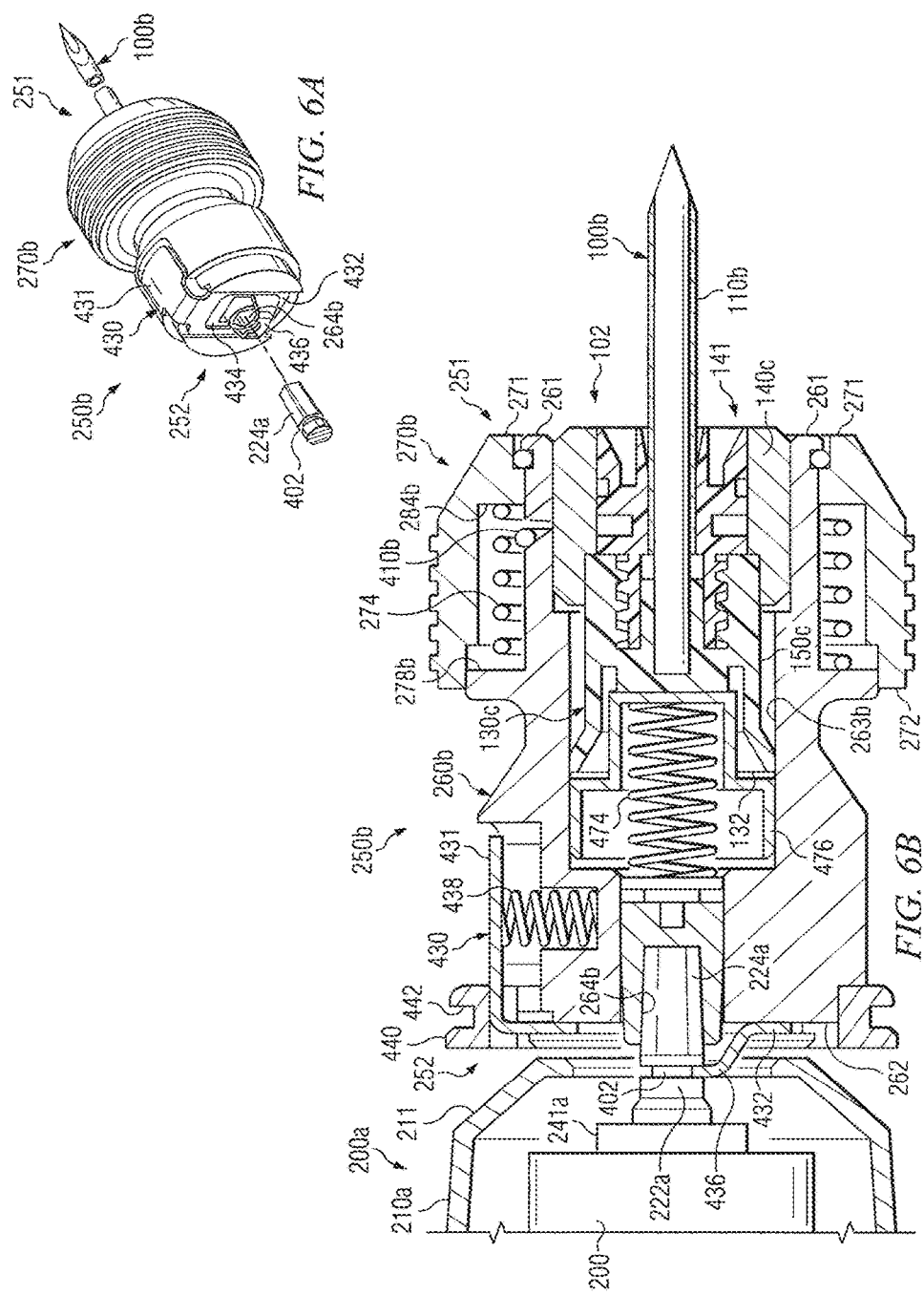

ASSEMBLY FOR COUPLING POWERED DRIVER WITH INTRAOSSEOUS DEVICE

RELATED APPLICATION

This application is a divisional of co-pending application Ser. No. 11/853,678 filed Sep. 11, 2007, which is a continuation-in-part of application Ser. No. 10/449,503 filed May 30, 2003, which claims the benefit of U.S. Provisional Patent Application Ser. No. 60/384,756 filed May 31, 2002. The content of these applications are incorporated herein in their entirety by this reference.

This application claims the benefit of U.S. Provisional Patent Application Ser. No. 60/825,325 entitled "Apparatus and Methods for Biopsy and Aspiration of Bone Marrow" filed Sep. 12, 2006. The contents of this application is incorporated herein in it's entirety by this reference.

This application claims the benefit of U.S. Provisional Patent Application Ser. No. 60/910,122 entitled "Powered Driver Intraosseous Device and Methods To Access Bone Marrow" filed Apr. 4, 2007. The contents of this application is incorporated herein in it's entirety by this reference.

TECHNICAL FIELD

The present disclosure is related generally to medical procedures such as aspiration and biopsy of bone marrow along with apparatus and methods associated with powered drivers, coupler assemblies, aspiration needles, biopsy needles, and associated medical procedure trays and kits.

BACKGROUND OF THE DISCLOSURE

There are many clinical conditions where it is important to access and retrieve bone marrow. In some cases it may be necessary to treat diseases with bone marrow or stem cell transplants to restore functioning blood cells. Such conditions may include, but are not limited to, acute leukemia, brain tumors, breast cancer, Hodgkin's disease, multiple myeloma, neuroblastoma, non-Hodgkin's lymphomas, ovarian cancer, sarcoma and testicular cancer. In other cases it is necessary to access bone marrow to obtain a sample or specimen of the marrow for diagnostic testing. These conditions may include, but are not limited to, cancers of any type and hematologic disease of any origin.

Gaining access to bone and associated bone marrow for a small biopsy specimen or aspiration of a larger quantity of bone marrow may be difficult, traumatic and occasionally dangerous, depending on each selected target area for harvesting bone and/or associated bone marrow, operator expertise and patient anatomy. Currently available devices and techniques for gaining access to a bone and associated bone marrow may include an intraosseous (IO) needle with a removable trocar disposed therein. Various shapes and sizes of handles may be used to apply manual pressure and to manually rotate the IO needle and removable trocar as a set. Such manual IO devices often require substantial force to break through the outer cortex of a bone. Exertion of such force may cause pain to a patient and may sometimes damage the bone and/or IO device. Such force may cause damage when harvesting bone marrow from children with softer bone structures or any patient with bones deteriorated by disease (cancer).

Occasionally a core specimen of bone and/or bone marrow may not be successfully retrieved using a standard biopsy needle. Thus, multiple insertions at different sites may be necessary to obtain a satisfactory bone and/or bone marrow biopsy specimen. Risks to health care personnel may be higher because of increased handling of blood contaminated sharp instruments. Accidental needle sticks and missed target areas may further complicate procedures and increase risks to health care personnel and/or patients.

Conventional bone marrow transplant techniques may require multiple penetration sites (up to 20 per patient) in order to obtain enough bone marrow to perform a routine bone marrow transplant. This procedure is often labor intensive. Conventional biopsy needles and/or aspiration needles are typically inserted with considerable manual force. This force may cause loss of control or operator fatigue. When the biopsy needle or aspiration needle is in place, an associated trocar is generally removed and a syringe attached to one end of the needle to aspirate a few cubic centimeters of bone marrow. The biopsy or aspiration needle is then withdrawn. A new insertion site may be penetrated, often about a centimeter from the first insertion site. The procedure may be repeated multiple times.

SUMMARY OF THE DISCLOSURE

In accordance with teachings of the present disclosure, apparatus and methods are provided for aspiration and/or biopsy of bone marrow. Such apparatus and methods may also be used during various types of stem cell transplant procedures. Various teaching of the present disclosure may be used with other types of intraosseous devices and other types of medical procedures outside the field of providing vascular access for treatment of a patient. Examples of such procedures may include, but are not limited to, kyphoplasty, vertebral plasty, placement of wires and screws associated with replacement of joints and internal fixation of bone fractures and many other orthopedic procedures. Teachings of the present disclosure may also be incorporated into various gastroenterology-urology biopsy devices and procedures.

One aspect of the present disclosure may include a bone marrow aspiration system having an aspiration needle set along with a powered driver and coupler assembly operable to insert the aspiration needle set into a bone and associated bone marrow. The aspiration needle set may include a cannula having a single lumen and a trocar or stylet operable to be slidably disposed within the lumen of the cannula. Various types of connections including, but not limited to, Luer lock connections may be used to releasably engage the trocar within the cannula.

Another aspect of the present disclosure may include a bone and/or bone marrow biopsy system having a biopsy needle or biopsy needle set along with a powered driver or a manual driver. The powered driver and a coupler assembly may be used to insert the biopsy needle or biopsy needle set into a bone and associated bone marrow. The biopsy needle set may include a cannula having a single lumen and a trocar operable to be slidably or releasably disposed within the lumen of the cannula. Such needles and needle sets may be used in connection with detection and/or treatment of various cancers and other disease indications.

Still another aspect of the present disclosure may include accessing bone marrow by inserting an intraosseous needle or needle set into a bone and associated bone marrow using a powered driver and coupler assembly operable to rotate the intraosseous needle or needle set at an optimum speed to obtain a biopsy specimen of the bone and/or associated bone marrow. A single helical thread may be provided in one end of a biopsy needle to enhance capture of a biopsy specimen by screwing the single helical thread into associate cancellous bone to capture a bone marrow specimen or bone marrow core.

One aspect of the present disclosure may include placing a powered driver within a containment bag or sterile enclosure to provide isolation between the powered driver and an exterior environment. The containment bag may be formed from relatively flexible, lightweight, clear plastic-type materials. The containment bag may include a port assembly operable to be releasably engaged with one end of the powered driver and to maintain a fluid barrier with adjacent portions of a driver housing. An intraosseous device may be attached to one end of the port assembly. A drive shaft extending from the powered driver may be releasably engage with another end of the port assembly.

A further aspect of the present disclosure may include a biopsy kit having a biopsy needle and an ejector or ejector rod operable to remove a bone and/or bone marrow specimen from a biopsy needle. A funnel (sometimes referred to as an "ejector funnel") may also be included within the biopsy kit. The funnel may accommodate insertion of the ejector into one end of the biopsy needle. The funnel may include a reduced inside diameter portion formed in accordance with teachings of the present disclosure. For some embodiments, interior portions of the funnel may function as a "one way connector" which may allow the funnel to function as a sharps protector for one end of the biopsy needle disposed therein.

A further aspect of the present disclosure may include a coupler assembly operable to releasably engage an intraosseous device with portions of a drive shaft extending from one end of a powered driver. The coupler assembly may allow the powered driver to insert the intraosseous device at an insertion site (power in.) The coupler assembly may also allow the powered driver to "spin" the intraosseous device during removal from the insertion site (power out). This feature of the present disclosure may also be referred to as "power in and power out."

Apparatus and methods incorporating teachings of the present disclosure may:

Reduced physical requirements to insert an IO device into bone and associated bone marrow.

Better control of an IO device during insertion.

Increased speed to complete an IO procedure.

Reduced discomfort to patients.

Simple, intuitive systems and procedures for an operator.

This summary contains only a limited number of examples of various embodiments and features of the present disclosure. Additional examples of embodiments and features will be discussed in the Detailed Description of the Disclosure.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 4A is a schematic drawing partially in section and partially in elevation with portions broken away showing an exploded isometric view of a mandrel operable to install a thread insert within portions of a biopsy needle in accordance with teachings of the present disclosure;

FIG. 4B is a schematic drawing showing one example of a thread insert which may be disposed within the longitudinal bore of a biopsy needle in accordance with teachings of the present disclosure;

FIG. 4C is a schematic drawing in section with portions broken away showing one example of a biopsy needle with a single helical thread disposed within one end of the biopsy needle incorporating teachings of the present disclosure;

FIG. 4D is a schematic drawing in section with portions broken away showing another example of a biopsy needle with a single helical thread disposed within one end of the biopsy needle in accordance with teachings of the present disclosure;

FIG. 4E is a schematic drawing in section and in elevation with portions broken away showing a biopsy needle set including a trocar and a single helical thread disposed proximate one end of a generally hollow cannula in accordance with teachings of the present disclosure;

FIG. 6A is a schematic drawing showing an alternative embodiment of a coupler assembly operable to releasably engage an intraosseous device with one end of a drive shaft extending from a powered driver in accordance with teachings of the present disclosure;

FIG. 6B is a schematic drawing in section with portions broken away showing portions of the powered driver, coupler assembly and intraosseous device of FIG. 6A;

DETAILED DESCRIPTION OF THE DISCLOSURE

Figure 1A:
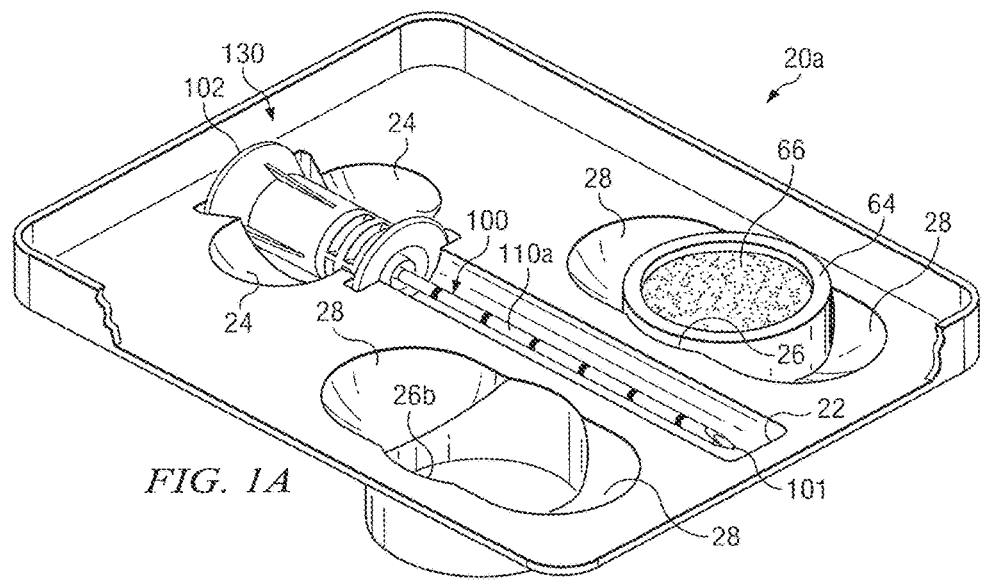
FIG. 1A is a schematic drawing showing an isometric view of one example of a aspiration needle set incorporating teachings of the present disclosure disposed in a kit.

Preferred embodiments of the disclosure and various advantages may be understood by reference to FIGS. 1A-10, wherein like numbers refer to same and like parts.

The term "containment bag" as used in this application may include any sterile sleeve, sterile envelope, sterile glove, sterile enclosure or any other device incorporating teachings of the present disclosure and operable to allow engaging a non-sterile device with a sterile device and conducting a medical procedure requiring a sterile field or sterile environment.

For some applications a non-sterile powered driver may be placed in a containment bag incorporating teachings of the present disclosure and engaged with a sterile intraosseous device for use during various medical procedures requiring a sterile field or sterile environment. Such containment bags may be attached to a coupler assembly or any other device incorporating teachings of the present disclosure to prevent the non-sterile powered driver from contaminating the sterile intraosseous (IO) device during and after engagement of the non-sterile powered driver with the IO device.

The term "driver" as used in this application may include any type of powered driver satisfactory for inserting an intraosseous (IO) device into a selected portion of a patient's vascular system. Such powered drivers often rotate a drive shaft extending therefrom. However, various teachings of the present disclosure may be used with powered drivers that reciprocate an associated drive shaft (not expressly shown).

Various techniques may be satisfactorily used to releasably engage or attach an IO device with a powered driver in accordance with teachings of the present disclosure. For example a wide variety of coupler assemblies, port assemblies, connectors, receptacles, fittings, hubs, hub assemblies, latching mechanisms and/or other types of connecting devices incorporating teachings of the present disclosure may be satisfactorily used to releasably engage an IO device with a powered driver.

Various types of coupler assemblies incorporating teachings of the present disclosure may be satisfactorily used to releasably engage one end of a shaft extending from a driver with one end of an intraosseous device. For some embodiments the powered driver may include a drive shaft having one end with a generally hexagonal cross section operable to be releasably engaged with a latch mechanism disposed in one end of a coupler assembly. For some embodiments a coupler assembly incorporating teachings of the present disclosure may be referred to as a "hands free" coupler, a quick disconnect or quick release coupler and/or port assembly.

Respective latch mechanisms may be disposed proximate a first end and a second end of a coupler assembly in accordance with teachings of the present disclosure. Pushing one end of a drive shaft extending from a powered driver into the second end of the coupler assembly may result in an annular recess disposed in the one end of the drive shaft "snapping" into releasable engagement with the respective latch mechanism. Pushing one end of an intraosseous device into the first end of the coupler assembly may result in an annular recess in the one end of the intraosseous device "snapping" into releasable engagement with the respective latch mechanism.

For some embodiments, a coupler assembly or port assembly may be engaged with a containment bag or sterile sleeve in accordance with teachings of the present disclosure. Coupler assemblies and/or hub assemblies incorporating teachings of the present disclosure allow easy separation of an associated powered driver from an IO device such that the IO device may remain in place in a patient to allow bone marrow aspiration or removal of bone and/or bone marrow biopsy specimens. Such coupler assemblies and/or port assemblies may also allow an associated powered driver to "spin" or rotate an attached IO device while withdrawing an IO device from an insertion site or changing the depth of penetration of an IO device in a target area. Rotating the IO device during withdrawal or changing depth (power out) may substantially improve patient comfort and reduce potential trauma to bone and soft body tissue proximate an insertion site.

A powered driver may be used to insert an IO device incorporating teachings of the present disclosure into a selected target area or target site in ten seconds or less. However, various teachings of the present disclosure are not limited to use with powered drivers. Manual drivers and spring powered drivers may also be used with IO devices incorporating teachings of the present disclosure.

Examples of manual drivers are shown in co-pending patent application Ser. No. 11/042,912 entitled Manual Intraosseous Device filed Jan. 25, 2005 (now U.S. Pat. No. 8,641,715.

The term "fluid" may be used in this application to include liquids such as, but not limited to, blood, water, saline solutions, IV solutions, plasma or any mixture of liquids, particulate matter, dissolved medication and/or drugs associated with biopsy or aspiration of bone marrow or communication of fluids with bone marrow or other target sites. The term "fluid" may also be used in this patent application to include any body fluids and/or liquids containing particulate matter such as bone marrow and/or cells which may be withdrawn from a target area.

The terms "harvest" and "harvesting" may be used in this application to include bone and/or bone marrow biopsy and bone marrow aspiration. Bone and/or bone marrow biopsy (sometimes referred to as "needle biopsy") may be generally described as removing a relatively small piece or specimen of bone and/or bone marrow from a selected target area for biopsy purposes. Bone marrow aspiration (sometimes referred to as "bone marrow sampling") may be generally described as removing larger quantities of bone marrow from a selected target area. Relatively large quantities of bone marrow may be used for diagnostic, transplantation and/or research purposes. For example some stem cell research techniques may require relatively large quantities of bone marrow.

The terms "insertion site," "penetration site," and "installation site" may be used in this application to describe a location on a bone at which an intraosseous device may be inserted or drilled into the bone and associated bone marrow. Insertion sites, penetration sites and installation sites are generally covered by skin and soft tissue.

The term "intraosseous (IO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, IO needle set, biopsy needle set or aspiration needle set operable to provide access to an intraosseous space or interior portions of a bone. Such TO devices may be formed, at least in part, from metal alloys such as 304 stainless steel and other biocompatible materials associated with needles and similar medical devices.

Various types of IO devices may be formed in accordance with teachings of the present disclosure. Examples of such IO devices may include, but are not limited to, biopsy needles, biopsy needle sets, aspiration needles and aspiration needle sets. However, a wide variety of other IO devices may be formed in accordance with one or more teachings of the present disclosure. Such TO devices may or may not include a trocar or stylet.

For some applications, a trocar or stylet may be inserted into a generally hollow, longitudinal bore or lumen in an associated catheter or cannula. The first end of the second hub may be releasably engaged with second end of the first hub to releasably dispose the stylet or trocar within the longitudinal bore of the cannula or catheter. The present disclosure is not limited to aspiration needle sets 100 or biopsy needle sets 100a as discussed in this application.

The term "target area" may be used in this application to describe selected portions of a bone cavity or locations in a bone cavity from which associated bone marrow may be harvested in accordance with teachings of the present disclosure.

Many currently available techniques for harvesting bone and/or bone marrow may require more than one penetration into a bone and associated bone marrow to retrieve an adequate sample of bone and/or bone marrow. Multiple penetration sites may be required in the same bone if a biopsy specimen is not satisfactorily retrieved at the first penetration site. Medical personnel may need to insert an IO needle into several different penetration sites on the same bone to obtain adequate quantities of bone marrow for transplant or stem cell research. For example obtaining sufficient quantities of bone marrow from a patient's pelvis may require six or more insertion sites. Multiple insertions may be extremely painful for a patient and may deter some people from donating bone marrow. Multiple insertions may also cause fatigue in medical personnel performing such procedures with manual IO devices.

Bone marrow transplant procedures and various research procedures such as stem cell research often require relatively large quantities of bone and/or bone marrow. Hip bones generally have a large bone cavity and are therefore frequently used as a target area for harvesting bone marrow for transplant procedures, stem cell research procedures or any other procedure requiring relatively large quantities of bone marrow.

For some applications, an IO needle or other IO device may be formed with a first end operable to penetrate bone and/or associated bone marrow. A connector or hub may be attached to a second end of the IO needle or other IO device. Such connectors or hubs may be operable to releasably engage the IO needle or IO device with a powered driver, a manual driver and/or a coupler assembly.

IO needle sets and other IO devices incorporating teachings of the present disclosure may include a first IO device such as a cannula, catheter or outer penetrator and a second IO device such as a stylet, trocar or inner penetrator. Various types of cutting surfaces may be formed proximate a first end of the first IO device and a first end of the second IO device. The cutting surface of the first IO device and the cutting surface of the second IO device may cooperate with each other to penetrate bone and/or associated bone marrow.

A first connector or first hub may be used to releasably engage the first IO needle or IO device with the second IO needle or IO device. For example an IO needle set may include a first connector or a first hub with a generally hollow cannula, catheter or outer penetrator attached thereto and extending from a first end of the first hub. A second end of the first hub may be operable to be releasably engaged with a first end of a second connector or a second hub. A stylet, trocar or inner penetrator may also be attached to and extend from the first end of the second hub. The second end of the first hub may include an opening sized to allow inserting the stylet, trocar or inner penetrator through the opening and a lumen in the cannula, catheter or outer penetrator.

A second end of the second hub may be operable to be releasably engaged with a first end of a coupler assembly incorporating teachings of the present disclosure. One end of a shaft extending from a powered driver or a manual driver may be releasably engaged with a second end of the coupler assembly.

Additional details concerning powered drivers, connectors, hubs, and IO devices may be found in copending patent application entitled "Powered Driver Intraosseous Device and Methods To Access Bone Marrow" filed Apr. 3, 2008 Ser. No. 12/061,944 (now U.S. Pat. No. 9,451,968) which claims priority from a provisional patent application with the same title filed on Apr. 4, 2007.

Various features of the present disclosure may be described with respect to powered driver 200, coupler assemblies 250, 250a, 250b and 250c, hub assemblies 130, 130a, 130b and 130c, IO needle sets 100, 100a and 100b, biopsy needle 100c and/or containment bag 170. However, the present disclosure is not limited to such powered drivers, coupler assemblies, hub assemblies, IO needle sets, biopsy needles and/or containment bags. A wide variety of intraosseous devices, hub assemblies, coupler assemblies and/or containment bags may be formed in accordance with teachings of the present disclosure with various dimensions and/or configurations.

Figure 1B:
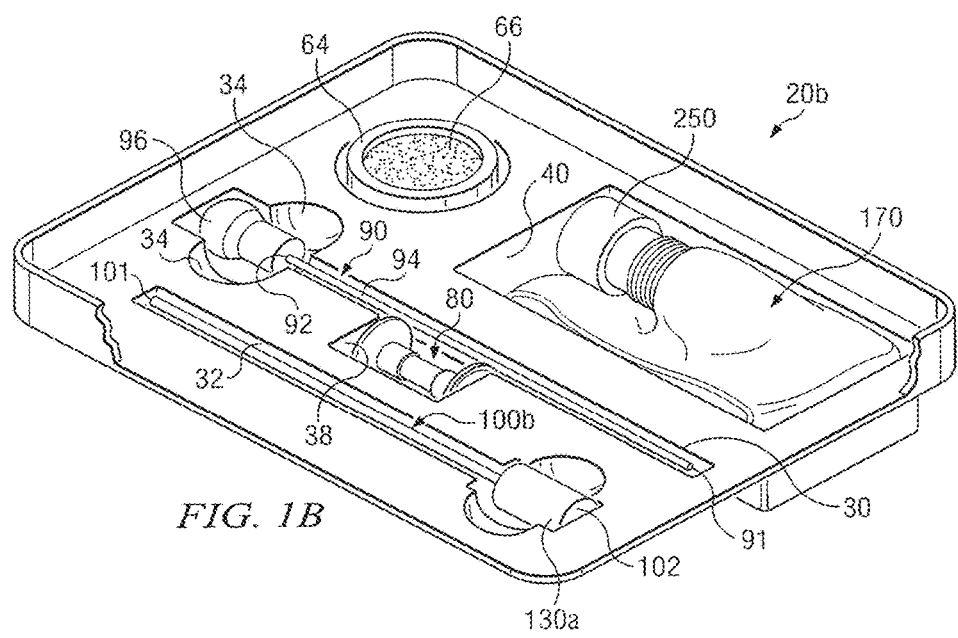
FIG. 1B is a schematic drawing showing an isometric view of one example of a biopsy needle set incorporating teachings of the present disclosure disposed in a kit.

FIGS. 1A-1J show some examples of medical procedure trays and/or kits which may contain one or more intraosseous devices and/or other components incorporating teachings of the present disclosure. For example, medical procedure tray 20a as shown in FIG. 1A may include intraosseous needle set or aspiration needle set 100 incorporating various teachings of the present disclosure. Medical procedure tray 20b as shown in FIG. 1B may include intraosseous needle set or biopsy needle set 100b, ejector 90, funnel 80 and/or containment bag or sterile sleeve 170. Medical procedure tray 20c as shown in FIGS. 1C-1I may also include various IO devices and other components incorporating teachings of the present disclosure including, but not limited to, biopsy needle set 100b, coupler assembly 250, containment bag 170, ejector 90 and/or funnel 80a.

Medical procedure trays and/or kits formed in accordance with teachings of the present disclosure may provide a support or base for various components such as a coupler assembly, funnel and/or sharps protector to allow an operator or user to perform various functions without requiring that the operator or user hold or manipulate the respective component. For example medical procedure tray 20c as shown in FIG. 1 may position and support coupler assembly 250 such that one end of a powered driver may be inserted (pushed) into releasable engagement with second end 252 of coupler assembly 250. The powered driver may then be used to withdraw coupler assembly 250 from medical procedure tray 20c without requiring an operator or user to directly hold or manipulate coupler assembly 250.

Funnel 80a may be positioned and supported within medical procedure tray 20c such that one end of an intraosseous device may be inserted (pushed) into funnel 80a. Funnel 80a may be withdrawn from medical procedure tray 20c without requiring that an operator or user directly hold or manipulate funnel 80a. Each sharps protector 64a may also be positioned and supported within medical procedure tray 20c to allow inserting (pushing) one end of an intraosseous device or any other medical device requiring sharps protection into sharps protector 64a without requiring that an operator or user to directly hold or manipulate the associated sharps protector 64a. Medical procedure trays, coupler assemblies and other components formed in accordance with teachings of the present disclosure may substantially reduce the number of opportunities for an accidental "needle stick" and/or dropping, contaminating or other problems associated with handling and manipulating various components disposed within an associated medical procedure tray.

Medical procedure trays and kits formed in accordance with teachings of the present disclosure may have a wide variety of configurations and/or dimensions. For some applications, a kit holding intraosseous devices in accordance with teachings of the present disclosure may have an overall length of approximately four and one-half inches, a width of approximately three inches and a depth of approximately two inches. Various heat sealing techniques may be satisfactorily used to place a removable cover (not expressly shown) over a medical procedure tray or kit incorporating teachings of the present disclosure.

Figure 1C:
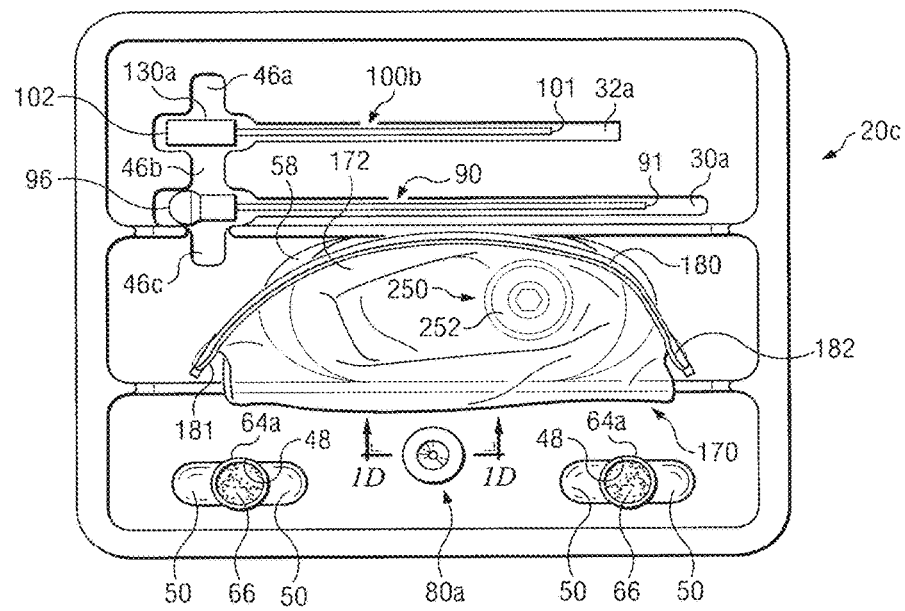
FIG. 1C is a schematic drawing showing an isometric view of one example of a medical procedure tray including a biopsy needle set and other components satisfactory for use with a powered driver in a sterile environment in accordance with teachings of the present disclosure.
Figure 1D:
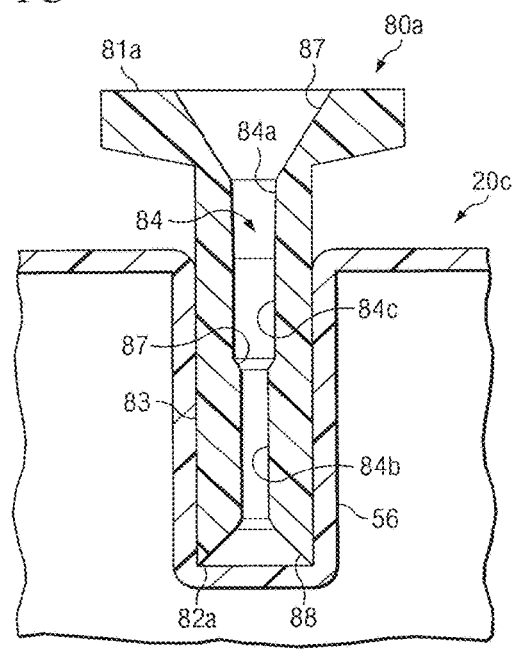
FIG. 1D is a drawing in section taken along lines 1D-1D of FIG. 1C.
Figure 1E:
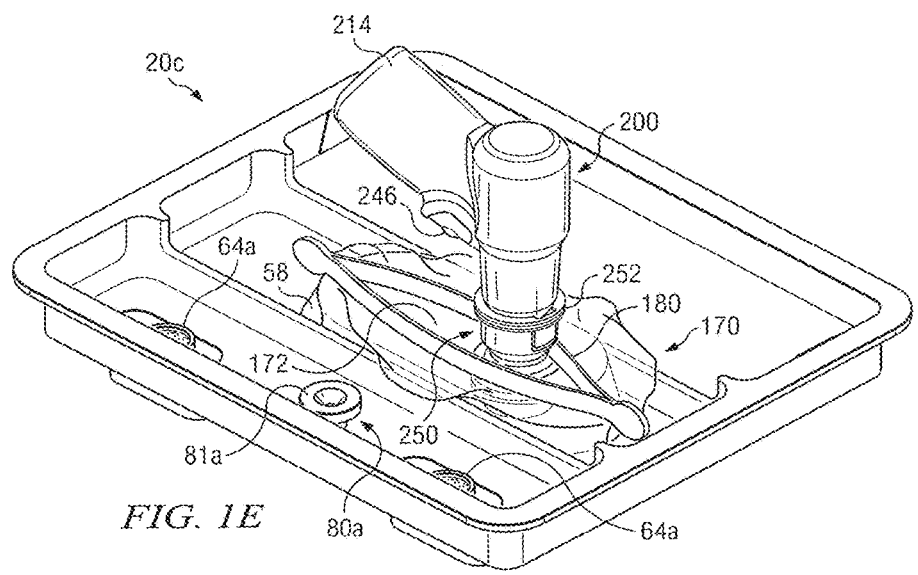
FIG. 1E is a schematic drawing showing an isometric view of the medical procedure tray of FIG. 1D with a non-sterile medical device disposed in a containment bag in accordance with teachings of the present disclosure.
Figure 1F:
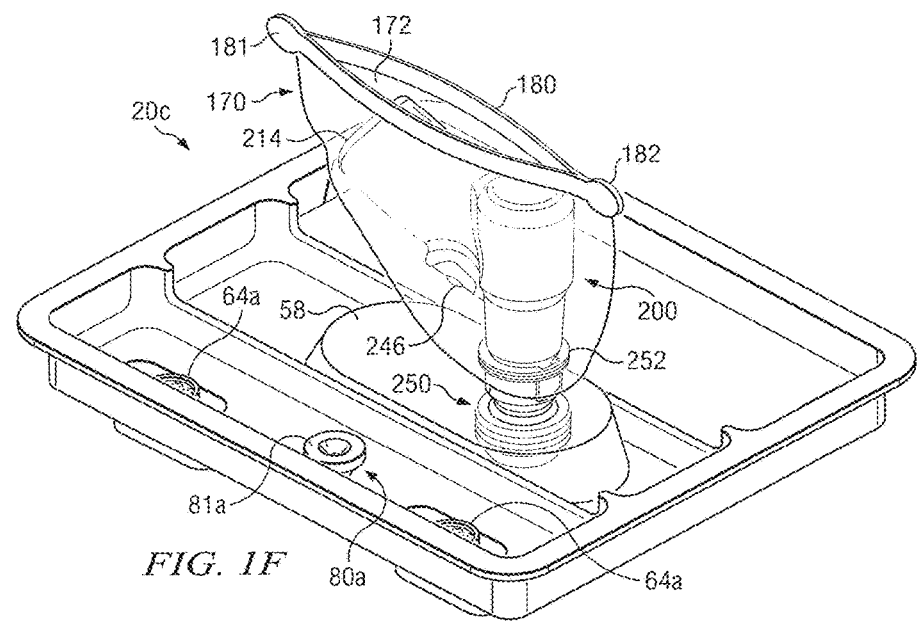
FIG. 1F is a schematic drawing showing still another isometric view of the medical procedure tray of FIG. 1D with the non-sterile medical device disposed in the containment bag in accordance with teachings of the present disclosure.

Medical procedure trays 20a, 20b and/or 20c may also contain a wide variety of other components including, but not limited to, one or more sharps protectors 64 as shown in FIGS. 1A and 1B or sharps protectors 64a as shown in FIGS. 1C, 1E and 1F. Sharps protectors 64 and 64a may include hard foam or claylike material 66 disposed therein. Intraosseous devices such as aspiration needle sets and biopsy needle sets typically have respective sharp tips and/or cutting surface operable to penetrate skin, soft tissue and bone. The sharp tips and/or cutting surface of such intraosseous devices may be inserted into hard foam or claylike material 66 after completion of a medical procedure using the respective intraosseous device.

For some applications, medical procedure tray 20a may be referred to as a "bone marrow aspiration tray," "aspiration procedure tray" or "bone marrow aspiration kit". For some applications, medical procedure trays 20b and 20c may sometimes be referred to as "bone and/or bone marrow biopsy procedure trays" or "biopsy procedure trays" or "bone marrow biopsy kits."

Medical procedure trays 20a, 20b and/or 20c may be formed from various polymeric materials compatible with sterile packaging and storage of various components disposed within each medical procedure tray. For some applications ethylene oxide sterilization techniques may be used during assembly and packaging of medical procedure trays 20a, 20b and 20c. However, other sterilization procedures may be used as appropriate.

Respective covers (not expressly shown) may be placed over each medical procedure tray 20a, 20b and 20c as part of an associated sterilization and packaging process. Such covers may be removed prior to use of various components disposed within each medical procedure tray.

Medical procedure tray or aspiration tray 20a (see FIG. 1A) may include elongated slot 22 with appropriate dimensions for an associated intraosseous device such as, but not limited to, aspiration needle set 100. The dimensions and configuration of slot 22 may be selected to accommodate the combined length of hub assembly 130 and cannula 110a extending therefrom. One end of slot 22 may be sized to accommodate the dimensions and configuration of hub assembly 130. Enlarged openings or finger slots 24 may also be provided to accommodate inserting and removing aspiration needle set 100 from slot 22. Various details associated with aspiration needle set 100 will be discussed later with respect to FIG. 3A.

Sharps protector 64 may be disposed within holder 26 of medical procedure tray 20a. A pair of finger slots 28 may also be formed in tray 20a to accommodate inserting and removing sharps protector 64 from holder 26a. Holder 26b may also be formed in tray 20a along with associated finger slots 28. An additional sharps protector or other components may be disposed within holder 26b. The dimensions/configurations of slot 22 and holders 26a and 26b may be varied as desired for respective components which will be disposed therein.

Medical procedure tray or biopsy tray 20b (See FIG. 1B) may include elongated slots 30 and 32. The dimensions and configuration of elongated slot 30 may be selected to accommodate placing ejector 90 therein. The dimensions and configuration of elongated slot 32 may be selected to accommodate placing intraosseous device or biopsy needle set 100b therein.

One end of elongated slot 30 may have configuration and dimensions selected to accommodate the configuration and dimensions of handle 96 disposed on second end 92 of injector rod 94. A pair of finger slots 34 may be formed as part of elongated slot 30 to allow installing and removing ejector 90. One end of elongated slot 32 may be operable to accommodate the configuration and dimensions associated with hub assembly 130a of biopsy needle set 100b. A pair of finger slots 36 may also be provided as part of elongated slot 32 to accommodate inserting and removing biopsy needle set 100b from elongated slot 32.

Tray 20b may also include holder 38 disposed adjacent to elongated slot 30. Holder 38 may have a configuration and dimensions compatible with releasably placing funnel 80 therein. Tray 20b may also include compartment or holder 40 with dimensions compatible with placing containment bag 170 with coupler assembly 250 attached thereto. One or more specimen or sample containers or cups (not expressly shown) may be provided in biopsy tray 20b. Biopsy specimen or sample containers may include a cavity sized to receive a biopsy specimen from biopsy needle set 100b. Funnel holders 38 may be formed in biopsy procedure tray 20b adjacent to ejector 90 to ensure that funnel 80 is readily available to assist with removing a biopsy specimen from biopsy needle set 100b.

Medical procedure tray or biopsy tray 20c as shown in FIGS. 1C-1I represents another example of a medical procedure tray formed in accordance with teachings of the present disclosure. Biopsy procedure tray 20c may include intraosseous device or biopsy needle set 100b releasably disposed in elongated slot 42 and ejector 90 disposed in elongated slot 44. Respective ends of elongated slots 42 and 44 may be disposed adjacent to each other so that finger slots 46a, 46b and 46c may be more easily manufactured. Biopsy procedure tray 20c also includes a pair of sharps protectors 64a disposed in respective holders 48. Each holder 48 includes a pair of finger slots 50.

Funnel 80a may be slidably disposed in holder 56 in medical procedure tray 20c in a generally vertical position. See FIG. 1D. As a result, first end 81a of funnel 80a may be oriented in a position to allow inserting one end of biopsy needle set 100b or outer cannula 110b therein. Longitudinal passageway 84 proximate first end 81a may include a sticking tapered portion operable to maintain contact with one end of biopsy needle set 100b or outer cannula 110b. Biopsy needle set 100b or cannula 110b may then be manipulated to pull funnel 80a from holder 56. Funnel 80a may serve as a sharps protector for the one end of an intraosseous device inserted therein.

One of the benefits of the present disclosure may include being able to releasably engage one end of a powered driver with one end of a coupler assembly, releasably engage one end of a biopsy needle with an opposite end of the coupler assembly, insert another end of the biopsy needle into a selected target area, "power out" the biopsy needle with a high degree of confidence that a biopsy specimen will be disposed therein and insert the other end of the biopsy needle into a funnel to provide both sharps protection and removal of the biopsy specimen. Any direct contact between an operator and the biopsy needle may be limited to pushing the one end of the biopsy needle into a respective end of the coupler assembly.

A pair of holders or clamps (not expressly shown) may also be formed in medical procedure tray 20c adjacent to holder for coupler assembly 250. Such clamps may be designed to accommodate first end 181 and second end 182 of flexible stay 180 disposed on second opening 172 of containment bag 170. Coupler assembly 250 may also be installed in holder 58 of biopsy procedure tray 20c with first end 251 down and second end 252 looking up.

FIGS. 1E and 1F show one procedure for placing a powered driver within a containment bag incorporating teachings of the present disclosure. Containment bag 170 may be formed from generally flexible, fluid impervious material which may also be sterilized using conventional sterilization techniques. Containment bag 170 may be used to prevent a non-sterile powered driver from contaminating a sterile intraosseous device and/or an injection site, particularly during a bone marrow biopsy procedure or a bone marrow aspiration procedure. Containment bag 170 may be operable to form a fluid barrier with adjacent portions of housing assembly 270. At the same time, coupler assembly 250 may allow powered driver to rotate an intraosseous device releasably engaged with first end 251 of coupler assembly 250 without damage to containment bag 170.

First opening 171 may be formed along one edge of containment bag or sleeve 170. Second opening 172 may be formed along an opposite edge of containment bag 170. The configuration and dimensions of second opening 172 may be selected to accommodate inserting and removing a powered driver or other non-sterile medical device therefrom.

Coupler assembly 250 may be securely engaged with and extend from first opening 171. The attachment between adjacent portions of first opening 171 and coupler assembly 250 may be selected to allow rotation of an intraosseous device by an associated powered drive. Housing assembly 270 and/or housing segments 280 and 290 of coupler assembly 250 may remain relatively stationary during rotation of elongated core 260. See FIG. 5F. For example portions of housing assembly 270 such as flange 254 extending from second end 252 of coupler assembly 250 may be attached to first opening 171 and remain relatively stationary while powered driver 200 rotates elongated core 260 and aspiration needle set 100 extending therefrom.

For some applications, powered driver 200 may be directly placed into a containment bag and engaged with coupler assembly 250. For other applications, a non-sterile powered driver may be inserted into containment bag 170 in connection with removing coupler assembly 250 from a medical procedure tray.

For some applications, a protective cover (not expressly shown) may be removed from medical procedure tray 20c. End 224 extending from drive shaft 222 of powered driver 200 may then be inserted through second opening 172 of containment bag 170 and releasably engaged with second end 252 of coupler assembly 250.

First end 181 and second end 182 of flexible stay 180 may then be removed from respective clamps or holders in medical procedure tray 20c to allow manually lifting second opening 172 upwardly relative to powered driver 200. See FIG. 1E. Containment bag 170 may continue to be raised to a fully extended position with powered driver 200 disposed therein. See FIG. 1F. Flap 174 may then be placed over second opening 172. Containment bag 170 with powered driver 200 disposed therein and coupler assembly 250 may then be removed from holder 58 of medical procedure tray 20c.

FIGS. 1G-1J show another procedure incorporating teachings of the present disclosure to place a non-sterile powered driver into a containment bag with a coupler assembly or port assembly extending therefrom and enclosing the non-sterile powered driver within the containment bag to allow engaging the coupler assembly with a sterile intraosseous device. The same procedure may be used to engage other non-sterile medical devices with sterile medical devices.

For some applications, medical procedure tray 20c may be placed in second tray 20d with first drape 51 disposed therebetween. See FIGS. 1G and 1J. Second drape 52 with opening or fenestration 54 may then be placed over medical procedure tray 20c with opening or fenestration 54 generally aligned with second opening 172 of containment bag 170 and second end 252 of coupler assembly 250. Second drape 52 may also cover portions of first drape 51 extending outwardly from between medical procedure tray 20c and the second medical procedure tray (not expressly shown).

For some applications portions of second drape 52 adjacent to fenestration 54 may be releasably engaged with portions of containment bag 170 adjacent to second opening 172. See FIG. 1J. Various commercially available low strength adhesive materials may be satisfactorily used to provide releasable engagement between second drape 52 proximate fenestration 54 and second opening 172 of containment bag 170.

Figure 1G:
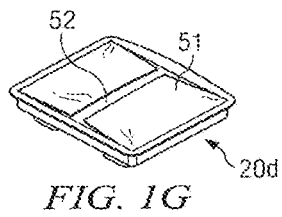
FIG. 1G is a schematic drawing showing a further isometric view of the medical procedure tray of FIG. 1C.

First drape 51 and second drape 52 may then be folded with each other and covering the contents of medical procedure tray 20c such as shown in FIG. 1G. A portion of second drape 52 may be seen in FIG. 1G between respective portions of first drape 51.

A protective cover (not expressly shown) may then be placed over both medical procedure trays and any exposed portions of drapes 51 and 52. The combined medical procedure tray (not expressly shown) may then be sterilized. One benefit of such sterilization include, but is not limited to, providing a sterilized containment bag which may be used to engage a non-sterile medical device with a sterile medical device in accordance with teachings of the present disclosure.

Figure 1H:
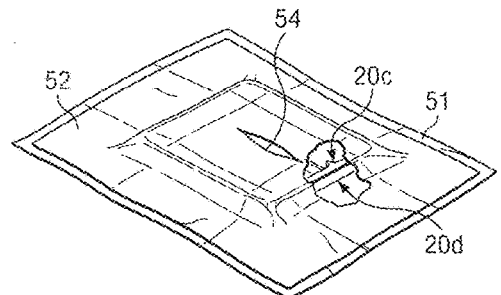
FIG. 1H is a schematic drawing showing an isometric view of the medical procedure tray of FIG. 1G after unfolding a first drape and a second drape.
Figure 1I:
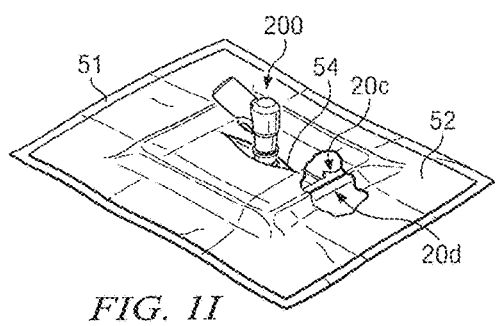
FIG. 1I is a schematic drawing showing an isometric view of the medical procedure tray of FIG. 1G after a powered driver has been engaged with a coupler assembly in accordance with teachings of the present disclosure.
Figure 1J:
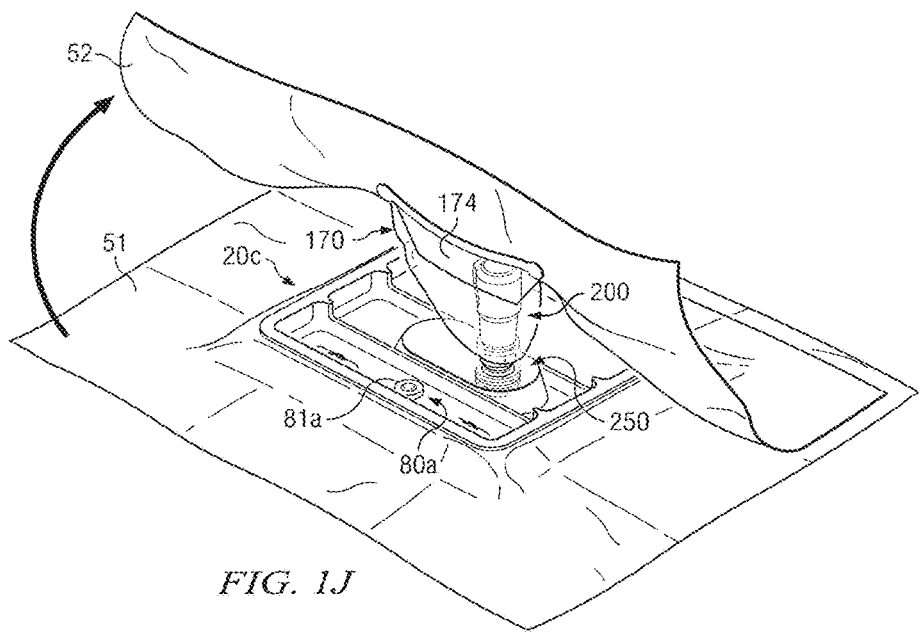
FIG. 1J is a schematic showing an isometric view of the medical procedure tray of FIG. 1G after lifting the second drape to enclose the powered driver (one example of a non-sterile medical device) in the containment bag.
Figure 2:
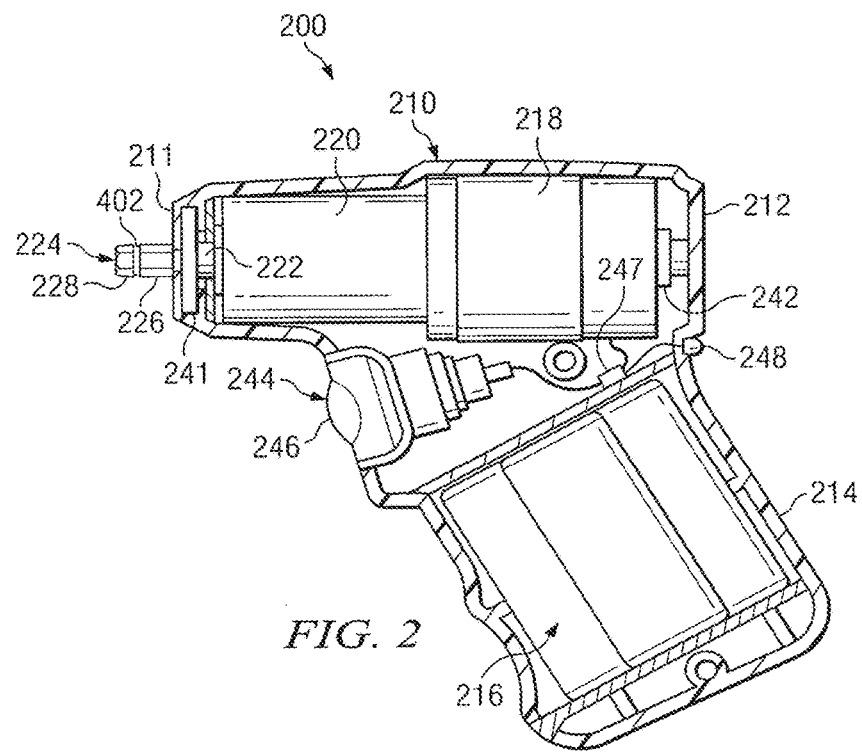
FIG. 2 is a schematic drawing showing one example of a powered driver operable for use with intraosseous (IO) devices incorporating teachings of the present disclosure.

First drape 51 and second drape 52 may then be unfolded as shown in FIG. 1H which will expose second opening 172 of containment bag 170 and second end 252 of coupler assembly 250 through fenestration 54 in second drape 52. A non-sterile person (not expressly shown) may next insert non-sterile powered driver 200 through opening or fenestration 54 and releasably engage end 224 of drive shaft 222 extending from non-sterile powered driver 200 with second end 252 of coupler assembly 250. The non-sterile person may then lift second drape 52 to a position such as shown in FIG. 1J with powered driver 200 disposed within containment bag 170. The non-sterile person may continue to lift second drape 52 to release engagement between portions of second drape 52 adjacent to fenestration 54 and portions of containment bag 170 adjacent to second opening 172.

Typical procedures associated with using a medical procedure tray or kit incorporating teachings of the present disclosure may include the following steps. Medical procedure tray 20d at a desired location for performing an associated medical procedure. For example medical procedure tray 20d may be placed on a table or cart adjacent to a surgical table on which a bone marrow aspiration procedure or a bone marrow biopsy procedure may be performed.

An associated cover may be removed from medical procedure tray 20d by a sterile person to expose folded drapes 51 and 52. Drapes 51 and 52 may then be unfolded by the sterile person such as shown in FIG. 1H. A non-sterile person may then pick up non-sterile powered driver 200 and insert powered driver 200 through fenestration 54 in second drape 52 such as shown in FIG. 1H. End 224 of drive shaft 222 of powered driver 200 may "snap" into place within second end 252 of coupler assembly 250. The non-sterile person may then lift second drape 52 such as shown in FIG. 1J which will result in lifting containment bag 170 up and over powered driver 200. The non-sterile person may then remove second drape 52.

A sterile person may next close flap 174 over second end 172 of containment bag 170. The sterile person may then grasp handle 214 of powered driver 200 through containment bag 170 and lift powered driver 200 with coupler assembly 250 attached thereto from holder 58 disposed in kit 20c. The sterile person may then remove an intraosseous device such as biopsy needle set 100b from medical procedure kit 20c and insert second end 102 of biopsy needle set 100b into first end 251 of coupler assembly 250. A "snap" may be felt when second end 102 of biopsy needle set 100b (or any other intraosseous device incorporating teachings of the present disclosure) is releasably latched within first end 251 of coupler assembly 250. A needle safety cap (not expressly shown) may be removed from first end 101 of biopsy needle 100b after releasably engaging second end 102 with first end 251 of coupler assembly 250.

Powered driver 200 disposed within containment bag 170 along with coupler assembly 250 and biopsy needle set 100b extending there from may be held in one hand while a sterile person identifies the insertion site with the other hand. Powered driver 200 may be positioned over the insertion site to introduce first end 101 of biopsy needle set 100b through the skin in the direction and towards the bone. Upon contact with the bone the operator may squeeze button or trigger 246 and apply relatively steady gentle pressure to handle 214 of powered driver 200. Upon penetration of the bone cortex, the operator may release trigger 246 to stop further insertion of first end 101 of biopsy needle set 100b.

First housing segment 280 may then be activated to release second end 102 of biopsy needle set 100b from engagement with coupler assembly 250. Second hub 150a may then be rotated counterclockwise to disengage second hub 150a and associated stylet 120 from first hub 140a. See FIG. 3B. Stylet 120 may then be pulled out and removed from biopsy needle or cannula 110b. First end 121 of stylet 120 may then be inserted into sharps protector 64a. Upon completion of an appropriate biopsy procedure second hub 150a may be reengaged with first hub 140a. First end 251 of coupler assembly 250 may then be reengaged with second end 102 of biopsy needle set 100h to rotate or spin biopsy needle set 100b while withdrawing from the insertion site. After removal from the insertion site, second end 102 of biopsy needle set 100b may be disengaged from coupler assembly 250. First end 101 of biopsy needle set 100b may then be inserted into sharps container 64a.

After second drape 52 has been removed from engagement with second opening 172, a sterile person (not expressly shown) may close flap 174 to seal non-sterile powered driver therein. The sterile person may then remove containment bag 170, powered driver 200 and coupler assembly 250 from holder 58. The sterile person may then releasably engage first end 251 of coupler assembly 250 with one end of a sterile intraosseous device disposed within medical procedure tray 20c in accordance with teachings of the present disclosure. After completion of a bone marrow aspiration procedure, bone and/or bone marrow biopsy procedure and/or other medical procedures using the intraosseous device, the sharp end or sharp tip of the intraosseous device may be inserted into material 66 in sharp protector 64a for further disposal in accordance with the appropriate procedures.

A wide variety of drapes may be satisfactory used with a medical procedure tray or kit incorporating teachings of the present disclosure. One example of a drape associated with medical procedures is shown in U.S. Pat. No. 4,553,539. However, first drape 51 and/or second drape 52 may be formed from a wide variety of materials and may have a wide variety of configurations and/or dimensions.

Figure 7A:
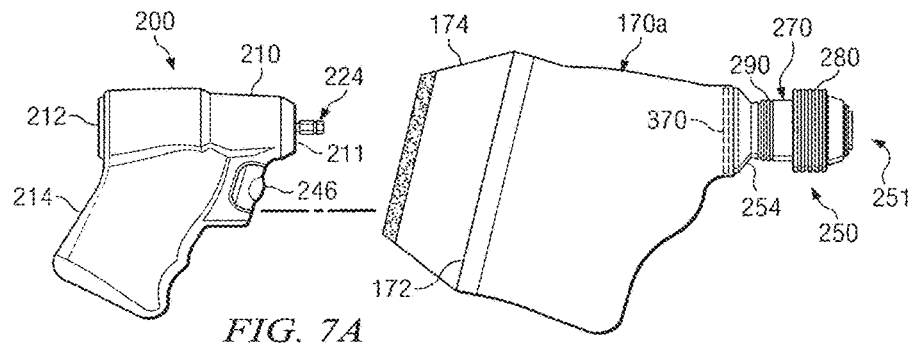
FIG. 7A is a schematic drawing showing an isometric view with portions broken away of a powered driver, containment bag or sterile sleeve and coupler assembly incorporating teachings of the present disclosure.
Figure 7B:
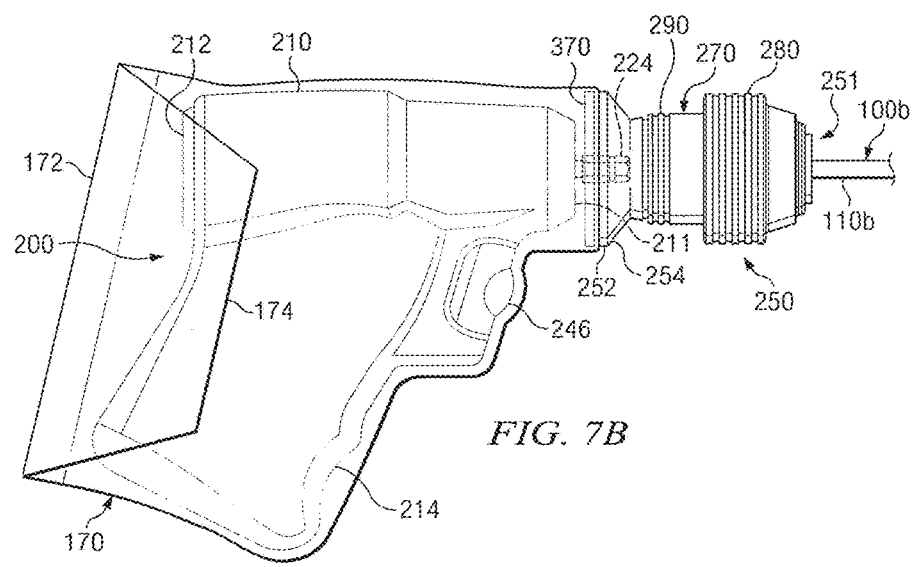
FIG. 7B is a schematic drawing showing another view of the powered driver disposed in the containment bag of FIG. 7A in accordance with teachings of the present disclosure.

Powered driver 200 as shown in FIGS. 1E, 1F, 1I, 2, and 5A and powered driver 200a as shown in FIGS. 7A and 7B may be satisfactorily used to insert an intraosseous device incorporating teachings of the present disclosure into a bone and associated bone marrow. Powered drivers 200 and 200a may be substantially similar except for respective ends 224 and 224a of drive shaft 222 extending from first end 211 of housing 210. See for example FIGS. 2 and 7A. Therefore, only powered driver 200 will be described in more detail.

Powered driver 200 may include housing 210 having a general configuration similar to a small pistol defined in part by handle 214. Various components associated with powered driver 200 may be disposed within housing 210 including handle 214. For example a power source such as battery pack 216 may be disposed within handle 214. Battery pack 216 may have various configurations and dimensions.

Housing 210 including handle 214 may be formed from relatively strong, heavy duty polymeric materials such as polycarbonate or other satisfactory materials. For some applications housing 210 may be formed in two halves (not expressly shown) which may be joined together with a fluid tight seal to protect various components of powered driver 200 disposed therein.

Motor 218 and gear assembly 220 may be disposed within portions of housing 210 adjacent to handle 214. Motor 218 and gear assembly 220 may be generally aligned with each other. Motor 218 may be rotatably engaged with one end of gear assembly 220. Drive shaft 222 may be rotatably engaged with and extend from another end of gear assembly 220 opposite from motor 218. For some applications both motor 218 and gear assembly 220 may have generally cylindrical configurations.

Motors and gear assemblies satisfactory for use with powered driver 200 may be obtained from various vendors. Such motor and gear assemblies may be ordered as "sets" with one end of each motor securely attached to an adjacent end of an associated gear assembly. A drive shaft having various dimensions and/or configurations may extend from the gear assembly opposite from the motor. Such gear assemblies may sometimes be referred to as "reduction gears" or "planetary gears". The dimensions and/or configuration of housing 210 may be modified to accommodate an associated motor and gear assembly.

Distal end or first end 211 of housing 210 may include an opening (not expressly shown) with portions of drive shaft 222 extending therefrom. For some applications end 224 or the portion of drive shaft 222 extending from first end 211 of housing 210 may have a generally hexagonal cross section with surfaces 226 disposed thereon. Receptacle 263 disposed in second end 252 of coupler assembly 250 may have a matching generally hexagonal cross section. See FIG. 5E.

Surfaces 226 may extend generally parallel with each other and parallel with respect to a longitudinal axis or rotational axis (not expressly shown) associated with drive shaft 222. One or more tapered surfaces 228 may also be formed on end 224 to assist with releasably engaging powered driver 200 with coupler assembly 250. See FIGS. 5E and 5G. The end of a drive shaft extending from a powered driver may have a wide variety of configurations. See for example FIGS. 6A and 6B.

A drive shaft having desired dimensions and configuration may extend from the gear assembly opposite from the motor. The drive shaft may be provided as part of each motor and gear assembly set. The dimensions and/or configuration of an associated housing may be modified in accordance with teachings of the present disclosure to accommodate various types of motors, gear assemblies and/or drive shafts. For example, powered drivers used with aspiration needles and/or biopsy needles may include gear assemblies with larger dimensions required to accommodate larger speed reduction ratios, for example between 60:1 and 80:1, resulting in slower drive shaft RPM's. Powered drivers used to provide intraosseous access during emergency medical procedures may operate at a higher speed and may include gear assemblies having a smaller speed reduction ratio, for example between 10:1 and 30:1, resulting in higher drive shaft RPM's. For some applications, the difference in size for gear assemblies may result in increasing the inside diameter of an associated housing by approximately two to three millimeters to accommodate larger gear assemblies associated with powered drivers used to insert biopsy needles and/or aspiration needles.

Coupler assemblies having corresponding openings or receptacles may be releasably engaged with end 224 extending from first end 211 of powered driver 200 or end 224a extending from first end 211 of powered driver 200a. For example, end 224 extending from first end 211 of housing 210 may be releasably engaged with receptacle 264 disposed proximate second end 252 of coupler assembly 250 as shown in FIGS. 1E, 1F, 5C and 5D.

For some applications thrust bearing 241 may be disposed between first end or distal end 211 of housing 210 and adjacent portions of gear assembly 220. Thrust bearing 242 may be disposed between second end or proximal end 212 of housing 210 and adjacent portions of motor 218. Thrust bearings 241 and 242 may limit longitudinal movement of motor 218, gear assembly 220 and drive shaft 222 within associated portions of housing 210.

Trigger assembly 244 may also be disposed within housing 210 proximate handle 214. Trigger assembly 244 may include trigger or contact switch 246. Motor 218 may be energized and deenergized by alternately depressing and releasing trigger 246. Electrical circuit board 247 may also be disposed within housing 210. Electrical circuit board 247 may be electrically coupled with trigger assembly 244, motor 218, power supply 216 and indicator light 248.

For some applications indicator light 248 may be a light emitting diode (LED) or a small more conventional light bulb. For some applications indicator light 248 may be activated when ninety percent (90%) of electrical storage capacity of battery pack 216 has been used.

The configuration and dimensions of an intraosseous device formed in accordance with teachings of the present disclosure may vary depending upon respective intended applications for each intraosseous device. For example the length of a biopsy needle formed in accordance with teachings of the present disclosure may vary from approximately five (5) millimeters to thirty (30) millimeters. However, biopsy needles having other lengths may also be formed in accordance with teachings of the present disclosure. Aspiration needles formed in accordance with teachings of the present disclosure may have lengths of approximately twenty five (25) millimeters, sixty (60) millimeters and ninety (90) millimeters. For some applications an aspiration needle having a length of ninety (90) millimeters or more may also include one or more side ports. See for example FIG. 3A. Intraosseous (IO) devices formed in accordance with teachings of the present disclosure may have outside diameters and longitudinal bores or lumens corresponding generally with eighteen (18) gauge to ten (10) gauge needles. The configuration and dimensions of each IO device may depend upon the size of an associated bone and desired depth of penetration of associated bone marrow.

Combining a powered driver with a coupler assembly and an aspiration needle set in accordance with teachings of the present disclosure may allow rapid access to the iliac crest or other insertion sites to extract associated bone marrow. Bone marrow aspiration systems incorporating teachings of the present disclosure may be capable of inserting an aspiration needle to a desired depth in cancellous bone in ten (10) to fifteen (15) seconds. This same capability may be used to obtain bone and/or bone marrow specimens depending upon the optimum speed for inserting a biopsy needle to obtain a reliable biopsy specimen in accordance with teachings of the present disclosure.

Bone marrow aspiration systems incorporating teachings of the present disclosure may provide a powered driver and a coupler assembly operable to insert an aspiration needle into cancellous bone and extract bone marrow. After an aspiration needle set has been inserted to a desired depth in a bone for extraction of bone marrow, a trocar or stylet may be removed from the lumen of an associated catheter or cannula. A hub assembly incorporating teachings of the present disclosure may be attached to the second end of the needle set allows relatively easy and quick removal of the trocar or stylet from the lumen of the cannula or catheter. A Luer lock fitting provided on a hub attached to the cannula or catheter may then be connected to a bone marrow aspiration system. See FIG. 10. For some applications hubs and hub assemblies may be formed using medical grade polycarbonate.

Upon completing aspiration of a desired volume or sample of bone marrow at a first target area, the trocar or stylet may be reinserted into the lumen of the outer penetrator or cannula. The first end of a hub attached to the trocar or stylet may be reengaged with the second end of a hub attached to the cannula or catheter. A powered driver and coupler assembly incorporating teachings of the present disclosure may then be used to insert the aspiration needle set to a second desired depth in the cancellous bone to obtain another bone marrow sample or the powered driver may be used to "power out" the aspiration needle set. Sharps safety capability for the stylet and/or cannula may be provided as part of such aspiration systems.

Figure 3A:
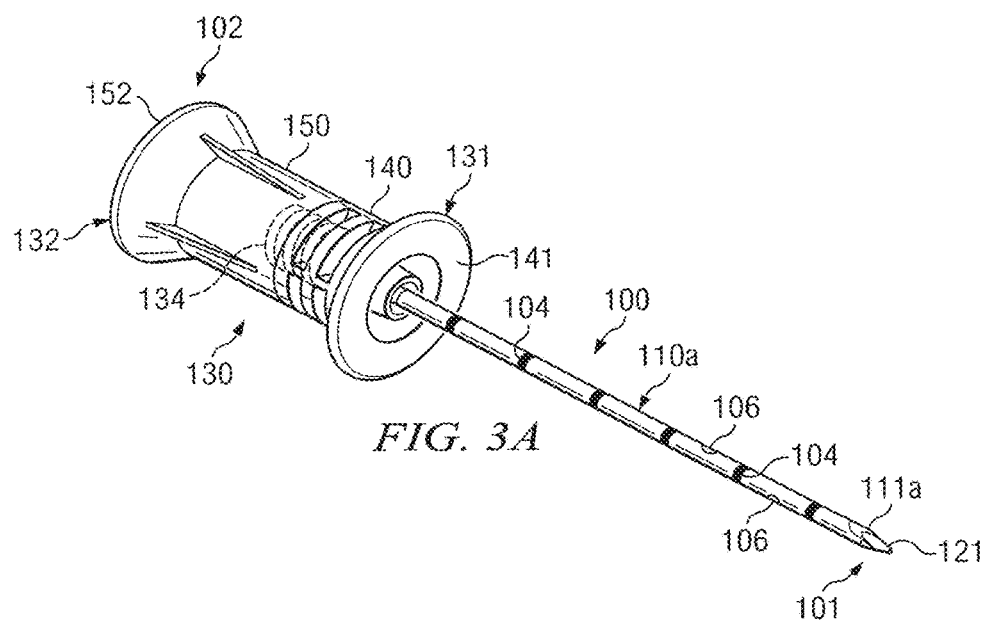
FIG. 3A is a schematic drawing showing an isometric view of the aspiration needle of FIG. 1A.
Figure 3B:
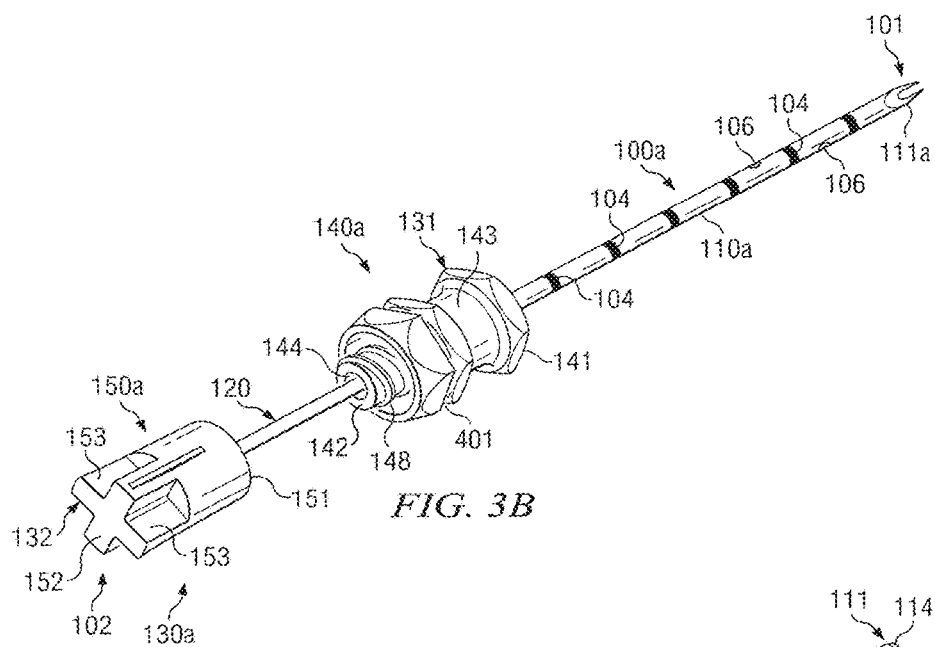
FIG. 3B is a schematic drawing showing an exploded view of the aspiration needle set of FIG. 3A.
Figure 3C:
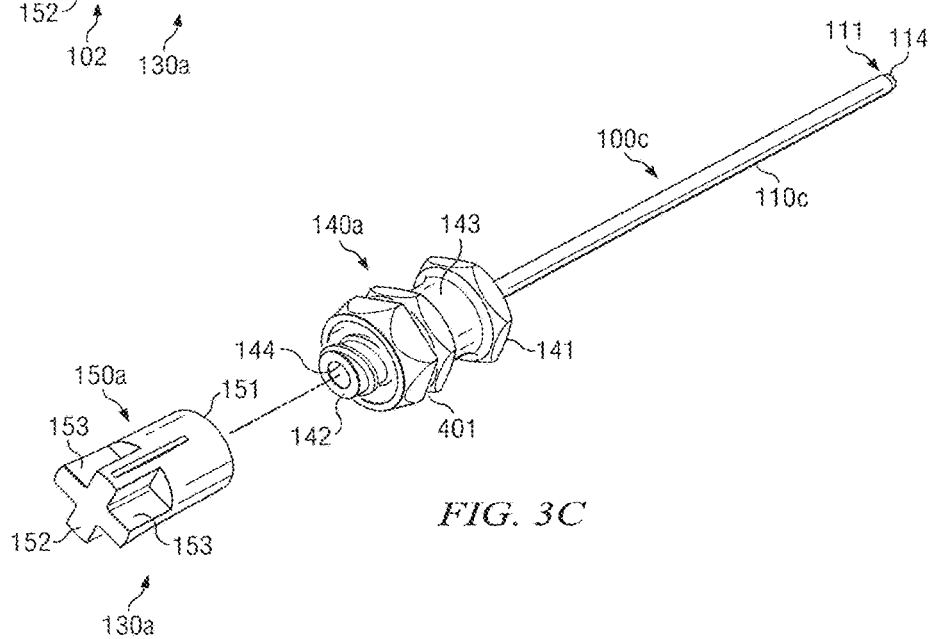
FIG. 3C is a schematic drawing showing an exploded, isometric view of one example of a biopsy needle incorporating teachings of the present disclosure.

Intraosseous (IO) needle sets or aspiration needle sets 100 and 100a as shown in FIG. 3A and FIG. 3B and biopsy needle 100c as shown in FIG. 3C represent only some examples of intraosseous devices formed in accordance with teachings of the present disclosure. Aspiration needle sets 100 and 100a may have similar outer penetrators or cannulas 110a and similar inner penetrators to stylets 120. See FIGS. 3A and 3B. However, IO needle set 100 may include hub assembly 130 while IO needle set 100a may include hub assembly 130a. See FIGS. 3A and 3B. Biopsy needle 100c may also include hub assembly 130a. See FIG. 3C.

For embodiments represented by IO needle sets 100 and 100a, first end 111a of cannula 110a and first end 121 of stylet 120 may be operable to penetrate a bone and associated bone marrow. Various features of first end 111a of cannula 110a and first end 121 of stylet 120 are shown in more detail in FIGS. 3D and 3F. First end 101 of IO needle sets 100 and 100a may correspond generally with first end 111a of cannula 110a and first end 121 of stylet 120.

Cannula 110a may have a plurality of markings 104 disposed on exterior portions thereof. Markings 104 may sometimes be referred to as "positioning marks" or "depth indicators." Markings 104 may be used to indicate the depth of penetration of aspiration needle set 100 or 100a into a bone and associated bone marrow. For some applications cannula 110a may have a length of approximately sixty (60) millimeters and may have a nominal outside diameter of approximately 0.017 inches corresponding generally with a sixteen (16) gauge needle. Cannula 110a may be formed from stainless steel or other suitable biocompatible materials. Positioning marks 104 may be spaced approximately one (1) centimeter from each other on exterior portions of cannula 110a. For some applications one or more side ports 106 may be formed in exterior portions of cannula 110a spaced from first end 111a.

Hub assembly 130 as shown in FIG. 3A may be used to releasably dispose stylet 120 within longitudinal bore or lumen 118 of cannula 110a. See FIG. 3E. Hub assembly 130 may include first hub 140 and second hub 150. The second end of cannula 110a, opposite from first end 111a, may be securely engaged with the second end of cannula 110a. The second end of stylet 120, opposite from first end 121, may be securely engaged with the first end of hub 150.

As shown in FIG. 3A cannula 110a may extend longitudinally from first end 141 of hub 140. Stylet 120 may also extend from the first end of hub 150 (not expressly shown). The second end of hub 140 may include a standard Luer lock fitting which may be releasably engaged with a corresponding Luer lock fitting disposed within the first end of second hub 150. Dotted lines 134 as shown in FIG. 3A may represent the resulting threaded connection between the second end of first hub 140 and the first end of second hub 150. Examples of Luer lock connections and/or fittings are shown in more detail in FIGS. 3B, 3C, 5E, 5F, 5I and 10. The Luer lock fitting disposed on the second end of hub 140 may be operable to be releasably engaged with a standard syringe type fitting and/or a standard intravenous (IV) connection.

Hub 150 includes second end 152 which generally corresponds with second end 132 of hub assembly 130 and second end 102 of IO needle set 100. Hub 140 may include first end 141 which may generally correspond with first end 131 of hub assembly 130. Cannula 110a may extend longitudinally from first end 141 of hub 140 and first end 131 of hub assembly 130.

Various types of receptacles may be satisfactory disposed in second end 152 of hub 150 for use in releasably engaging hub assembly 130 with a powered driver. For example, a receptacle having a generally tapered configuration corresponding with the tapered configuration of one end of a drive shaft extending from a powered driver may be releasably engaged with second end 152 of hub 150. Powered driver 200a as shown in FIGS. 6A and 6B may represent one example of a powered driver having a drive shaft extending from a housing with a tapered portion operable to be releasably engaged with a receptacle having a corresponding generally tapered configuration. For some applications such powered drivers may be secured to an intraosseous device by a magnet (not expressly shown) disposed on the end of the tapered shaft extending from the powered driver and a metal disk disposed within a corresponding receptacle in the intraosseous devices. Such powered drivers may also be used with intraosseous devices used to obtain emergency vascular access (EVA).

For other embodiments which may be discussed later, in more detail, the second end of a hub assembly may be operable to be disposed within a receptacle formed in a coupler assembly incorporating teachings of the present disclosure. One feature of the present disclosure may include forming a hub assembly which may be releasably engaged within a first receptacle disposed in a first end of a coupler assembly. See for example receptacle 263 proximate first end 261 of elongated core 260 as shown in FIG. 5E. The dimensions and configuration of receptacle 263 may be selected to prevent rotation of hub 150a relative to hub 140a while inserting (rotating) an IO device into a bone and associated bone marrow. The powered driver may be releasably engaged with a second receptacle disposed in a second end of the coupler assembly. See for example receptacle 264 proximate second end 262 of elongated core 260 as shown in FIG. 5E.

Intraosseous device or aspiration needle set 100a is shown in FIG. 3B with first end 151 of hub 150a spaced from second end 142 of hub 140a. Portions of stylet 120 extending from first end 151 of hub 150a are shown slidably disposed within lumen or longitudinal bore 118 of cannula 110a.

Hub assembly 130a as shown in FIG. 3B may include first end 131 which may correspond generally with first end 141 of hub 140a. Hub assembly 130a may also include second end 132 which may correspond generally with second end 152 of hub 150a and second end 102 of hub assembly 130a. See FIG. 3B. Cannula 110a may be attached to and extend from first end 141 of hub 140a.

Second end 142 of hub 140a may include one-half a typical Luer lock connection or fitting operable to be releasably engaged with corresponding portions of a Luer lock connection or fitting disposed in first end 151 of second hub 150a. For embodiments such as shown in FIGS. 3B and 3C, first end 131 of hub assembly 130a may correspond with first end 141 of first hub 140a. Second end 152 of second hub 150a may correspond with second end 132 of hub assembly 130a and second end 102 of aspiration needle set 100a.

At least one portion of hub assembly 130a may have a generally hexagonal cross section operable to be received within the generally hexagonal cross section of receptacle 264 disposed proximate first end 251 of coupler assembly 250. See FIG. 5E. For some embodiments portions of first hub 140a disposed adjacent to reduced outside diameter portion 143 may have generally hexagonal cross sections. See FIGS. 3B and 3C. Various cross sections other than hexagonal may be satisfactorily used to releasably engage a powered driver with one end of a coupler assembly and an intraosseous device with an opposite end of the coupler assembly.

Aspiration needle sets may often include a trocar, stylet or penetrator in combination with an associated cannula, catheter or outer penetrator. However, biopsy needles formed in accordance with teachings of the present disclosure may or may not include a trocar, stylet or inner penetrator. For example, biopsy needle 100c is shown in FIG. 3C attached to first end of hub 140a. A stylet or inner penetrator is not attached to first end 151 of hub 150a.

For embodiments represented by biopsy needle 100c, hub 140a may be used to releasably engage biopsy needle 100c in a receptacle formed in a coupler assembly incorporating teachings of the present disclosure. Hub 150a may be attached to close of end 141 of hub 140a. However, for many applications hub 140a without hub 150a may be connected with one end of a coupler assembly in accordance with teachings of the present disclosure. Biopsy needle 100c may be used to capture a biopsy specimen of a bone and associated bone marrow. Placing a trocar within biopsy needle 100c may result in substantial damage to the bone specimen during penetration of the bone by the combined tips of the trocar and biopsy needle 100c.

Hub 140a may include second end 142 with opening 144 formed therein. Passageway 146 may extend from second end 142 towards first end 141 of hub 140a. See FIGS. 5E, 5F and 5I. Passageway 146 may be operable to communicate fluids with lumen 118 of cannula 100a. Second end 142 of hub 140 may include various features of a conventional Luer lock connection or fitting, including threads 148. Corresponding threads 158 may be formed within first end 151 of hub 150a. See for example FIGS. 5E, 5F and 5I. The dimensions and configuration of receptacle 263 in first end 251 of coupler assembly 250 may be selected to prevent relative movement between hub 140a and hub 150a during insertion (rotation) of an IO device into a bone and associated bone marrow. If such relative movement occurs, threads 148 and 158 may be disconnected.

For some applications hub 140a and hub 150a may be formed using injection molding techniques. For such embodiments hub 140a may include reduced outside diameter portion 143 disposed between first end 141 and second end 142. See for example FIGS. 3B, 3C and 5C. In a similar manner a plurality of void spaces or cutouts 153 may be formed in hub 150a adjacent to and extending from second end 152 in the direction of first end 151. See for example FIGS. 3B, 3C and 5A. The configuration and dimensions of reduced diameter portion 143 and/or cutouts 153 may be varied to optimize associated injection molding techniques and at the same time provide required configurations, dimensions and material strength to allow associated hub assembly 130a to function in accordance with teachings of the present disclosure.

Figure 3D:
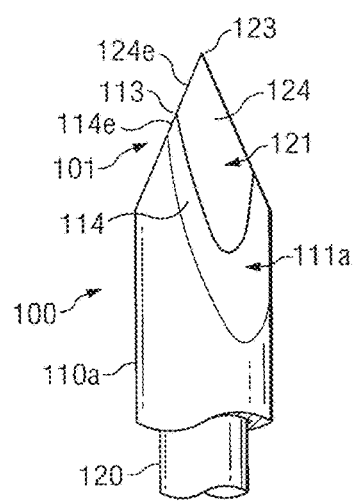
FIG. 3D is a schematic drawing showing an isometric view of another example of an intraosseous needle set incorporating teachings of the present disclosure.
Figure 3E:
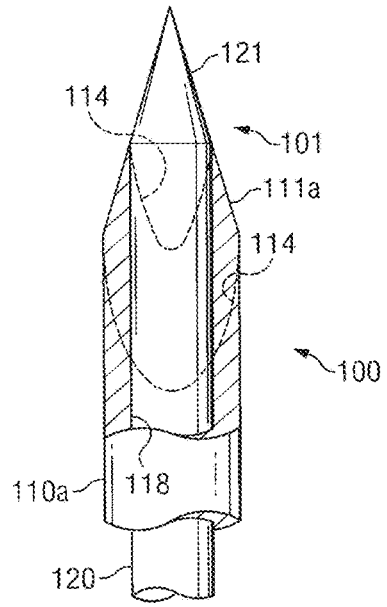
FIG. 3E is a schematic drawing showing an isometric view with portions broken away of the tips of the intraosseous needle set of FIG. 3A.

FIGS. 3D and 3E show one example of cutting surfaces and tips which may be formed adjacent to the ends of a cannula and an associated trocar in accordance with teachings of the present disclosure. For embodiments represented by cannula or outer penetrator 110a and trocar or inner penetrator 120a, tip 123 of stylet 120 may be disposed relatively close to tip 113 of cannula 110a. For some applications, first end 121 of trocar 120 and first end 111a of cannula 110a may be ground at the same time to form adjacent cutting surfaces 114 and 124. Grinding ends 111a and 121 at the same time may result in forming a single cutting unit to form generally matching cutting edges 124e and 114e such as shown in FIGS. 3D and 3E. Other types of cutting surfaces formed in accordance with teachings of the present disclosure may be discussed later.

First end 121 of trocar 120 may extend through opening 144 in second end 142 of hub 140a. See FIG. 3B. Hub 150a disposed on the second end of trocar 120 may be releasably engaged with the second end of cannula 110a represented by hub 140a. See FIG. 3B.

Oncologists and other health care provides may be unable to successfully obtain a suitable specimen of bone and/or bone marrow because currently available biopsy needles sometimes fail to capture a satisfactory specimen of bone and/or bone marrow. When a specimen is obtained, the specimen may sometimes be damaged or contaminated. Intraosseous devices incorporating teachings of the present disclosure may substantially reduce or eliminate problems associated with obtaining a suitable specimen of bone and/or bone marrow. Various teachings of the present disclosure may substantially increase the probability of obtaining a satisfactory biopsy specimen of cancellous bone and associated bone marrow.

Human bones may generally be described as having a hard outer lamellae or layer of osseous tissue known as "cortical bone". Cancellous bone (also known as trabecular or spongy bone) typically fills an inner cavity associated with cortical bone. Cancellous bone is another type of osseous tissue with generally low density and strength but high surface area. Cancellous bone typically includes spicules or trabeculae which form a latticework of interstices filled with connective tissue or bone marrow. Exterior portions of cancellous bone generally contain red bone marrow which produces blood cellular components. Most of the arteries and veins of a bone are located in the associated cancellous bone.

One of the benefits of the present disclosure may include providing various intraosseous devices including, but not limited to, biopsy needle sets and biopsy needles operable to reliably obtain biopsy specimens of cortical bone and/or cancellous bone without significant damage to associated biopsy specimens. For example, forming a plurality of cutting surfaces on the extreme end of an outer penetrator or cannula in accordance with teachings of the present disclosure may allow a resulting biopsy needle to more quickly penetrate a bone and associated bone marrow, may reduce the amount of time and force required to remove a bone and/or bone marrow specimen from a target area in accordance with teachings of the present disclosure.

The configuration of the tip of a cannula or outer penetrator may be modified in accordance with teachings of the present disclosure to provide optimum torque during insertion of the cannula or outer penetrator by a powered driver to obtain a bone and/or bone marrow biopsy specimen. A controlled, steady feed rate when using a powered driver may result in higher quality biopsy specimens as compared to manually inserted biopsy needles. At least one helical thread may be disposed within a hollow cannula proximate an associate tip or first end to assist with capturing a bone and/or bone marrow biopsy specimen.

The quality of a bone and/or bone marrow specimen and reliability of obtaining a bone and/or bone marrow specimen using a powered driver and biopsy needle incorporating teachings of the present disclosure may be substantially improved by using an optimum feed rate for inserting the biopsy needle into a bone and associated bone marrow. Feed rate or speed of insertion of a biopsy needle incorporating teachings of the present disclosure may be a function of the pitch of at least one thread disposed on an interior portion of the biopsy needle and revolutions per minute (RPM) of the biopsy needle.

RPM=Feed rate×Pitch of threads

Helical thread 190 as shown in FIGS. 4C, 4D and 4E may have a pitch of approximately twenty four (24) threads per inch. An optimum pitch may vary based on factors such as reduction gear ratio (77:1 for some embodiments) and load placed on an associated motor.

Further technical benefits may include reducing physical requirements and mental stress on users and decreasing pain and stress on patients by increasing speed and control of the needle set insertion during bone marrow biopsy and bone marrow aspiration procedures.

The combination of a powered driver and a biopsy needle set may be used to rapidly access the Iliac crest or other insertion sites to extract associated bone and/or bone marrow specimens. Bone marrow biopsy systems incorporating teachings of the present disclosure provide a powered alternative to current manual techniques for inserting biopsy needles into bone and bone marrow which are generally considered the industry standard.

For some applications, an aspiration needle or biopsy needle formed in accordance with teachings of the present disclosure may include a hollow cannula or catheter having one end formed by electrical discharge machining (EDM) techniques, grinding techniques and/or other machining techniques. A plurality of teeth may be formed on one end of the cannula or catheter using EDM techniques, grinding techniques and/or other machining techniques.

For some embodiments a stylet or trocar may also be disposed within the cannula or catheter with a first end of the stylet extending from a first end of the cannula or catheter. Increasing the length of the first end of the stylet or trocar extending from the first end of the cannula or catheter may reduce the amount of torque or force required to penetrate a bone and may reduce time required for an associated aspiration needle set or biopsy needle set to penetrate the bone and associated bone marrow.

A specific powered driver, intraosseous device and tip configuration will generally produce the same torque when drilling in a hard bone or a soft bone. However, the time required to drill to a first depth in a hard bone will generally be greater than the time required to drill to similar depth in a soft bone.

For still other embodiments, teeth formed on one end of a cannula or catheter may be bent radially outward to reduce the amount of time and/or force required to penetrate a bone and associated bone marrow using the cannula or catheter. For some applications a powered driver and aspiration needle set or biopsy needle set formed in accordance with teachings of the present disclosure may provide access to a patient's bone marrow using a similar amount of torque. The length of time for penetrating a relatively hard bone may be increased as compared with the length of time required to penetrate a relatively softer bone.

The tips of several stylets and cannulas incorporating teachings of the present disclosure were slowly ground with coolant to prevent possible thermal damage to metal alloys or spring material used to form the stylets and cannulas. The stylets and cannulas were assembled into respective IO needle sets. The tips of each needle set were inserted into sawbones blocks under controlled test conditions. Some testing was conducted with Pacific Research sawbones blocks. The tips of the needle sets were inserted to a depth of approximately two centimeters with ten pounds (10 lbs) of force and twelve volts direct current (12 VDC) applied to an associated powered driver. There was no measurable or visual wear of the stylet or cannula tips after completion of the testing.

For some embodiments a generally hollow biopsy needle may be substantially continuously rotated at an optimum speed or RPM during insertion into a selected target area to obtain a biopsy specimen. The biopsy needle may include a longitudinal bore extending from a first, open end of the needle to a second, open end of the needle. A small helical thread may be formed on interior portions of the longitudinal bore proximate the first end. For some embodiments the thread may have a pitch similar to threads used on conventional wood screws. The rate of rotation or revolutions per minute (RPM) of the biopsy needle may be selected by installing a gear assembly with a desired speed reduction ratio (typically between 60:1 and 80:1) between a motor and an associated drive shaft. For some applications the gear assembly may reduce speed of rotation of an attached motor at a ratio of approximately 66:1 or 77:1.

Figure 3F:
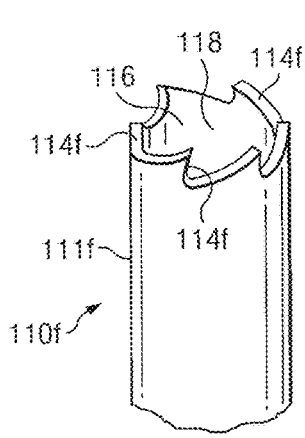
FIG. 3F is a schematic drawing showing an isometric view of one embodiment of the tip of an intraosseous device or cannula incorporating teachings of the present disclosure.

Outer penetrator or cannula 110*f* as shown in FIG. 3F may include first end 111*f* having a plurality of cutting surfaces 114*f* formed adjacent to opening 116 in first end 111*f*. Opening 116 may communicate with and form a portion of an associated longitudinal bore or lumen 118. For some applications cutting surfaces 114*f* may be formed using electrical discharge machining (EDM) techniques.

Figure 3G:
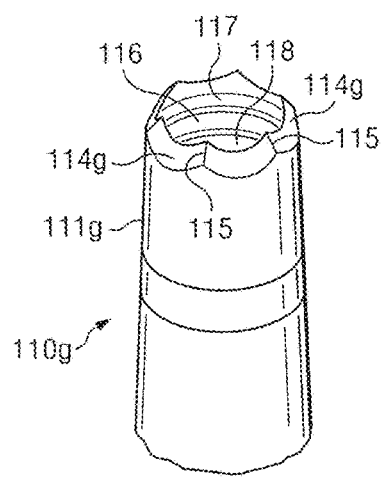
FIG. 3G is a schematic drawing showing an isometric view of another embodiment of the tip of a biopsy needle incorporating teachings of the present disclosure.
Figure 3H:
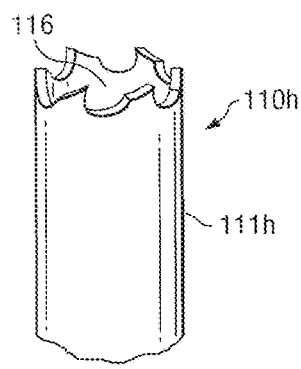
FIG. 3H is a schematic drawing showing an isometric view of still another embodiment of the tip of an intraosseous device or catheter incorporating teachings of the present disclosure.

For embodiments such as shown in FIG. 3G, outer penetrator or cannula 110*g* may include first end 111*g* having a generally tapered configuration or reduced outside diameter as compared with other portions of cannula 110*g*. A plurality of cutting surfaces 114*g* may be disposed on end 111*g* adjacent to respective opening 116. For some applications, cutting surfaces 114*g* may be formed using machine grinding techniques. For embodiments end 111*g* of cannula 110*g* may include six ground cutting surfaces 114*g* with respective crowns 115 may be formed therebetween. Forming a biopsy needle set and/or biopsy needle with tapered end 111*g* and a plurality of cutting surfaces 114*g* and crowns 115 may provide improved drilling performance when the resulting biopsy needle set and/or biopsy needle is used with a powered driver in accordance with teachings of the present disclosure.

For some applications, helical groove 117 may be formed within longitudinal bore 118 proximate respective opening 116. Helical groove 117 may assist with retaining a biopsy specimen or a bone marrow specimen within longitudinal bore 118.

Testing conducted with cannulas or outer penetrators formed in accordance with teachings of the present disclosure indicated that forming cutting surfaces or cutting teeth with electrical discharge machining (EDM) sometimes resulted in the associated cannula or outer penetrator being able to drill through a bone and associated bone marrow slightly faster than a cannula or outer penetrator having cutting surfaces formed using grinding techniques. Some test results also indicated that bending cutting surfaces formed on one end of a cannula or outer penetrator in accordance with teachings of the present disclosure may reduce the amount of time and/or the amount of force required to remove a bone and/or bone marrow specimen from a target area.

Figure 3I:
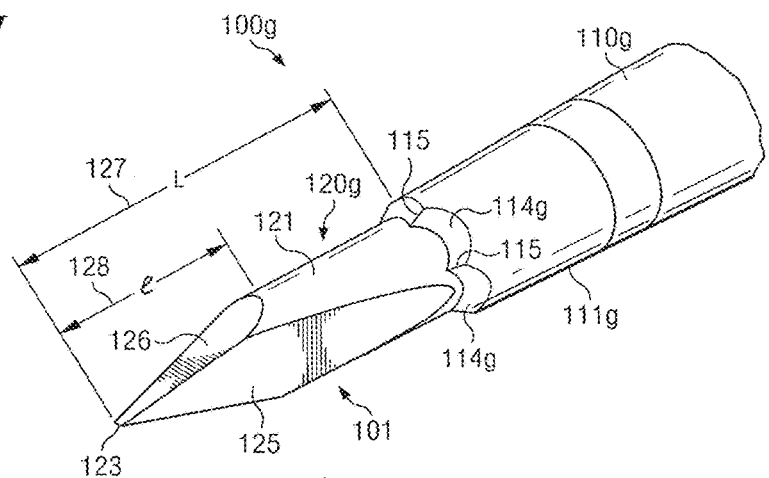
FIG. 3I is a schematic drawing showing an isometric view with portions broken away of a intraosseous needle set incorporating teachings of the present disclosure.
Figure 3J:
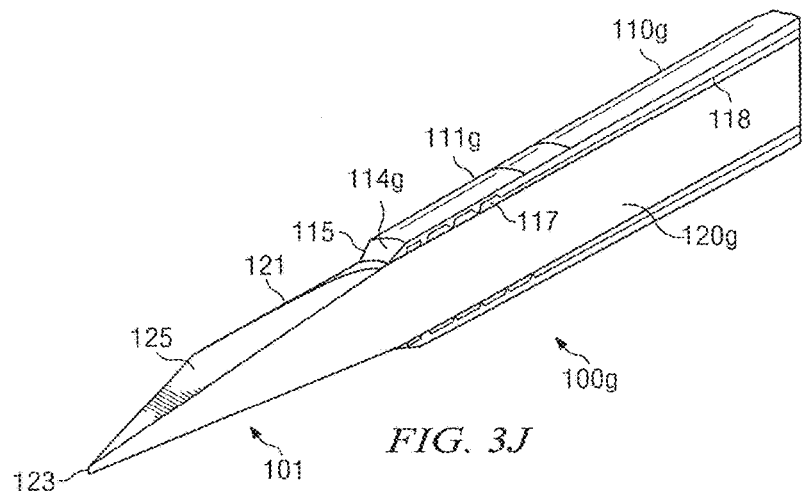
FIG. 3J is a schematic drawing showing an isometric view with portions broken away of another example of a biopsy needle set incorporating teachings of the present disclosure.

Intraosseous needle set or biopsy needle set 100*g* is shown in FIGS. 3I and 3J. Biopsy needle set 100*g* may include cannula or outer penetrator 110*g* with stylet or inner penetrator 120*g* slidably disposed therein. First end 101 of biopsy needle set 100*g* is shown in FIGS. 3I and 3J. For some applications first end 101 of biopsy needle set 100*g* may minimize damage to skin and soft body tissue at an insertion site.

For some applications inner penetrator or trocar 120*g* may include first end 121 having a plurality of cutting surfaces 125 and 126 formed on exterior portions thereof extending from associated tip 123 towards second end of trocar or inner penetrator 120*g*. For some applications one or more cutting surfaces 125 may be formed having length 127 extending from tip 123 to associated cutting surfaces 114*g* in associated cannula 110*g*. One or more cutting surfaces 126 may be formed adjacent to each cutting surface 125 with second length 128. First length 127 may be greater than second length 128. The ratio of first length 127 and second length 128 may be varied in accordance with teachings of the present disclosure to provide optimum performance for penetrating a selected bone and associated bone marrow.

For some applications, a single thread may be disposed within the longitudinal bore or lumen of a biopsy needle, cannula, catheter or outer penetrator in accordance with teachings of the present disclosure. Various techniques and procedures may be satisfactorily used to place the single thread within a generally hollow cannula or outer penetrator proximate one end of the cannula or outer penetrator having one end operable to penetrate a bone and/or associated bone marrow. For some embodiments, a helical coil having a configuration and dimensions associated with the resulting single thread may be placed on one end of a mandrel such as a spot welding electrode assembly. The mandrel or electrode assembly may then be inserted through an opening in the one end of the cannula or outer penetrator operable to penetrate a bone and/or associated bone marrow. The helical coil may then be bonded with adjacent portions of cannula. Coils having a wide variety of dimensions and configurations may be satisfactorily used to place a single thread in a biopsy needle.

For embodiments such as shown in FIGS. 4A-4E, examples of helical threads are shown disposed in biopsy needles or cannulas incorporating teachings of the present disclosure. Outer penetrator or cannula 110*h* as shown in FIG. 4A may be formed with longitudinal bore 118 or lumen 118 extending from open 116 through cannula 110*h*. Electrode assembly or mandrel 160 may be used to install (spot weld) a single helical thread in lumen 118 proximate opening 116.

Helical coil 192 as shown in FIG. 4B may be placed on first end 161 of electrode assembly 160. Helical coil 192 may have the cross section of a right triangle. First end or copper electrode 161 may have an appropriate configuration and dimensions to be slidably received within opening 116 formed in first end 111 of cannula or outer penetrator 110*h*. First end or copper electrode 161 of mandrel 160 may include corresponding groove 164 with a configuration and dimensions satisfactory to receive helical coil 192 therein. Groove 164 may be formed with a desired pitch for resulting thread 190 when attached to or bonded with interior portions of cannula 110h.

For some applications electrode assembly 160 may include enlarged outside diameter portion or plastic insulator 194 disposed adjacent to first end 161. The dimensions and/or configuration of copper electrode 161 and plastic insulator 194 may be selected to accommodate installing helical coil 192 at an optimum location relative to end 116 for retaining biopsy specimens in lumen 118. For example, the dimensions and configuration of plastic insulator 194 may be selected to contact the extreme end of outer penetrator or cannula 110h proximate crowns 115.

Copper electrode 161 of electrode assembly 160 with helical coil 192 attached thereto may be inserted into opening 116 in first end 111h of cannula 110h. Electrode assembly 160 may be operable to conduct electricity to copper electrode 161 to accommodate spot welding helical coil 192 with adjacent interior portions of longitudinal bore 118 of cannula 110h. For some embodiments mandrel 160 may be formed from materials compatible with laser welding helical coil 192 with interior portions of lumen or longitudinal bore 118 of cannula 110h. When attached to interior portions of a cannula or outer penetrator 110h, helical coil 192 may form a single thread having shoulder 191 extending generally perpendicular to adjacent interior portions of lumen 118. The resulting dimensions and configuration of helical thread 190 may be selected to optimize retaining a specimen of bone and/or bone marrow on shoulder 191 of thread 190 within lumen 118.

Cannula 110c of biopsy needle 100c is shown in FIG. 4C with helical thread 190 disposed therein. The combination of helical thread 190 with shoulder 191 extending substantially perpendicular to interior portions of lumen 118 may increase the reliability of biopsy needle 100c to retain a specimen of bone and/or bone marrow. For some applications combining helical thread 190 with cutting surfaces 114 and crowns 115 may substantially increase the reliability of obtaining a satisfactory bone specimen when using biopsy needle 100c with a powered driver in accordance with teachings of the present disclosure.

Helical thread 190 may be positioned at an optimum location relative to opening 116 in cannula 110c to begin capture of a bone marrow specimen or cancellous bone core. By inserting biopsy needle 100c at an optimum feed corresponding with the pitch of helical thread 190, helical thread 190 may be "screwed in" cancellous bone entering opening 116 to substantially increase the probability of capturing a satisfactory biopsy specimen or bone marrow core.

For embodiments such as shown in FIG. 4D cannula or outer penetrator 110d may include first end 111d having a plurality of exterior cutting surfaces 114d formed thereon and extending therefrom. The length of cutting surfaces 114d may be longer than the length of corresponding cutting surfaces 114. Respective crowns 115d may be formed between adjacent cutting surfaces 114d and 114g.

For some applications a helical thread having a generally "wedge shaped" cross section similar to an equilateral triangle may be disposed within the longitudinal bore or lumen of an outer penetrator or cannula incorporating teachings of the present disclosure. For example cannula 110d may include helical thread 190a having a generally wedge shaped cross section corresponding approximately with an equilateral triangle. Helical thread 190a may be installed within cannula 110d using apparatus and procedures as previously described with respect to helical thread 190.

FIG. 4E shows an example of combining inner penetrator or stylet 120c with cannula or outer penetrator 110c having helical thread 190 disposed therein to form biopsy needle set 100c in accordance with teachings of the present disclosure. Biopsy needle 100c is shown in FIGS. 3C and 4C without a stylet or trocar. Biopsy needle set 100c is shown in FIG. 4E with trocar or stylet 120c disposed in cannula 110c. Trocar 120c may include end 121c with a pair of cutting surfaces 125 and a pair of cutting surface 126 as shown in FIG. 3I. Surfaces 125 and 126 may cooperate with each other to form a cutting tip on trocar or stylet 120c similar to a "chisel point" drill bit. The pair of cutting surfaces 125 may be offset (relief angle) approximately eight degrees relative to the pair of cutting surfaces 126. The included angle of cutting surfaces 125 may be approximately thirty four degrees (34°) plus or minus four degrees)(±4°. The included angle of cutting surfaces 126 may be approximately sixteen degrees (16°) plus or minus three degrees) (+3°).

For some applications end 121 of trocar 120c may extend from end 111c of cannula 110c with respective cutting surfaces 114 of cannula 110g disposed adjacent to the end of each cutting surface 126 (short cutting surface) opposite from tip 123 of trocar 120c. See FIG. 4E. As a result portions of each cutting surface 125 (long cutting surface) of trocar 120c may be disposed within end 111 of cannula 110c. See FIG. 4E.

Placing portions of cutting surfaces 125 within end 111 of cannula 110c may result in more uniform forces being applied to end 101 of intraosseous device 100c while penetrating the cortex of an associated bone using biopsy needle set 100c and a powered driver in accordance with teachings of the present disclosure. When the cortex has been penetrated, forces applied to end 101 of biopsy needle set 100c may decrease sufficiently to indicate that end 101 has now entered associated bone marrow. An operator may then withdraw trocar 120c from cannula 110c and position end 111c of cannula 110c at a desired target area to perform a bone marrow biopsy.

For some embodiments threads 190 and 190a may extend approximately 0.005 inch from adjacent portions of an associated longitudinal bore or lumen 118. The outside diameter of an associated trocar such as trocar 120c as shown in FIG. 4E may be reduced to accommodate the height of thread 190 or 190a. The following test results were obtained during insertion of intraosseous devices such as biopsy needle set 100c shown in FIG. 4E into sawbones material or blocks with three millimeters (3 mm) of fifty pound (50#) and forty millimeters (40 mm) of forty pound (40#) material.

| Test # | Motor Torque(g-cm) | Time(s) |
| --- | --- | --- |
| 44 | 1101 | 2.23 |
| 45 | 1081 | 2.49 |
| 46 | 1071 | 2.36 |
| 47 | 1081 | 2.50 |
| 48 | 1030 | 2.46 |
| 49 | 1070 | 2.33 |
| Average | 1072 | 2.40 |

The distance between the end of cutting surface 126 or trocar 120c and adjacent cutting surface 114 on cannula 110c was approximately 0.14 inches. End 111 of cannula 110c had six (6) ground cutting surfaces 114. The outside diameter of trocar 120c was approximately 0.086 inches.

Coupler assemblies incorporating teachings of the present disclosure may function as "quick release mechanisms" operable to engage and disengage an IO device from a powered driver disposed within a flexible containment bag or sterile sleeve. Such coupler assemblies may allow rotation of an IO device without damage to the flexible containment bag or sterile sleeve. For some applications the IO device may be an aspiration needle or a biopsy needle. One end of the coupler assembly may be operable to form a fluid seal or fluid barrier with adjacent portions of the containment bag or sterile sleeve. A coupler assembly incorporating teachings of the present disclosure may also be described as a port assembly attached to a containment bag. Such port assemblies may allow easy engagement or disengagement of a powered driver from an IO device and at the same time allow the powered driver to "power in and power out" an IO device from an insertion site.

A coupler assembly incorporating teachings of the present disclosure may be used in "non-sterile" environments and/or medical procedures which do not require the use of a containment bag or sterile sleeve.

FIGS. 5A-5I and 6A-6B show various examples of coupler assemblies or port assemblies incorporating teachings of the present disclosure. FIG. 5A-5I are schematic drawings showing various views of powered driver 200, coupler assemblies 250, 250a and 250b and intraosseous device 100b incorporating various teachings of the present disclosure. Coupler assemblies 250, 250a and 250a may each include respective first end 251 operable to be releasably engaged with one end of an intraosseous device such as, but not limited to, second end 102 of biopsy needle set 100b.

Coupler assembly 250 as shown in FIGS. 5E-5H may include second end 252 operable to be releasably engaged with a portion of a drive shaft extending from a powered driver, such as, but not limited to, end 224 of drive shaft 222 extending from first end 211 of housing 210 of powered driver 200. As discussed later, second end 252 of coupler assembly 250 may be securely engaged with an opening in a containment bag or sterile sleeve. Second end 252a of coupler assembly 250a and second end 252b of coupler assembly 250b do not include similar features. As a result coupler assemblies 250a and 250b may primarily be used in applications which do not require a sterile environment.

Coupler assemblies 250, 250a and 250b may have substantially the same or similar components, functions and features except for second end 252a of coupler assembly 250a and associated second end 272a of housing assembly 270a and second end 250b of coupler assembly 250b and associated second end 272b of housing assembly 270b. Therefore, various features of the present disclosure may be described with respect to coupler assembly 250 since both coupler assemblies 250a and 250b have substantially the same characteristics and features except for attachment with a containment bag or sterile sleeve.

Coupler assemblies incorporating various teachings of the present disclosure may be placed in a medical procedure tray or kit with one end down and an opposite end looking up to allow "hands free" releasable engagement with a powered driver or a manual driver. For example, coupler assembly 250 may be disposed in medical procedure tray 20c with first end 251 insert into holders 58 and second end 252 looking up. See FIGS. 1C, 1E and 1F. As a result, end 224 of drive shaft 222 extending from powered driver 200 may be inserted into and releasably engaged with second end 252 of coupler assembly 250 without requiring an operator or user (not expressly shown) to physically contact or manipulate any portion of coupler assembly 250. Various features of associated "hands free" latching mechanisms will be discussed with respect to FIGS. 5E, 5F, 5G and 5H.

Figure 5A:
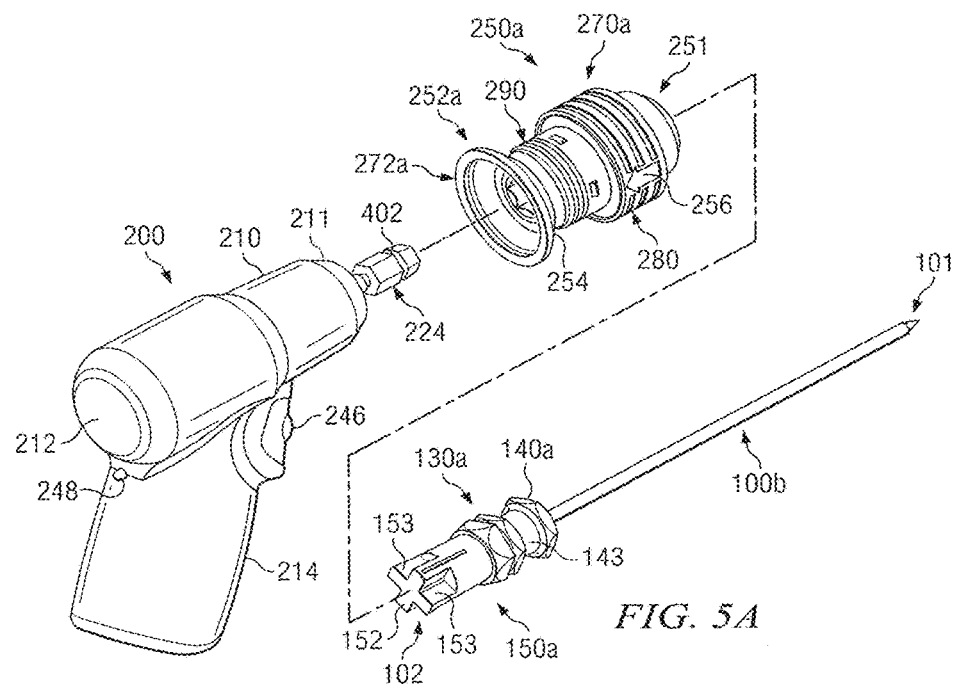
FIG. 5A is a schematic drawing showing an exploded, isometric view of a powered driver, coupler assembly and an intraosseous device incorporating teachings of the present disclosure.
Figure 5B:
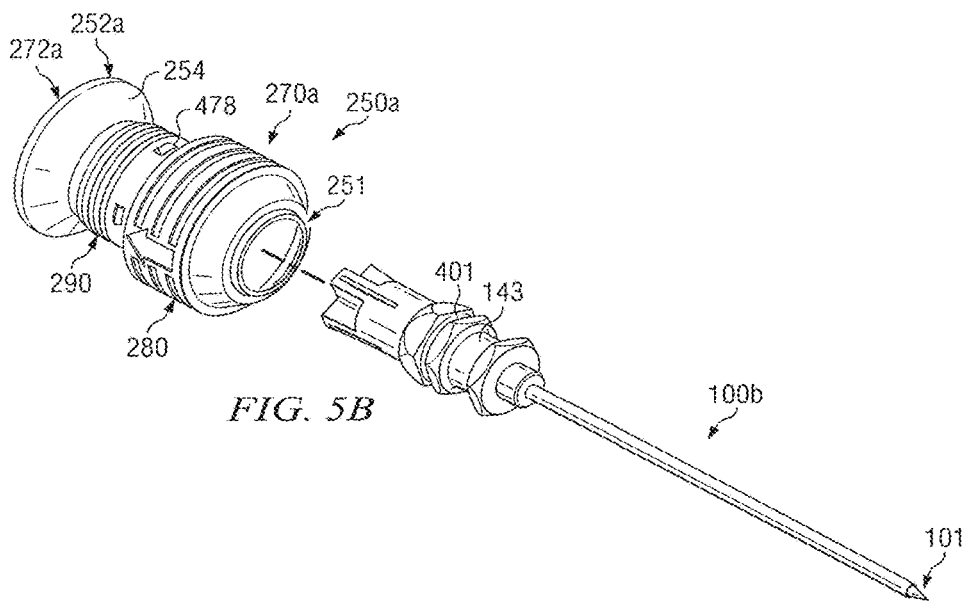
FIG. 5B is a schematic drawing showing another exploded, isometric view of the coupler assembly and intraosseous device of FIG. 5A.
Figure 5C:
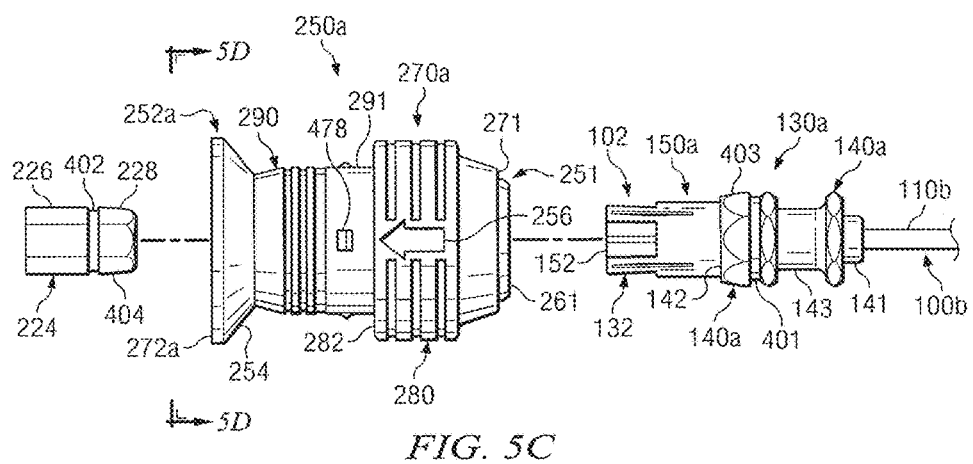
FIG. 5C is a schematic drawing in section with portions broken away showing another exploded view of the powered driver, coupler assembly and intraosseous device of FIG. 5A.
Figure 5D:
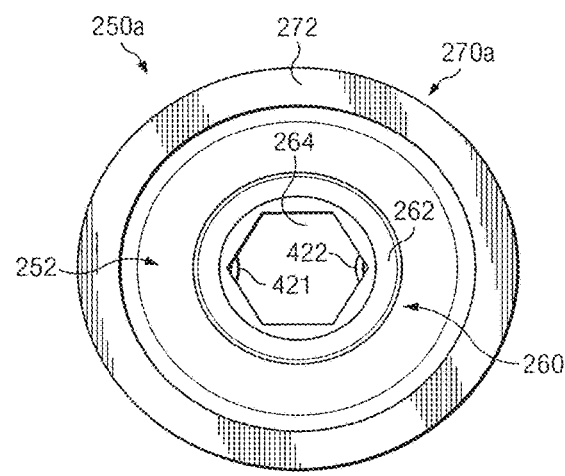
FIG. 5D is schematic drawing showing an end view of the coupler assembly taken along lines 5D-5D of FIG. 5C prior to insert one end of a device shaft therein.
Figure 5E:
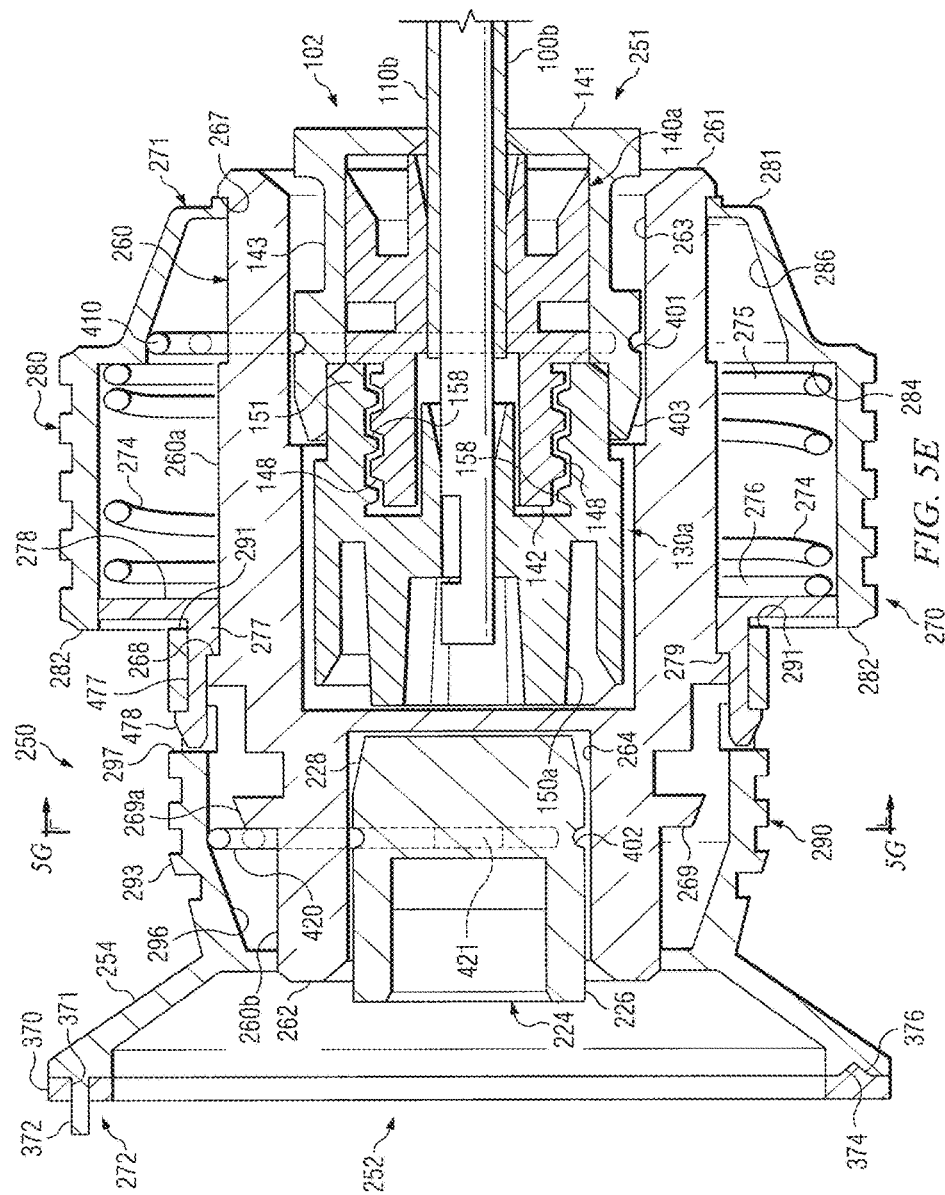
FIG. 5E is a schematic drawing in section with portions broken away showing the powered driver, coupler assembly and intraosseous device of FIG. 5A.
Figure 5F:
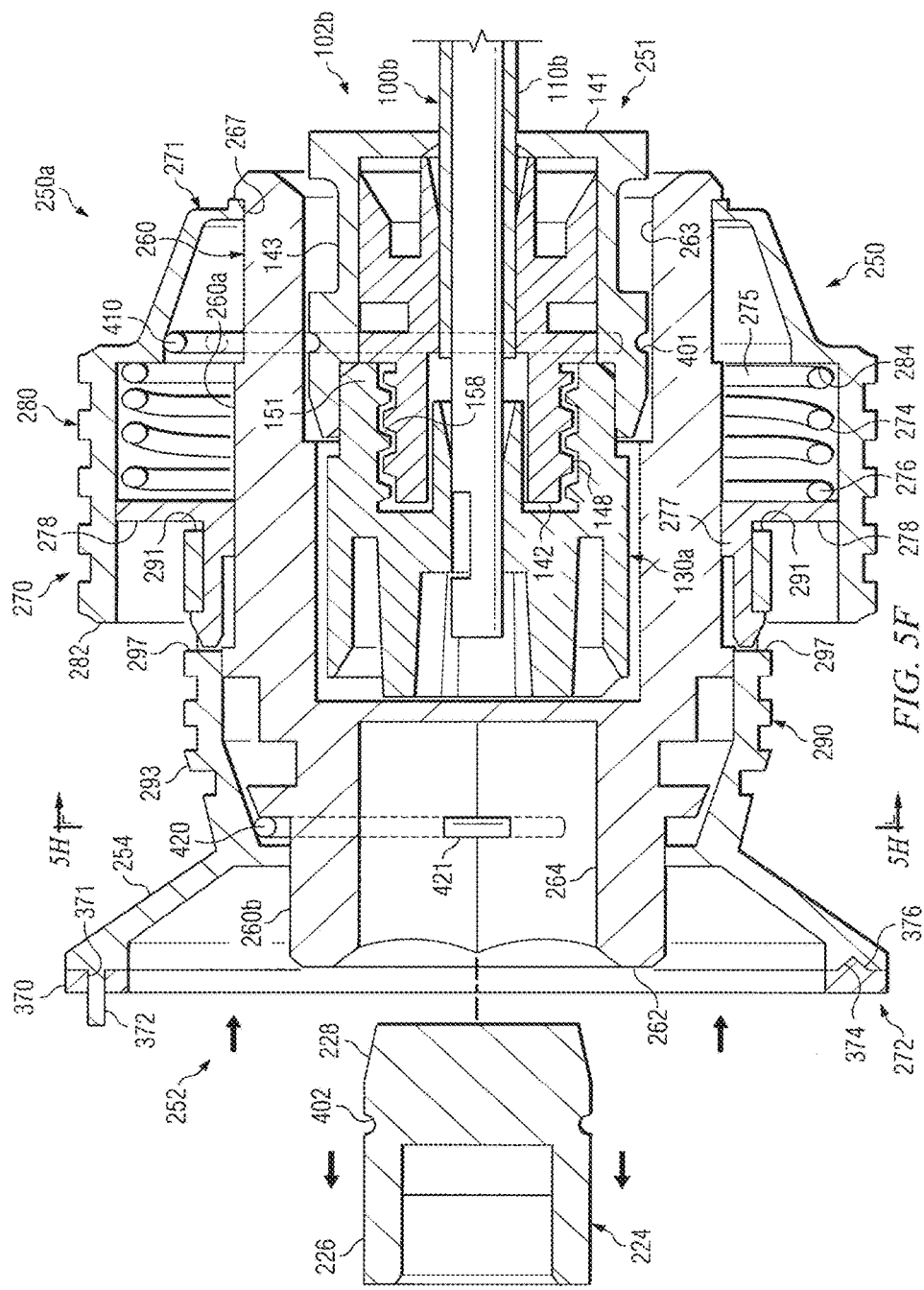
FIG. 5F is a schematic drawing in section with portions broken away showing the coupler assembly of FIG. 5D in a second position allowing release of a powered driver from a receptacle disposed in the first end of the coupler assembly.

As shown in FIGS. 5E and 5F, coupler assembly 250 may include elongated core 260 with housing assembly 270 slidably disposed on exterior portions of elongated core 260. Housing assembly 270 may include first end 271 and second end 272 which may be generally aligned with respective first end 261 and respective second end 262 of elongated core 260. For some applications, elongated core 260 may have a generally cylindrical configuration defined in first exterior portion 260a and second exterior portion 260b with various shoulders and/or recesses formed thereon. For some embodiments first exterior portion 260a may have a larger diameter than second exterior portion 260b.

Coupler assembly 250a and coupler assembly 250b may include respective elongated cores 260 having similar features and functions as described with respect to coupler assembly 250. Coupler assembly 250a may include housing assembly 270a with substantially the same components, functions and features as described with respect to housing assembly 270 except for second end 272a of housing assembly 270a. Coupler assembly 250b may include housing assembly 270b having substantially similar components, functions and features as described with respect to housing assembly 270 except for second end 272b of housing assembly 270b.

Housing assembly 270 may be described as having a generally hollow, cylindrical configuration defined in part by first housing segment 280 and second housing segment 290. See FIGS. 5E and 5F. The first end of housing segment 280 may generally correspond with first end 271 of housing assembly 270. The second end of second housing segment 290 may generally correspond with second end 272 of housing assembly 270.

First end 291 of second housing segment 290 may be described as having a generally cylindrical configuration with an outside diameter smaller than the adjacent inside diameter of second end 282 of first housing segment 280. First end 291 of second housing segment 290 may slide longitudinally from a first position (See FIG. 5E) to a second position (See FIG. 5F) within second end 282 of first housing segment 280 to release one end of a drive shaft engaged with second end 252 of coupler assembly 250.

A biasing mechanism such as coiled spring 274 may be disposed around exterior portion 260a of generally elongated core 260. See for example FIGS. 5E and 5F. First end 275 of coiled spring 274 may contact annular shoulder 284 formed on interior portions of first housing segment 280. Second end 276 of coiled spring 274 may contact annular shoulder 278 disposed proximate first end 291 of second housing segment 290. Coil spring 274, annular shoulder 284 and annular shoulder 278 may cooperate with each other to generally maintain first housing segment 280 and second housing segment 290 in a first extended position relative to each other. See FIGS. 5A, 5B, 5C, 5E and 5I. Other biasing mechanisms such as, but not limited to, leaf springs and bellows (not expressly shown) may also be disposed between annular shoulder 284 and annular shoulder 278.

Annular shoulder 278, associated with second end 276 of coiled spring 274, may extend radially outward from generally cylindrical ring 277. Generally cylindrical ring 277 may be slidably and rotatably disposed on exterior portion 260a of elongated core 260. Annular shoulder 279 may be disposed on interior portions of generally cylindrical ring 277 and may extend radially inward toward adjacent portions of elongated core 260.

Annular shoulder 268 may be formed on exterior portion 260a of elongated core 260 intermediate first end 261 and second end 262. The configuration and dimensions of annular shoulder 268 and annular shoulder 279 are selected to be compatible with each other such that engagement between annular shoulder 279 of generally cylindrical ring 277 with annular shoulder 268 of elongated core 260 may limit movement of second housing segment 290 longitudinally in the direction of second end 262 of elongated core 260.

For some applications a plurality of flexible collets or fingers 477 may extend from generally cylindrical ring 277 opposite from annular shoulder 278. Respective collet heads 478 may be formed on the end of each collet 477 opposite from annular shoulder 278. The dimensions and configuration of collet heads 478 may be selected to be received within respective slots or openings 297 formed in second housing 290. During manufacture of coupler assembly 250, each collet head 478 may be disposed within respective slot or opening 297 to securely engage generally cylindrical ring 277 and annular shoulder 278 proximate first end 291 of second housing segment 290. As a result, second housing segment 290 and annular shoulder 278 may generally move as a single unit relative to elongated core 260 and first housing segment 280.

During disengagement of an intraosseous device from first end 251 of coupler assembly 250, first housing segment 280 may move or slide longitudinally toward second housing segment 290. In a similar manner, second housing segment 290 may move or slide longitudinally toward first housing segment 280 during disengagement of a powered driver from second end 252 of coupler assembly 250.

Annular shoulder 267 may be formed on exterior portions of elongated core 260 proximate first end 261. Annular shoulder 267 may engage portions of first end 271 of housing 270 to limit longitudinal movement of first housing segment 280 during longitudinal movement of second housing segment 290 towards first end 261 of elongated core 260 during disengagement of a powered driver from second end 252 of coupler assembly 250.

As previously noted, annular shoulder 268 may be formed on exterior portions of elongated core 260 between first end 261 and second end 262. Engagement between annular shoulder 268 and annular shoulder 279 of generally cylindrical ring 277 may limit movement of second housing segment 290 toward second end 262 of elongated core 260. Contact between spring 274 and annular shoulder 278 and annular shoulder 284 of first housing segment 280 may limit the longitudinal movement of first housing segment 280 in the direction of second end 262 of elongated core 260 during disengagement of an intraosseous device from first end 251 of coupler assembly 250.

Generally cylindrical ring 277 and attached annular shoulder 279 may slide longitudinally on exterior portions of annular core 260 between annual shoulder 268 and annular shoulder 267. First housing segment 280 may move longitudinally toward second end 262 of elongated core 260 to release one end of intraosseous device from engagement with first end 251 of coupler assembly 250. In a similar manner, second housing segment 290 may move longitudinally toward first end 261 of elongated core 260 to release one end of a drive shaft extending from a powered driver engaged with second end 252 of coupler assembly 250.

A wide variety of latches and latch mechanisms may be satisfactorily used to releasably engage one end of an intraosseous device within a first end of a coupler assembly incorporating teachings of the present disclosure. In a similar manner, a wide variety of latches and latch mechanisms may be satisfactorily used to releasably engage one end of a drive shaft extending from a powered driver or manual driver within a second end of the coupler assembly incorporating teachings of the present disclosure.

For embodiments represented by coupler assemblies 250, 250a and 250b, first latch 410 may be disposed on exterior portions of elongated core 260 proximate receptacle 263 adjacent to first end 261 to releasably engage one end of an IO device such as second end 102 of biopsy needle set 100b within receptacle 263 of coupler assembly 250, 250a and/or 250b. Second latch mechanism 420 may be disposed on exterior portions of elongated core 260 proximate receptacle 264 adjacent to second end 262 to releasably engage one end of a drive shaft with second end 252 of coupler assembly 250. See FIGS. 5C, 5E and 5I.

Second latch 420 may be used to releasably engage one portion of a drive shaft such as end 224 of drive shaft 222 extending from powered driver 200 within second end 252 of coupler assembly 250, 250a and/or 250b. Latch 410 may releasably engage an intraosseous device with first end 251 of coupler assembly 250 substantially the same latch 420 may releasably engage a powered driver with second end 252 of coupler assembly 250.

For some applications, latches 410 and 420 may have similar configurations such as a general "omega" shape. See latch 420 in FIGS. 5G and 5H. However, latch 410 may have larger dimensions corresponding generally with exterior portion 260a of elongated core 260. Latch 420 may have smaller dimensions corresponding generally with exterior portion 260b of elongated core 260. Various features of the present disclosure may be described with respect to latch mechanism 420 as shown in FIGS. 5G and 5H along with adjacent portions of second housing segment 290 and exterior portion 260b of elongated core 260.

Respective detents 421 and 422 may be formed on opposite ends of generally omega shaped latch 420. See FIGS. 5D, 5G and 5H. In a similar manner, respective detents (not expressly shown) may be formed on the ends of generally omega shaped latch 410. The configuration and dimensions of detents 421 and 422 may be compatible with placing each detent 421 and 422 in respective slot or opening 431 and 432 extending between exterior portion 260b of elongated core 260 to interior portions of receptacle 264 disposed proximate second end 252 of coupler assembly 250.

Figure 5G:
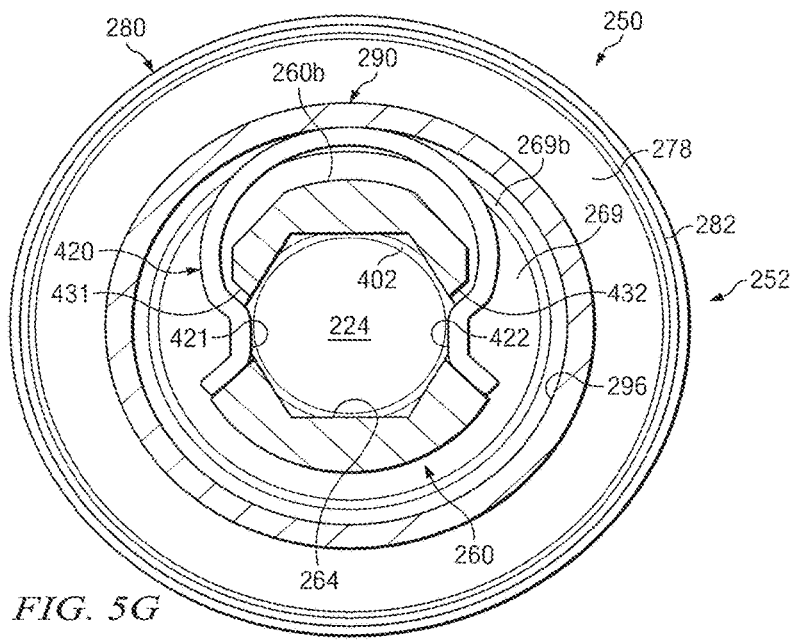
FIG. 5G is a schematic drawing in section showing various features of a coupler assembly and latch mechanism incorporating teachings of the present disclosure taken along lines 5G-5G of FIG. 5E.
Figure 5H:
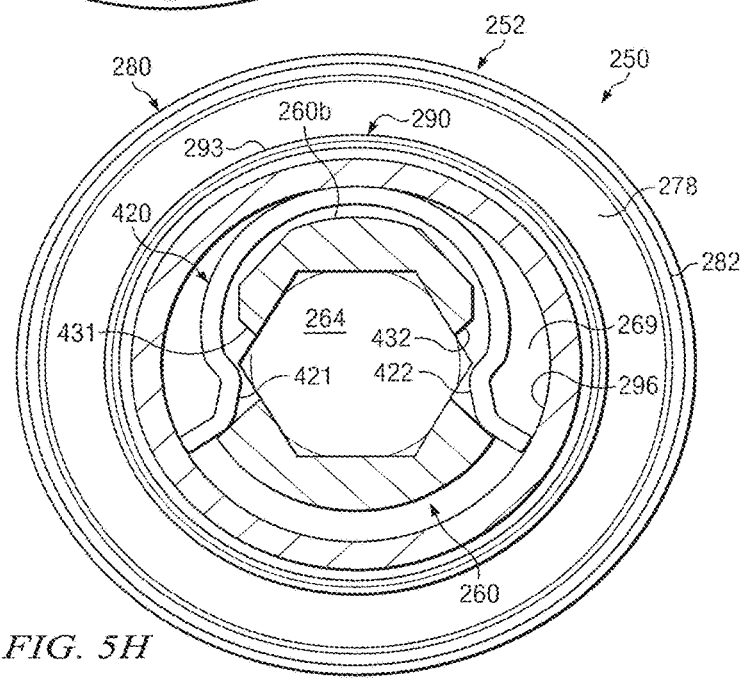
FIG. 5H is a schematic drawing in section showing various features of a coupler assembly and latch mechanism incorporating teachings of the present disclosure taken along lines 5H-5H of FIG. 5F.
Figure 5I:
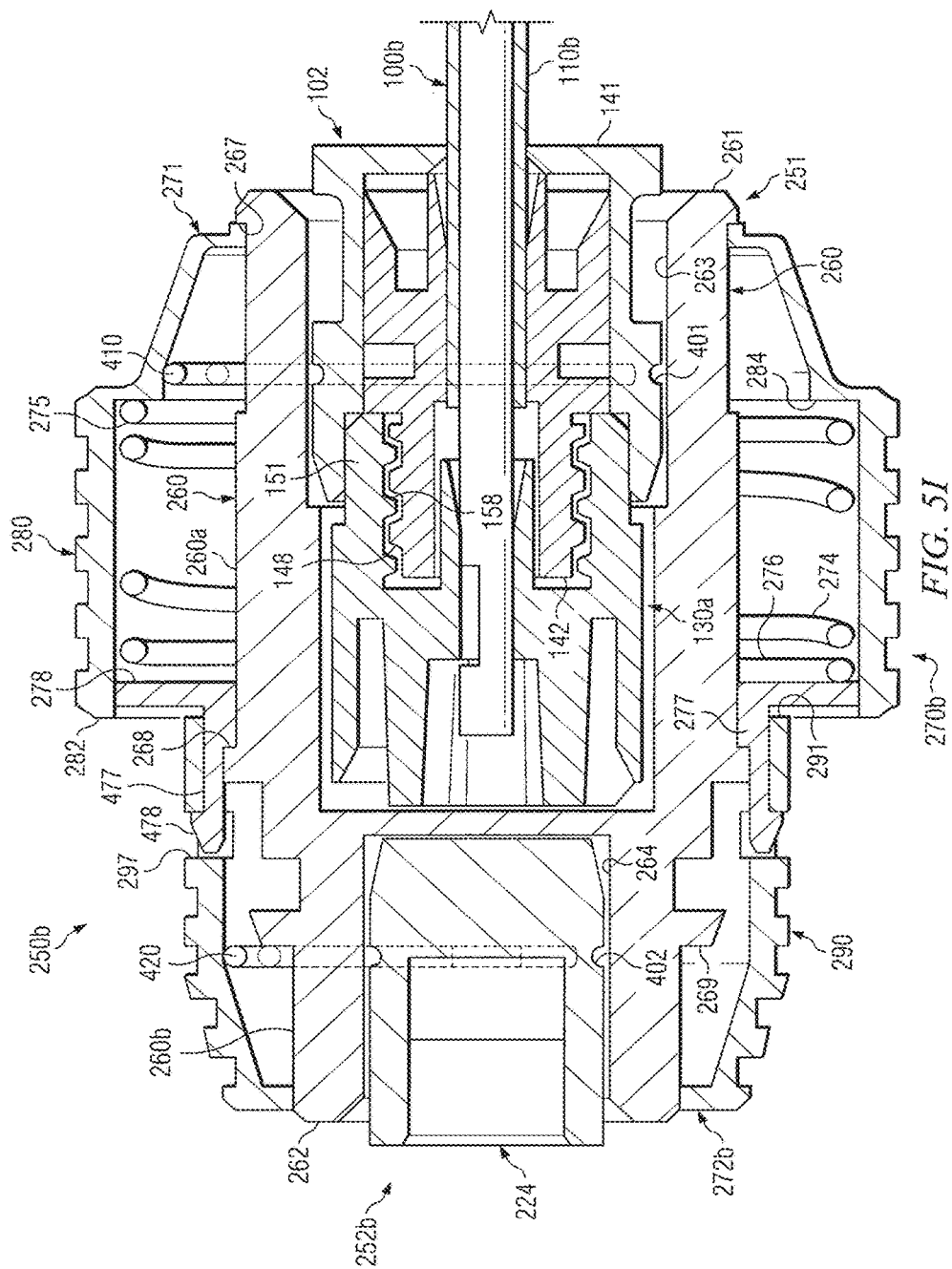
FIG. 5I is a schematic drawing in section with portions broken away showing another example of a coupler assembly incorporating teachings of the present disclosure.

Latch 420 may have a first position such as shown in FIGS. 5D and 5G in which portions of detents 421 and 422 may extend through respective slots 431 and 432. The dimensions and configuration of detent 421 and 422 may be operable to be securely engaged with annular groove 402 formed in end 224 of powered driver 200. In a similar manner, respective detents on associated latch 410 may be releasably engaged with annular groove 401 disposed in second end 102 of biopsy needle 100b.

For some applications, a plurality of tapered surfaces 403 may be formed on exterior portions of hub 140a proximate first end 142 (See FIG. 5C) to radially expand detent mechanisms associated with omega shaped latch 410 radially outward while inserting second end 102 of biopsy needle 100b into first end 251 of coupler assembly 250, 250a or 250b. The detent mechanism may "snap" into annular groove 401 when aligned therewith. In a similar manner, a plurality of tapered surfaces 228 may be formed on exterior portions of end 224 of drive shaft 222 extending from powered driver 200 to radially expand detent mechanisms 421 and 422 radially outward during the insertion of end 224 of powered driver 200 into second end 252 of coupler assembly 250. Detent mechanisms 421 and 422 will "snap" into annular groove 402 when aligned therewith. See FIG. 5F.

Engagement between detent mechanisms associated with latch 410 with annular groove 401 of hub assembly 130*a* will generally retain second end 102 of biopsy needle 100*b* securely engaged with first end 251 of coupler assembly 250. This engagement may allow powered driver 200 to rotate or spin cannula or biopsy needle 110*b* while withdrawing cannula or biopsy needle 110*b* from an insertion site. In a similar manner, engagement between detent mechanisms 421 and 422 of omega shaped latch 420 and annular groove 402 of end 224 of powered driver 200 will generally retain second end 252 of coupler assembly 250 engaged with powered driver 100 during withdrawal of cannula 110*b* from an insertion site.

Biopsy needle set 100*b* may be released from first end 251 of coupler assembly 250 by sliding first housing segment 280 longitudinally toward second end 262 of elongated core 260. Such movement of first housing segment 280 will result in interior tapered surface 286 contacting exterior portions of omega shaped latch 410 and compressing omega shaped latch 410 to radially expand associated detent mechanisms (not expressly shown) from engagement with annular groove 401 of hub assembly 130*a*. As a result, biopsy needle set 100*b* may be easily withdrawn from first end 251 of coupler assembly 250.

In a similar manner, longitudinal movement of second housing segment 290 toward first end 251 of coupler assembly 250 will result in interior tapered surface 296 contacting exterior portions of omega shaped latch 420 to compress generally omega shaped latch 420 and withdraw or retract detent mechanisms 421 and 422 from engagement with annular groove 402 of end 224. See FIGS. 5F and 5H. As a result, powered driver 200 and second end 222 of coupler assembly 250 may be easily disconnected from each other.

Coupler assemblies 250 and 250*a* may have substantially the same overall configuration and dimensions including respective flange 254 extending radially from second end 252 and 252*a*. Flange 254 may be generally described as having an enlarged funnel shaped or bell shaped configuration. The dimensions and configuration of flange 254 may be selected to be compatible with end 211 of powered driver 200. Coupler assembly 250*b* does not have a respective flange 254. See FIG. 5I. Second end 272*b* of housing assembly 270*b* may terminate proximate first end 262 of associated elongated core 260 and associated second end 252*b* of coupler assembly 250*b*.

As previously noted, coupler assembly 250 may be securely engaged with an opening formed in a containment bag or sterile sleeve in accordance with teachings of the present disclosure. For embodiments such as shown in FIGS. 5E and 5F second end 272 of housing 270 of coupler assembly 250 may include annular ring 370 operable to be securely engaged with adjacent portions of flange 254. The outside diameter of annular ring 370 may generally correspond with the outside diameter of adjacent portions of flange 254. The inside diameter of annular ring 370 may also generally correspond with the inside diameter of adjacent portions of flange 254.

For some embodiments a plurality of posts 372 and generally V shaped grooves 374 may be alternatingly disposed on the extreme end of flange 254. Annular ring 370 may include a plurality of holes 371 sized to received respective posts 372 therein. Annular ring 370 may also include a plurality of generally V shaped projections 376 sized to be received within respective generally V shaped grooves 374 formed in adjacent portions of flange 254.

For embodiments such as shown in FIGS. 1C, 1E, 1F, 7A and 7B portions of containment bag 170 adjacent to first opening 171 may be disposed between annular ring 370 and adjacent portions of flange 254. For example, post 372 may be inserted through respective holes (not expressly shown) in containment bag 170 adjacent to the perimeter of opening 171. Holes 371 in annular ring 370 may be aligned with respective posts 372. Other portions of bag 170 adjacent to opening 171 may be trapped between respective V shaped projections 376 and V shaped grooves 374. Various welding techniques including, but not limited to, laser welding may be applied to posts 372 to bond annular ring 370 with adjacent portions of flange 354. As a result, the perimeter of containment bag 170 adjacent to first opening 171 may be securely engaged with second end 252 of coupler assembly 250. See FIGS. 7A and 7B.

FIGS. 6A and 6B are schematic drawings showing powered driver 200*a*, coupler assembly 250*b* and biopsy needle set 100*b* incorporating various teachings of the present disclosure. Coupler assembly 250*b* may include first end 251 operable to be releasably engaged with second end 102 of intraosseous device 100*b*. Coupler assembly 250*b* may also include second end 252 operable to be releasably engaged with end 224*a* of drive shaft 222*a* extending from first end 211 of powered driver 200*a*.

As shown in FIG. 6B, second end 102 of biopsy needle set 100*b* may be releasably disposed within first end 251 of coupler assembly 250*b*. End 224*a* of drive shaft 222*a* extending from end 211 of powered driver 220*a* may be releasably engaged with second end 252*b* of coupler assembly 250. For embodiments represented by coupler assembly 250*b*, second end 252 of coupler assembly 250*b* may include tapered receptacle 264*b* having a configuration and dimensions corresponding generally with tapered end 224*a* of powered driver 220*a*.

Coupler assembly 250*b* may include generally elongated core 260*b* with housing assembly 270*b* slidably disposed on exterior portions of elongated core 260*b* adjacent to first end 251. Second end 272 of housing assembly 270*b* may be disposed adjacent to shoulder 278*b* formed on exterior portions of elongated core 260*b*. Coiled spring 274 may be disposed on exterior portions of elongated core 260*b* between shoulder 284*b* of housing 270*b* and shoulder 278*b* of elongated core 260*b*. Coiled spring 274 may bias housing assembly 270*b* to a first position with first end 271 of housing 270*b* generally aligned with first end 261 of elongated core 260*b*. See FIG. 6B.

For some applications, coupler assembly 250*b* may include latch mechanism 430 disposed proximate second end 252 of coupler assembly 250*b*. Latch mechanism 430 may be generally described as having an "L" shaped configuration defined in part by first segment 431 extending generally parallel with elongated core 260*b* and second segment 432 extending generally perpendicular with respect to elongated core 260*b* proximate second end 262. Second segment 432 may include an enlarged opening 434 sized to allow inserting end 224*a* of powered driver 200*a* into receptacle 264*b*. Segment 432 of latch mechanism 430 may also include detent mechanism 436 sized to be releasably engaged within annular groove 402 proximate end 224*a* of powered driver 200*a*. See FIG. 6B.

During attachment of coupler assembly 250*b* with end 224*a* of powered driver 200, first segment 431 may be manually depressed to compress spring 438 and to move detent mechanism 436 to allow full access to receptacle 264b disposed in second end 252b of coupler assembly 250b. End 224a of powered driver 200a may then be inserted through opening 434 into receptacle 264b. First segment 431 of latch mechanism 430 may next be released, which will allow detent mechanism 436 to be securely engaged within annular groove 402 of end 224a of powered driver 200a. As a result, coupler assembly 250b will remain securely engaged with powered driver 200a until first segment 431 is again depressed to disengage detent mechanism 436 from annular groove 402.

Latch mechanism 410b may be disposed on exterior portions of elongated core 260b proximate first end 261. Latch mechanism 410b may be operable to be releasably engaged with and disengaged from annular 401 in an associated intraosseous device such as annual groove 401 formed in second end 102 of biopsy needle 100b. See FIG. 6B. Housing 270b may slide longitudinally from first end 271 toward second end 252 of coupler assembly 250b to release engagement between latch mechanism 410b and annular groove 401 formed in second end 102 of biopsy needle set 100b.

For some embodiments, annular ring 440 may be disposed on exterior portions of coupler assembly 250b proximate second end 252. Annular ring 440 is shown in FIG. 6B. Annular ring 440 is not shown in FIG. 6A. Groove 442 may be formed in exterior portions of annular ring 440 to accommodate securely engaging the perimeter of a first opening in a containment bag therewith. The dimensions and configuration of annular ring 440 may be selected to allow rotation of coupler assembly 250b within annular ring 440. As a result a containment bag attached with annular ring 440 will generally not be damaged by rotation of coupler assembly 250b.

FIGS. 7A and 7B are schematic drawings showing one example of a containment bag or sterile sleeve engage with a coupler assembly in accordance with teachings of the present disclosure. FIG. 7A shows powered driver 200 prior to placing within containment bag 170. Containment bag 170 may be generally described as having first opening 171 and second opening 172. For some applications, containment bag 170 may be formed from generally clear, flexible plastic-like material.

First opening 171 may be sized to securely engage second end 252 of coupler assembly 250 therewith. For embodiments represented by coupler assembly 250, annular ring 370 may be used to securely engage portions of containment bag 170 proximate first opening 171 with second end 252 of coupler assembly 250. See FIGS. 5E and 5F. A fluid barrier may be formed between portions of containment bag 170 adjacent to first opening 171 and adjacent portions of second end 252 of coupler assembly 250.

The dimensions and configuration of second opening 172 of containment bag 170 are preferably selected to allow inserting powered driver 200 therethrough. Various closure mechanisms may be satisfactorily used to close second opening 172 after end 224 of powered driver 200 has been engaged with second end 252 of coupler assembly 250. For some applications, flap 174 may be folded over second opening 172. Various types of self sealing adhesive materials may be satisfactorily used to releasably engage portions of flap 174 with adjacent portions of containment bag 170. The present disclosure is not limited to using flaps and adhesive materials to close an opening in a containment bag.

Figure 8:
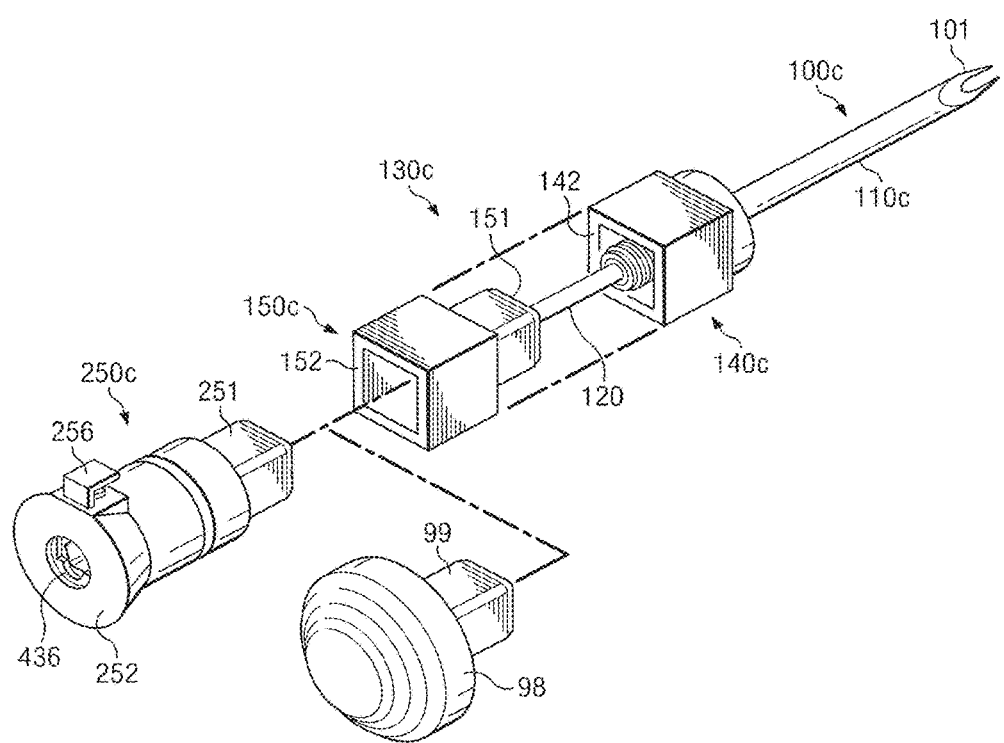
FIG. 8 is a schematic drawing showing an exploded isometric view of an intraosseous device and a coupler assembly incorporating teachings of the present disclosure which may be satisfactorily used with a powered driver in accordance with teachings of the present disclosure or a manual driver.

FIG. 8 is a schematic drawing showing an exploded isometric view of coupler assembly 250c and hub assembly 130c with intraosseous device 100d extending therefrom. First end 101 of intraosseous device 100d may be operable to be inserted into a bone and associated bone marrow. Intraosseous device 100d may include cannula 110c extending from hub 140c. Inner penetrator or trocar 120 may extend from first end 151 of hub 150c. First end 151 of hub 150c may be sized to be releasably inserted into second end 142 of hub 140c. First end 251 of coupler assembly 250c may be releasably inserted into second end 152 of hub 150c. For embodiments such as shown in FIG. 8, first end 251 of coupler assembly 250c, second end 152 of hub 150c, first end 151 of hub 150c and second end 142 of hub 140c may be described as having generally rectangular configurations.

Latch assembly 256 may be satisfactorily used to releasably engage one end of a drive shaft within second end 252d of coupler assembly 250c. For other applications, latch assembly 256 may include detent 436 operable to engage annular groove 402 in end 224a powered driver 200a. For other applications manual drive shaft 99 extending from manual driver 98 may also be releasably engaged with second end 152 of hub 150.

Various types of ejectors, ejector rods, funnels and/or ejector funnels may also be used with a biopsy needle, biopsy needle sets and/or other intraosseous devices incorporating teachings of the present disclosure. For some applications, funnels formed in accordance with teachings of the present disclosure may include a respective first opening formed at a first end and a respective second opening at a second end of the funnel. The first opening and the second opening may have different inside diameters.

For example, the first opening may be sized to accommodate inserting a biopsy needle therein while the second opening may have a reduced inside diameter which prevents inserting the biopsy needle therein. The second opening may be sized to only accommodate one end of an associated ejector rod. For some applications, a longitudinal passageway may extend between the first end and the second end of the funnel. Tapered surfaces may be formed within the longitudinal passageway adjacent to the first end. The tapered surfaces may function as a "one way" connector such that when a biopsy needle is inserted therein, the funnel will be securely engaged with the first end of the biopsy needle. The funnel may then function as a sharps protector for the first end of the biopsy needle.

Figure 9A:
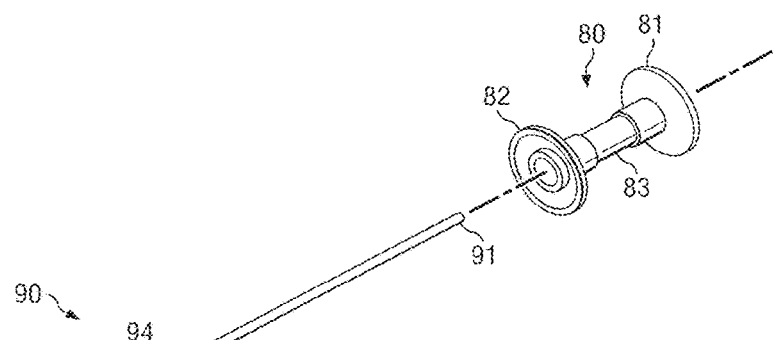
FIG. 9A is a schematic drawing showing an exploded, isometric view of a biopsy specimen ejector and associated funnel incorporating teachings of the present disclosure.
Figure 9B:
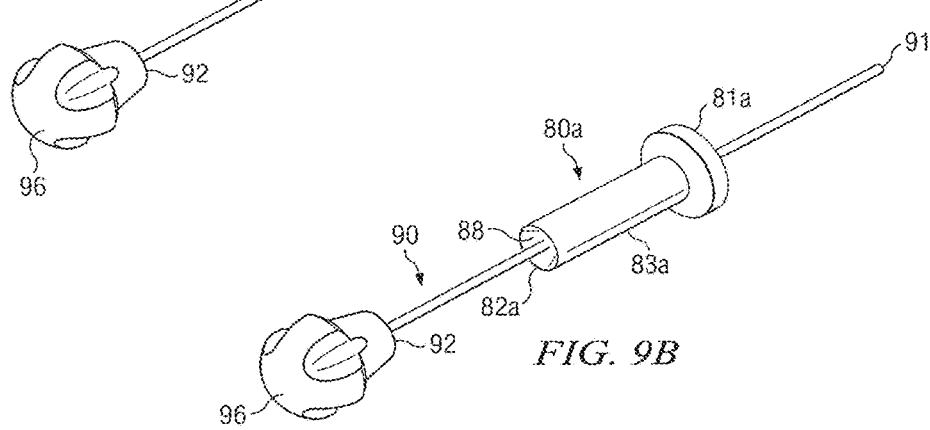
FIG. 9B is a schematic drawing showing an isometric view of another example of a biopsy specimen ejector and associated funnel incorporating teachings of the present disclosure.
Figure 9C:
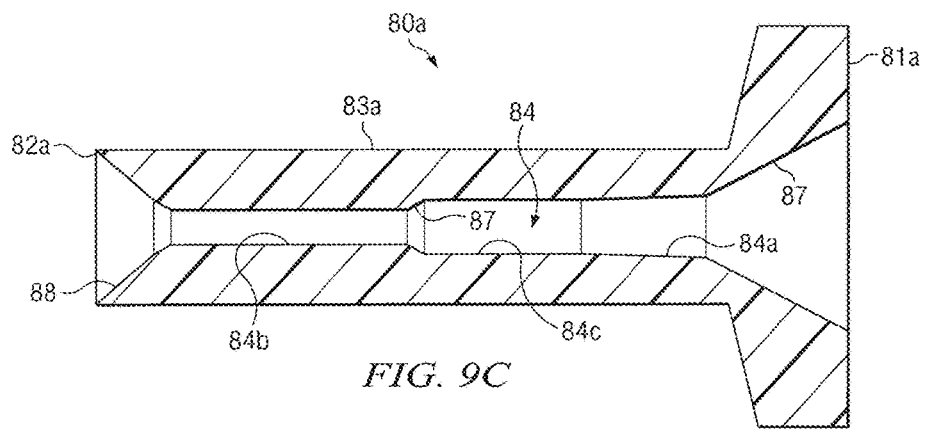
FIG. 9C is a schematic drawing in section of the funnel of FIG. 9B.

FIGS. 9A, 9B and 9C show some examples of apparatus and methods which may be used to remove a biopsy specimen from a generally hollow cannula or biopsy needle after inserting a first end of the generally hollow cannula or biopsy needle into a bone and/or associated bone marrow. Funnel 80 as shown in FIG. 9A may include first end 81 and second end 82 with a generally hollow, cylindrical portion 83 extending therebetween. Generally hollow, cylindrical portion 83 may include a longitudinal passageway (not expressly shown) sized to accommodate one end of an associated intraosseous device and first end 91 of ejector 90. For some applications ejector 90 may also be referred to as an "ejector rod".

The length of ejector 90 may be selected to be greater than the length of a lumen in an associated biopsy needle. Handle or hub 96 may be disposed on second end 92 of ejector 90. The dimensions and configuration of first end 91 of ejector rod 90 may be selected to be compatible with inserting first end 91 through an opening in the first end of an associated biopsy needle.

Funnel 80a as shown in FIGS. 9B and 9C represents an alternative embodiment of the present disclosure. First end 81a of funnel 80a may have a configuration and dimensions compatible with inserting the first end of an intraosseous device such as first end 101 of biopsy needle 100c therein.

Second end 82*a* may have a modified configuration as compared with second end 82 of previously described funnel 80. The dimensions and configuration of second end 82*a* may be selected to be compatible with placing funnel 80*a* in a medical procedure tray with first end 81*a* oriented generally upward to allow inserting one end of an intraosseous device therein. See FIGS. 1C and 1D.

For embodiments such as shown in FIGS. 9B and 9C funnel 80*a* may include first end 81*a* sized to be securely engaged with one end of an intraosseous device such as first end 101 of biopsy needle 100*c*. Funnel 80*a* may include second end 82*a* sized to slidably receive first end 91 of ejector 90 therein. Longitudinal passageway 84 may be disposed in funnel 80*a* extending between first end 81*a* and second end 82*a*.

For some applications first tapered opening 87 may be formed proximate first end 81*a*. Second tapered opening 88 may be formed proximate second end 82*a*. First tapered opening 87 may be sized to allow inserting end 101 of biopsy needle 100*c* through and into first segment 84*a* of longitudinal passageway 84. Second tapered opening 88 may be sized to only allow inserting end 91 of ejector 90 therethrough and into reduced diameter portion 84*b* of longitudinal passageway 84. Reduced diameter portion 84*b* may be smaller than the outside diameter of biopsy needle 100*c* or other intraosseous devices.

For some applications longitudinal passageway 84 may include tapered inside diameter portion 84*a* disposed adjacent to and extending from first opening 87. The tapered inside diameter portion 84*a* may limit movement of the first end 101 of biopsy needle 100*c* or other intraosseous device therethrough. The configuration and dimensions associated with tapered inside diameter portion 84*a* may be described as a "sticking taper" which will result in securely engaging funnel 80*a* with the first end of an intraosseous device inserted therein. As a result of providing a "sticking taper" within longitudinal passageway 84, funnel 80*a* may then be withdrawn from a respective holder in a medical procedure kit to allow inserting injector rod 80 through second end 82*a*. Funnel 80*a* also may serve as a sharps protector since it is now securely engaged with the first end of the associated intraosseous device.

One of the benefits of the present disclosure may include the ability to securely engage one end of an intraosseous device with a funnel without requiring an operator to hold the funnel or the intraosseous device during such engagement. A powered driver and coupler assembly incorporating teachings of the present disclosure may be satisfactorily used to insert the one end of the intraosseous device into the funnel. The coupler assembly may then be releasably disengaged from an opposite end of the intraosseous device.

Benefits of the present disclosure may include reducing physical demands and mental stress on operators and patients by increasing speed and control of aspiration needle insertion during cancellous bone and bone marrow harvesting procedures. A bone marrow aspiration system incorporating teachings of the present disclosure may include a battery powered driver, a coupler assembly, a containment bag and an aspiration needle set. The powered driver, while disposed in a sterile containment bag, may rotate the coupler assembly and attached aspiration needle set to penetrate the cortex of a bone and associated cancellous bone to a desired depth to extract bone marrow. The driver and connector assembly may then be separated from the aspiration needle set. A hub assembly attached to one end of the aspiration needle set may be manipulated to leave an aspiration needle or cannula securely seated in the bone. A standard Luer lock fitting (part of the hub assembly) may be attached with a standard syringe or flexible tubing extending from a bone marrow aspiration system.

Figure 10:
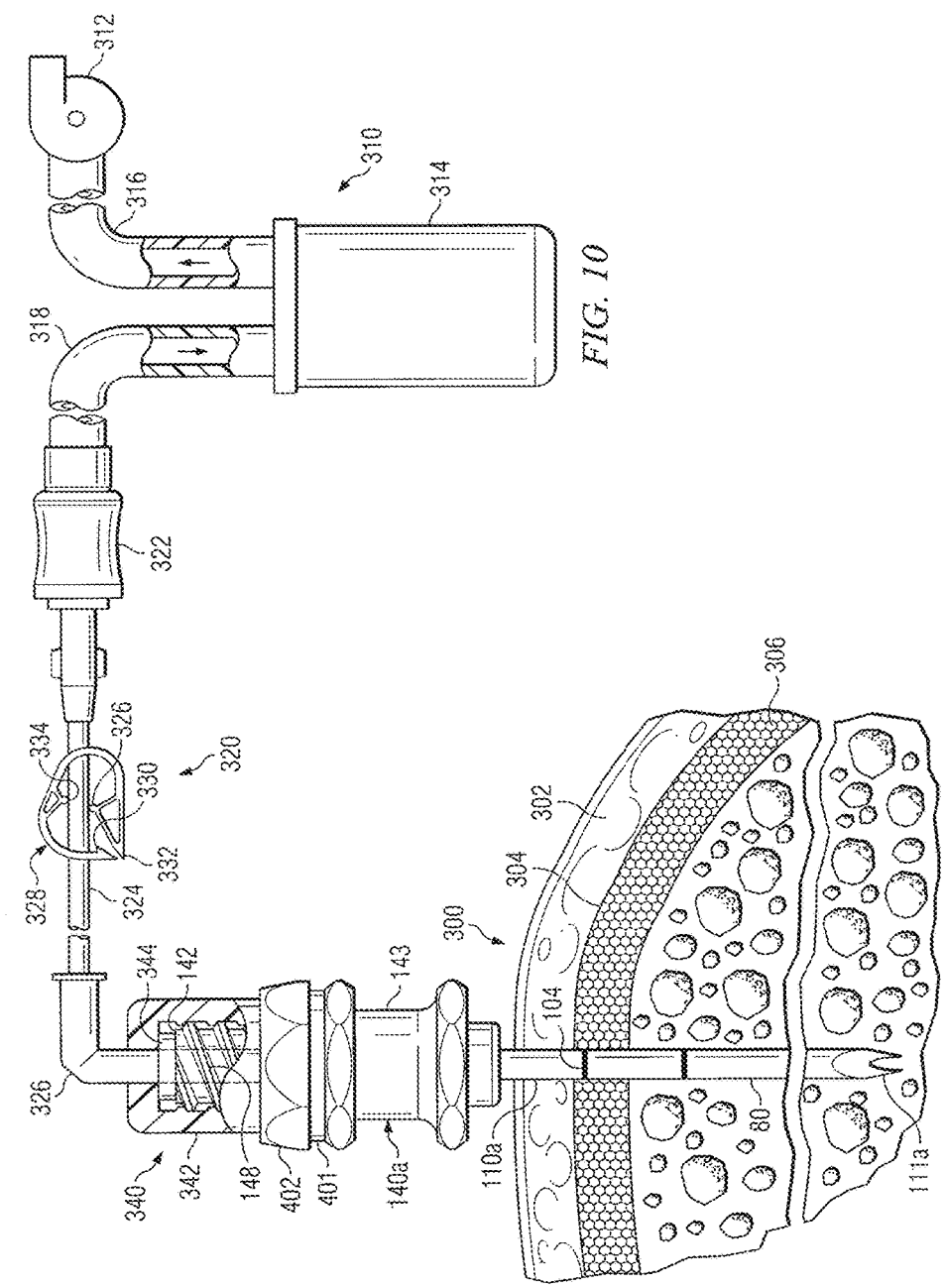
FIG. 10 is a schematic drawing in section and in elevation with portions broken away showing an aspiration needle disposed at a target site and communicating with a bone marrow aspiration system in accordance with teachings of the present disclosure.

FIG. 10 is a schematic drawing showing an aspiration needle disposed in a portion of a hip bone often referred to as the ilium. One of the penetration sites or insertion sites frequently used to obtain bone marrow from a hip bone may be the posterior iliac crest. Another insertion site may be the anterior iliac crest (not expressly shown). Bone marrow may also be aspirated from the tibia (leg bone) and sternum (chest).

Hip bone 300 as shown in FIG. 10 may include three segments—the ilium, the ischium and the pubis. These segments are generally distinct from each other in young patients but are generally fused together in adults. Skin and soft tissue 302 generally cover insertion sites in crest 304 of the ilium.

All bones generally include a tough, hard to penetrate layer of cortex. Crest 304 OF HIP BONE 300 typically includes cortex layer 306. FIG. 10 shows enlarged skin and soft tissue layer 302 and cortex layer 306 for illustration purposes only. A typical thickness for skin and soft tissue layer 302 may be seven to eight millimeters (7 mm to 8 mm). A typical thickness for cortex layer 306 may be approximately two millimeters (2 mm).

As previously discussed intraosseous (IO) device or aspiration needle set 100*a* may be inserted in the crest of the ilium or any other insertion site with minimum trauma to obtain bone and/or bone marrow samples in accordance with teachings of the present disclosure.

FIG. 10 shows one example of a system for aspirating bone marrow from a bone using apparatus and methods incorporating teachings of the present disclosure. Samples of bone and/or bone marrow may be obtained from any suitable bone including, but not limited to, tibia (leg bone), ilium (pelvis) or sternum (chest) using apparatus and methods incorporating teachings of the present disclosure. FIG. 10 shows cannula or aspiration needle 110*a* inserted into a target area in a patient's ilium.

For one embodiment, system 310 may include a source of vacuum or low pressure 312, collection container 314, vacuum tubing 316 and collection tubing 318. Source of vacuum 312 may be a pump such as shown in FIG. 10 or may be a portion of a hospital or operating suite low pressure vacuum system (not expressly shown). Vacuum tubing 316 may extend between vacuum source 312 and collection container 314. Various types of tubing may be satisfactorily used to form vacuum tubing 316 and/or collection tubing 318. The length of vacuum tubing 316 and/or collection tubing 318 may be varied depending upon each facility in which system 310 is used.

Collection tubing 318 may extend between collection container 314 and intraosseous (IO) connector assembly 320. Various types of connections and connector assemblies including, but not limited to, IO connector assembly 320 may be used to communicate fluids between an IO device such as aspiration needle 110*a* and collection tubing 318.

IO connector assembly 320 may include coupling or tubing connector 322 operable to be releasably engaged with one end of collection tubing 318 opposite from container 314. Various types of couplings associated with IV tubing may be satisfactorily used. Relatively short, flexible tubing 324 may extend between tubing connector 322 and right angle connector 326. For some applications, flow control device or tubing stop 328 may be attached to flexible tubing 324 between coupling 322 and right angle connector 326.

Flow control device 328 may have a first, open position as shown in FIG. 10 and a second, closed position (not expressly shown). Flow control device 328 may be used to prevent fluid flow from IO device 110a during engagement and disengagement with collection tubing 318 or any other apparatus such as IV tubing (not expressly shown) which may be attached to IO connector assembly 320.

Flow control device 328 may be formed from relatively flexible material which allows compressing or squeezing flow control device 328 to engage notch or hook 330 with end 332. Compression of flow control device 328 will preferably result in clamps 334 and 336 compressing or closing off fluid flow through the lumen of flexible tubing 324. Engagement of notch 330 with end 336 will hold flow control device 328 in its second, closed position.

Right angle connector 326 may be engaged with one end of flexible tubing 324 opposite from coupling 322. Right angle connector 326 allows flexible tubing 324 to be connected to aspiration needle 110a at an angle that will generally not kink or pinch off the lumen of tubing 324. Right angle connector 326 may also include Luer connector 340 operable to be releasably connected with second end 142 of first hub 140a. A tapered portion (not expressly shown) of Luer connector 340 may be inserted into tapered opening 144 formed in second end 142 of first hub 140a.

Lock nut 342 may be disposed on exterior portions of right angle connector 326 adjacent to Luer connector 340. Flange 344 may also be formed on the exterior of right angle connector 326 adjacent Luer connector 340. Lock nut 342 may be both rotatably and slidably disposed on the exterior portion of right angle connector 326 adjacent to Luer connector 340 with flange 344 disposed between lock nut 342 and Luer connector 340. Threads 346 formed on interior portions of lock nut 342 may be used to releasably engage right angle connector 326 with threads 148 formed adjacent to second end 142 of first hub 140a.

After aspirating a desired bone marrow sample from the target area shown in FIG. 10, IO connector assembly 320 may be disconnected from second end 142 of first hub 140a. Second hub 150a (with or without a trocar attached thereto) may be reconnected with second end 142 of first hub 140a. Powered driver 200 and coupler assembly 250 may be reconnected to hub assembly 130a to remove (power out) aspiration needle 110a or insert aspiration needle 110a to another target area in hip bone 300.

Although the present disclosure and its advantages have been described in detail, it should be understood that various changes, substitutions and alternations can be made herein without departing from the spirit and scope of the invention as defined by the following claims.

What is claimed is:

1. A coupler assembly operable to releasably engage one end of a drive shaft extending from a powered driver with an intraosseous (IO) device having a first end operable to penetrate a bone and associated bone marrow, the coupler assembly having a first end and a second end, the coupler assembly comprising:
    an elongated core having a first end operable to be releasably engaged with a second end of the IO device;
    the elongated core having a second end operable to be releasably engaged with the one end of the drive shaft extending from the powered driver;
    a housing assembly having a first end and a second end with respective openings formed in the first end and the second end of the housing assembly;
    the openings in the first end and the second end of the housing assembly each having dimensions and configurations selected to be compatible with exterior portions of the elongated core disposed within the housing assembly;
    a biasing mechanism disposed between an interior shoulder of the housing assembly and an exterior shoulder of the elongated core, where the biasing mechanism is operable to bias a first portion of the housing assembly and a second portion of the housing assembly to a first position, where the first end of the housing assembly is closer to the first end of the elongated core when the first portion of the housing assembly is in the first position than in a second position, and where the second end of the housing assembly is closer to the second end of the elongated core when the second portion of the housing assembly is in the first position than in the second position;
    a first receptacle disposed in the first end of the elongated core at a location corresponding with the first end of the coupler assembly; and
    a second receptacle disposed in the second end of the elongated core at a location corresponding with the second end of the coupler assembly,
    where the first portion of the housing assembly is configured to slide along a longitudinal length of the core between the first position and the second position,
    where the second portion of the housing assembly is configured to slide along a longitudinal length of the core between the first position and the second position,
    where the second portion of the housing assembly is configured to slide over the elongated core relative to the first portion of the housing assembly, and
    where the first end of the elongated core has an outer diameter that is greater than an outer diameter of the second end of the elongated core.

2. The coupler assembly of claim 1 further comprising:
    the elongated core operable to rotate in response to rotation of the one end of the drive shaft by the powered driver; and
    exterior portions of the elongated core and interior portions of the housing assembly operable to allow the housing assembly to rotate with the elongated core or to not rotate with the elongated core.

3. The coupler assembly of claim 1 further comprising:
    a first latch mechanism disposed proximate the first end of the housing and a second latch mechanism disposed proximate the second end of the housing;
    the first latch mechanism operable to be releasably engaged with the second end of the IO device disposed in the first receptacle; and
    the second latch mechanism operable to be releasably engaged with the one end of the drive shaft disposed in the second receptacle of the elongated core.

4. The coupler assembly of claim 3 further comprising:
    the first latch mechanism having a omega shape with a portion of the elongated core extending through the first latch mechanism; and
    the second latch mechanism having a omega shape with another portion of the elongated core extending through the second latch mechanism.

5. The coupler assembly of claim 1 further comprising an arrow disposed on exterior portions of the housing assembly with the arrow pointing from the first end of the coupler assembly towards the second end of the coupler assembly.

6. The coupler assembly of claim 1, where, when the first portion of the housing assembly is in the first position, the first end of the elongated core is adjacent to the first end of the housing.

7. The coupler assembly of claim 1, where the second receptacle disposed in the second end of the elongated core comprises a cross-section that matches a cross-section of the drive shaft extending from the powered driver.

8. The coupler assembly of claim 1, where the elongated core comprises a first exterior portion and a second exterior portion,
where the first exterior portion comprises a cylindrical configuration,
where the second exterior portion comprises one or more shoulders and recesses.

9. The coupler assembly of claim 1, where a first end of the second portion of the housing assembly is further configured to slide along a longitudinal length of the core between the first position and the second position within a second end of the first housing portion.

10. The coupler assembly of claim 1, where the first end of the elongated core is operable to receive the second end of the IO device when the first portion of the housing assembly is in the second position.

11. The coupler assembly of claim 10, where the first end of the elongated core engages with the second end of the IO device when the first portion of the housing assembly is in the first position.

12. The coupler assembly of claim 9, where the second end of the elongated core is operable to receive the one end of the drive shaft extending from the powered driver when the second portion of the housing assembly is in the second position.

13. The coupler assembly of claim 12, where the second end of the elongated core engages with the one end of the drive shaft extending from the powered driver when the second portion of the housing assembly is in the first position.

14. The coupler assembly of claim 1, further comprising:
a first annular shoulder formed on an interior portion of the housing assembly; and
a second annular shoulder extending from an exterior surface of the elongated core,
where a first end of the biasing mechanism engages the first annular shoulder and a second end of the biasing mechanism engages the second annular shoulder.

15. The coupler assembly of claim 9, further comprising:
a third annular shoulder formed on an interior portion of the housing assembly; and
a fourth annular shoulder formed on an exterior portion of the elongated core,
the third annular shoulder is operable to engage with the fourth annular shoulder to limit longitudinal movement of the second portion of the housing assembly towards the second end of the elongated core.

16. The coupler assembly of claim 9, where the first portion of the housing assembly comprises one or more collets operable to movably attach the first portion of the housing assembly to the second portion of the housing assembly,
where the second portion of the housing assembly comprises one or more openings operable to receive the one or more collets,
where the one or more collets attaches the first portion of the housing assembly to the second portion of the housing assembly when the one or more collets is received in the one or more openings.

17. A coupler assembly operable to releasably engage one end of a drive shaft extending from a powered driver with an intraosseous (IO) device having a first end operable to penetrate a bone and associated bone marrow, the coupler assembly having a first end and a second end, the coupler assembly comprising:
an elongated core having a first end operable to be releasably engaged with a second end of the TO device;
the elongated core having a second end operable to be releasably engaged with the one end of the drive shaft extending from the powered driver;
a housing assembly having a first end and a second end with respective openings formed in the first end and the second end of the housing assembly;
the openings in the first end and the second end of the housing assembly each having dimensions and configurations selected to be compatible with exterior portions of the elongated core disposed within the housing assembly;
a biasing mechanism disposed between an interior shoulder of the housing assembly and an exterior shoulder of the elongated core, where the biasing mechanism is operable to bias a first portion of the housing assembly and a second portion of the housing assembly to a first position, where the first end of the housing assembly is closer to the first end of the elongated core when the first portion of the housing assembly is in the first position than in a second position, and where the second end of the housing assembly is closer to the second end of the elongated core when the second portion of the housing assembly is in the first position than in the second position;
a first annular shoulder formed on an interior portion of the housing assembly; and
a second annular shoulder extending from an exterior surface of the elongated core,
where a first end of the biasing mechanism engages the first annular shoulder and a second end of the biasing mechanism engages the second annular shoulder,
where the first portion of the housing assembly is configured to slide along a longitudinal length of the core between the first position and the second position,
where the second portion of the housing assembly is configured to slide along a longitudinal length of the core between the first position and the second position, and
where the second portion of the housing assembly is configured to slide over the elongated core relative to the first portion of the housing assembly.

18. A coupler assembly operable to releasably engage one end of a drive shaft extending from a powered driver with an intraosseous (IO) device having a first end operable to penetrate a bone and associated bone marrow, the coupler assembly having a first end and a second end, the coupler assembly comprising:
an elongated core having a first end operable to be releasably engaged with a second end of the TO device, and a second end operable to be releasably engaged with the one end of the drive shaft extending from the powered driver;
a housing assembly having a first housing segment and a second housing segment, the first and second housing segments configured to slide along a longitudinal length of the elongated core, and the second housing segment configured to slide over the elongated core relative to the first housing segment;
a biasing mechanism disposed between an interior shoulder of the housing assembly and an exterior shoulder of the elongated core to bias the first housing segment and the second housing segment in a first extended position;

a first receptacle disposed in the first end of the elongated core at a location corresponding with the first end of the coupler assembly; and a second receptacle disposed in the second end of the elongated core at a location corresponding with the second end of the coupler assembly.

19. The coupler assembly of claim 18, further comprising an annular shoulder disposed proximate a first end of the second housing segment and configured to contact the biasing mechanism.

20. The coupler assembly of claim 19, wherein the annular shoulder is configured to move with the second housing segment as a single unit relative to the elongated core.

* * * * *